(12) United States Patent
Boyer et al.

(10) Patent No.: US 9,073,926 B2
(45) Date of Patent: Jul. 7, 2015

(54) HETEROCYCLIC COMPOUNDS CONTAINING A PYRROLOPYRIDINE OR BENZIMIDAZOLE CORE

(75) Inventors: Stephen James Boyer, Bethany, CT (US); Jennifer Burke, Cheshire, CT (US); Xin Guo, Danbury, CT (US); Thomas Martin Kirrane, Jr., Middlebury, CT (US); Roger John Snow, Danbury, CT (US); Yunlong Zhang, North Haven, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 404 days.

(21) Appl. No.: 13/513,973

(22) PCT Filed: Dec. 1, 2010

(86) PCT No.: PCT/US2010/058482
§ 371 (c)(1),
(2), (4) Date: Aug. 7, 2012

(87) PCT Pub. No.: WO2011/071725
PCT Pub. Date: Jun. 16, 2011

(65) Prior Publication Data
US 2013/0137680 A1    May 30, 2013

Related U.S. Application Data

(60) Provisional application No. 61/267,181, filed on Dec. 7, 2009.

(51) Int. Cl.
*A61K 31/55* (2006.01)
*C07D 487/04* (2006.01)
*C07D 471/04* (2006.01)
*C07D 471/14* (2006.01)

(52) U.S. Cl.
CPC ............ *C07D 487/04* (2013.01); *C07D 471/04* (2013.01); *C07D 471/14* (2013.01)

(58) Field of Classification Search
CPC ... A61K 31/55; A61K 31/551; C07D 487/04; C07D 471/04; C07D 495/04
USPC ................... 514/220, 250; 544/346; 540/498

See application file for complete search history.

(56) References Cited

U.S. PATENT DOCUMENTS

2006/0276453 A1   12/2006   Goldberg et al.
2013/0137680 A1    5/2013   Boyer et al.

FOREIGN PATENT DOCUMENTS

WO    2009040512 A2    4/2009
WO    2011071716 A1    6/2011

OTHER PUBLICATIONS

Bain, Jenny et al. "The Selectivity of Protein Kinase Inhibitors: A Further Update" Biochem J. (2007) vol. 408, pp. 297-315.
International Search Report for PCT/US2010/058482 filed on Dec. 1, 2010.
Sapkota, Gopal P. et al. "BI-D1870 is a specific inhibitor of the p90 RSK (ribosomal S6 kinase) isoforms in vitro and in vivo" Biochem J. (2007) vol. 401, pp. 29-38.
Xiong, Zhaoming, et al. "Synthesis and SAR studies of indole-based MK2 inhibitors" Bioorganic & Medicinal Chemistry Letters 18 (2008) pp. 1994-1999.

*Primary Examiner* — Jason Sims
*Assistant Examiner* — Ibrahim D Bori
(74) *Attorney, Agent, or Firm* — Michael P. Morris; Usha R. Patel

(57) ABSTRACT

The present invention relates to compounds of Formula (I) and pharmaceutically acceptable salt thereof, wherein $R^1$, $R^2$, $R^3$, $R^4$, $R^5$ and n are as defined herein. The invention also relates to pharmaceutical compositions comprising these compounds, methods of using these compounds in the treatment of various diseases and disorders, processes for preparing these compounds and intermediates useful in these processes.

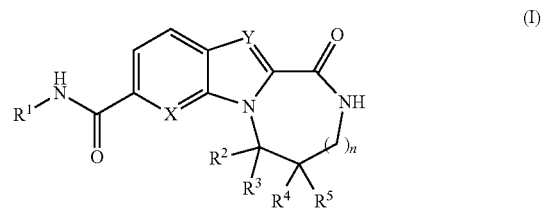

13 Claims, No Drawings

HETEROCYCLIC COMPOUNDS CONTAINING A PYRROLOPYRIDINE OR BENZIMIDAZOLE CORE

This application is the national phase entry under 35 U.S.C. §371 of International Application No. PCT/US2010/058482, filed Dec. 1, 2010, which claims priority to U.S. Provisional Application No. 61/267,181, filed Dec. 7, 2009, which are hereby incorporated by reference in their entireties.

TECHNICAL FIELD

The present invention relates to novel compounds which inhibit RSK, methods of making such compounds and their use as medicaments.

BACKGROUND

The p90 ribosomal s6 kinases (RSKs) are a group of serine/threonine kinases that are constituents of the AGC subfamily in the human kinome. Each of the 4 RSK isoforms are products of separate genes and are characterized by 75%-80% sequence identity. While the RSK isoforms are widely distributed among human tissues, their variable tissue expression patterns indicate that they may have distinct physiologic/pathologic roles. The RSK isoforms are activated by growth factors, cytokines, peptide hormones and neurotransmitters that stimulate the Ras-ERK pathway.

RSK regulates numerous biological processes through its phosphorylation of cellular substrates. One important cardiovascular target of RSK is the $Na^+/H^+$ exchanger isoform 1 (NHE1). RSK-mediated phosphorylation of NHE1 at S703 is responsible for increased NHE1 activity following Ang II stimulation, oxidative stress, and myocardial injury. NHE1 is a highly validated target for its role in both ischemia reperfusion (I/R) injury and congestive heart failure. Increased NHE1 activity correlates to the extent of myocardial damage following I/R, while NHE1 inhibitors administered in a prophylactic manner are capable of preserving cardiac function after I/R. Additionally, increased NHE1 activity is observed in isolated myocytes from failing human hearts and in animal models of hypertrophy suggesting chronic activation of this exchanger in cardiovascular pathologies. Despite robust preclinical data linking NHE1 activity to cardiovascular dysfunction, there are currently no approved NHE1 inhibitors on the market. Adverse events, such as headache, eye pain, and paresthesia, were reported in clinical trials, and it is hypothesized that these events are due to direct and complete NHE1 inhibition which impairs its physiological function of maintaining intracellular pH. Based on this safety concern, alternate approaches that do not inhibit basal NHE1 activity but regulate activity during periods of cardiovascular stress may offer an additional safety margin.

In cardiomyocytes RSK has been recognized as a predominant kinase that phosphorylates the c-terminal regulatory region of NHE1 and is required for NHE1 activation in response to I/R, oxidative stress, and receptor activation by Ang II and phenylephrine. Recent studies by Maekawa et al. (Naoya Maekawa, Jun-ichi Abe, Tetsuro Shishido, Seigo Itoh, Bo Ding, Virendra K. Sharma, Shey-Shing Sheu, Burns C. Blaxall and Bradford C. Berk *Circulation* 113:2516-2523, 2006) demonstrated that that RSK was rapidly activated in the heart tissue exposed to I/R. Furthermore, cardiomyocyte specific expression of dominant negative RSK prevented cardiomyocyte apoptosis and improved post MI remodeling and left ventricular function. Importantly, inhibition of RSK activity by means of overexpressing a dominant negative RSK protein decreased agonist-activated NHE1 function without affecting basal, homeostatic NHE1 function. Similarly, the RSK inhibitor, fmk, has been shown to inhibit phosphorylation of NHE1 and phenylephrine-induced enhanced NHE1 activity without affecting basal activity (Friederike Cuello, Andrew K. Snabaitis, Michael S. Cohen, Jack Taunton, and Metin Avkiran, *Mol Pharmacol* 71:799-806, 2007). These findings suggest that inhibition of RSK activity may be an alternative therapeutic strategy by which NHE1 activity can be differentially regulated, effectively preserving basal function and increasing the safety window.

SUMMARY OF THE INVENTION

The present invention provides novel compounds which inhibit RSK2 activity and are thus useful for treating a variety of diseases and disorders that are mediated through the activity of RSKs including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

In its broadest embodiment the present invention relates to a compound of formula (I)

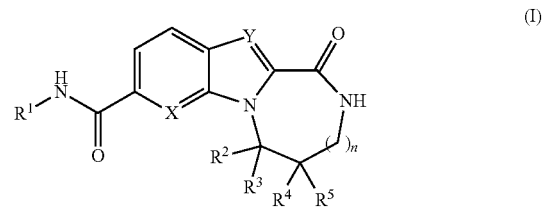

Wherein:
X is N or C;
Y is C or N;
wherein when X=N then Y=C and when X=C then Y=N;
$R^1$ is aryl or heteroaryl; wherein each of the foregoing $R^1$ groups is optionally substituted with 1 to 3 substituents selected from $R^6$;
$R^2$ and $R^3$ are each independently H or $C_1$-$C_5$ alkyl; or
$R^2$ and $R^3$ together with the carbon atom to which they are attached, form a $C_3$-$C_8$ cycloalkyl ring;
$R^4$ and $R^5$ are each independently H or $C_1$-$C_5$ alkyl; or
$R^4$ and $R^5$ together with the carbon atom to which they are attached, form a $C_3$-$C_8$ cycloalkyl ring;
each $R^6$ is independently $C_1$-$C_5$ alkyl, —$C_1$-$C_5$ alkylamino, —$C_1$-$C_5$ alkyl-NH—$C_1$-$C_3$ alkyl, —$C_1$-$C_5$ alkyl-N($C_1$-$C_3$ alkyl)$_2$, —$C_1$-$C_5$ alkyl-aryl, —$C_1$-$C_5$ alkyl-heteroaryl, —$C_1$-$C_5$ alkyl-heterocyclyl, $C_1$-$C_5$ alkoxyl, $C_3$-$C_8$ cycloalkyl, —C(O)$NH_2$, —C(O)NH—$C_1$-$C_5$ alkyl, —C(O)N($C_1$-$C_5$ alky)$_2$, —C(O)NH—$C_3$-$C_8$ cycloalkyl, —C(O)O$C_1$-$C_5$ alkyl, halogen, cyano, heterocyclyl, aryl or heteroaryl; wherein each aryl and heteroaryl of said $R^6$ is optionally independently substituted with 1 to 2 of $C_1$-$C_5$ alkyl;
n is 0 or 1;
or a pharmaceutically acceptable salt thereof.

The compound according to the broadest embodiment described immediately above and wherein:
X is C;
Y is N;

R$^1$ is aryl or heteroaryl; wherein each of the foregoing R$^1$ groups is optionally substituted with 1 to 3 substituents selected from R$^6$;
R$^2$ and R$^3$ are each independently H or C$_1$-C$_5$ alkyl; or
R$^2$ and R$^3$ together with the carbon atom to which they are attached, form a C$_3$-C$_8$ cycloalkyl ring;
R$^4$ and R$^5$ are each independently H or C$_1$-C$_5$ alkyl; or
R$^4$ and R$^5$ together with the carbon atom to which they are attached, form a C$_3$-C$_8$ cycloalkyl ring; and
each R$^6$ is independently C$_1$-C$_5$ alkyl, —C$_1$-C$_5$ alkylamino, —C$_1$-C$_5$ alkyl-NH—C$_1$-C$_3$ alkyl, —C$_1$-C$_5$ alkyl-N(C$_1$-C$_3$ alkyl)$_2$, —C$_1$-C$_5$ alkyl-aryl, —C$_1$-C$_5$ alkyl-heteroaryl, —C$_1$-C$_5$ alkyl-heterocyclyl, C$_1$-C$_5$ alkoxyl, C$_3$-C$_8$ cycloalkyl, —C(O)NH$_2$, —C(O)NH—C$_1$-C$_5$ alkyl, —C(O)N(C$_1$-C$_5$ alky)$_2$, —C(O)NH—C$_3$-C$_8$ cycloalkyl, —C(O)OC$_1$-C$_5$ alkyl, halogen, cyano, heterocyclyl, aryl or heteroaryl; wherein each aryl and heteroaryl of said R$^6$ is optionally independently substituted with 1 to 2 of C$_1$-C$_5$ alkyl; and
n is 0 or 1;
or a pharmaceutically acceptable salt thereof.

The compound according to the embodiment described immediately above and wherein:
R$^1$ is phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl, indolyl, or quinolinyl; wherein each of the foregoing R$^1$ groups is optionally substituted with 1 to 3 substituents selected from R$^6$;
R$^2$ and R$^3$ are each independently H or C$_1$-C$_3$ alkyl; or
R$^2$ and R$^3$ together with the carbon atom to which they are attached, form a C$_3$-C$_6$ cycloalkyl ring;
R$^4$ and R$^5$ are each independently H or C$_1$-C$_3$ alkyl; or
R$^4$ and R$^5$ together with the carbon atom to which they are attached, form a C$_3$-C$_6$ cycloalkyl ring; and
each R$^6$ is independently C$_1$-C$_5$ alkyl, —C$_1$-C$_5$ alkylamino, —C$_1$-C$_5$ alkyl-NH—C$_1$-C$_3$ alkyl, —C$_1$-C$_5$ alkyl-N(C$_1$-C$_3$ alkyl)$_2$, —C$_1$-C$_5$ alkyl-phenyl, C$_1$-C$_3$ alkoxyl, C$_3$-C$_6$ cycloalkyl, —C(O)NH$_2$, —C(O)NH—C$_1$-C$_3$ alkyl, —C(O)N(C$_1$-C$_3$ alkyl)$_2$, —C(O)NH—C$_3$-C$_6$ cycloalkyl, halogen, cyano, phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl or quinolinyl; wherein each heteroaryl of said R$^6$ is optionally independently substituted with 1 to 2 of C$_1$-C$_3$ alkyl;
or a pharmaceutically acceptable salt thereof.

The compound according to the embodiment described immediately above and wherein:
R$^1$ is phenyl, isoxazolyl, imidazolyl, pyrazolyl, pyridinyl, benzimidazolyl, pyrazolopyridinyl, imidazopyridinyl or quinolinyl; wherein each of the foregoing R$^1$ groups is optionally substituted with 1 to 3 substituents selected from R$^6$;
R$^2$ and R$^3$ are each independently H or C$_1$-C$_3$ alkyl;
R$^4$ and R$^5$ are each independently H or C$_1$-C$_3$ alkyl;
each R$^6$ is independently C$_1$-C$_5$ alkyl, —C$_1$-C$_5$ alkyl-N(C$_1$-C$_2$ alkyl)$_2$, —CH$_2$-phenyl, —C(O)NH$_2$, —C(O)NH—C$_3$-C$_6$ cycloalkyl, halogen, phenyl imidazolyl or thiazolyl; wherein each heteroaryl of said R$^6$ is optionally independently substituted with 1 to 2 of C$_1$-C$_3$ alkyl; and
n is 1;
or a pharmaceutically acceptable salt thereof.

The compound according to the embodiment described immediately above and wherein:
R$^1$ is benzimidazolyl substituted with 1 to 2 substituents selected from R$^6$;
R$^2$ and R$^3$ are each independently H or methyl;
R$^4$ and R$^5$ are H; and
R$^6$ is C$_1$-C$_3$ alkyl;
or a pharmaceutically acceptable salt thereof.

A compound according to the broadest embodiment, wherein:
X is N;
Y is C;
R$^1$ is aryl or heteroaryl, each optionally substituted with 1 to 3 substituents selected from R$^6$;
R$^2$ and R$^3$ are each independently H or C$_1$-C$_5$ alkyl; or
R$^2$ and R$^3$ together with the carbon atom to which they are attached, form a C$_3$-C$_8$ cycloalkyl ring;
R$^4$ and R$^5$ are each independently H or C$_1$-C$_5$ alkyl; or
R$^4$ and R$^5$ together with the carbon atom to which they are attached, form a C$_3$-C$_8$ cycloalkyl ring;
each R$^6$ is independently C$_1$-C$_5$ alkyl, —C$_1$-C$_5$ alkylamino, —C$_1$-C$_5$ alkyl-NH—C$_1$-C$_3$ alkyl, —C$_1$-C$_5$ alkyl-N(C$_1$-C$_3$ alkyl)$_2$, —C$_1$-C$_5$ alkyl-aryl, —C$_1$-C$_5$ alkyl-heteroaryl, —C$_1$-C$_5$ alkyl-heterocyclyl, C$_1$-C$_5$ alkoxyl, C$_3$-C$_8$ cycloalkyl, —C(O)NH$_2$, —C(O)NH—C$_1$-C$_5$ alkyl, —C(O)N(C$_1$-C$_5$ alky)$_2$, —C(O)NH—C$_3$-C$_8$ cycloalkyl, —C(O)OC$_1$-C$_5$ alkyl, halogen, cyano, heterocyclyl, aryl or heteroaryl; wherein each aryl and heteroaryl of said R$^6$ is optionally independently substituted with 1 to 2 of C$_1$-C$_5$ alkyl; and
n is 0 or 1;
or a pharmaceutically acceptable salt thereof.

The compound according to the embodiment described immediately above and wherein:
R$^1$ is phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl or quinolinyl; wherein each of the foregoing R$^1$ groups is optionally substituted with 1 to 3 substituents selected from R$^6$;
R$^2$ and R$^3$ are each independently H or C$_1$-C$_3$ alkyl; or
R$^2$ and R$^3$ together with the carbon atom to which they are attached, form a C$_3$-C$_6$ cycloalkyl ring;
R$^4$ and R$^5$ are each independently H or C$_1$-C$_3$ alkyl; or
R$^4$ and R$^5$ together with the carbon atom to which they are attached, form a C$_3$-C$_6$ cycloalkyl ring; and
each R$^6$ is independently C$_1$-C$_5$ alkyl, —C$_1$-C$_5$ alkylamino, —C$_1$-C$_5$ alkyl-NH—C$_1$-C$_3$ alkyl, —C$_1$-C$_5$ alkyl-N(C$_1$-C$_3$ alkyl)$_2$, —C$_1$-C$_5$ alkyl-phenyl, —C$_1$-C$_5$ alkyl-heteroaryl, —C$_1$-C$_5$ alkyl-tetrahydropyranyl, —C$_1$-C$_5$ alkyl-tetrahydrofuranyl, —C$_1$-C$_5$ alkyl-morpholinyl, C$_1$-C$_5$ alkoxyl, C$_3$-C$_8$ cycloalkyl, —C(O)NH$_2$, —C(O)NH—C$_1$-C$_5$ alkyl, —C(O)N(C$_1$-C$_5$ alky)$_2$, —C(O)NH—C$_3$-C$_8$ cycloalkyl, —C(O)OC$_1$-C$_5$ alkyl, halogen, cyano, phenyl, tetrahydropyranyl, tetrahydrofuranyl, piperidinyl, pyrrolodinyl, morpholinyl, thiomorpholinyl, phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl or quinolinyl; wherein each heteroaryl group of said R$^6$ is optionally independently substituted with 1 to 2 of C$_1$-C$_3$ alkyl;
or a pharmaceutically acceptable salt thereof.

The compound according to the embodiment described immediately above and wherein:
R$^1$ is phenyl, isoxazolyl, imidazolyl, pyrazolyl, thiazolyl, pyridinyl, benzimidazolyl, pyrazolopyridinyl or quinolinyl; wherein each of the foregoing R$^1$ groups optionally substituted with 1 to 3 substituents selected from R$^6$;
R$^2$ and R$^3$ are each independently H or C$_1$-C$_3$alkyl;
R$^4$ and R$^5$ are each independently H or C$_1$-C$_3$ alkyl; and
each R$^6$ is independently C$_1$-C$_5$ alkyl, —C$_1$-C$_5$ alkyl-N(C$_1$-C$_2$ alkyl)$_2$, —C$_1$-C$_3$ alkyl-phenyl, —C$_1$-C$_3$ alkyl-pyridinyl, —C$_1$-C$_3$ alkyl-tetrahydrofuranyl, —C$_1$-C$_3$ alkyl-morpholinyl, C$_3$-C$_6$ cycloalkyl, —C(O)NH$_2$, —C(O)NH—C$_1$-C$_3$ alkyl, —C(O)NH—C$_3$-C$_6$ cycloalkyl, —C(O)OC$_1$-C$_3$ alkyl, halogen, tetrahydropyranyl, phenyl, imidazolyl or thiazolyl; wherein each heteroaryl group of said R$^6$ is optionally independently substituted with 1 to 2 of C$_1$-C$_3$ alkyl;
or a pharmaceutically acceptable salt thereof.

The compound according to the embodiment described immediately above and wherein:
R$^1$ is phenyl, isoxazolyl, imidazolyl, pyrazolyl, pyridinyl, benzimidazolyl, pyrazolopyridinyl or quinolinyl; wherein each of the foregoing R$^1$ groups is optionally substituted with 1 to 3 substituents selected from R$^6$;
R$^2$ and R$^3$ are each independently H or methyl;
R$^4$ and R$^5$ are each independently H or methyl; and
each R$^6$ is independently C$_1$-C$_5$ alkyl, —C$_1$-C$_3$ alkyl-phenyl, —C$_1$-C$_3$ alkyl-pyridinyl, —C$_1$-C$_3$ alkyl-tetrahydrofuranyl, —C$_1$-C$_3$ alkyl-morpholinyl, —C(O)NH$_2$, —C(O)NH—C$_3$-C$_6$ cycloalkyl, halogen or tetrahydropyranyl;
or a pharmaceutically acceptable salt thereof.

The compound according to the embodiment described immediately above and wherein:
R$^1$ is phenyl, isoxazolyl, imidazolyl, pyrazolyl, pyridinyl, pyrazolopyridinyl or quinolinyl; wherein each of the foregoing R$^1$ groups is optionally substituted with 1 to 3 substituents selected from R$^6$; and
each R$^6$ is independently C$_1$-C$_5$ alkyl, —C$_1$-C$_3$ alkyl-phenyl, —C$_1$-C$_3$ alkyl-pyridinyl, —C$_1$-C$_3$ alkyl-tetrahydrofuranyl, —C$_1$-C$_3$ alkyl-morpholinyl, —C(O)NH$_2$, —C(O)NH—C$_3$-C$_6$ cycloalkyl or tetrahydropyranyl;
or a pharmaceutically acceptable salt thereof.

In one embodiment, the invention relates to a compound selected from those identified as Examples 1 to 105 in Table 1 below, and any combination thereof, and pharmaceutically acceptable salts thereof.

TABLE 1

| Example | Structure | Name |
|---|---|---|
| 1 | 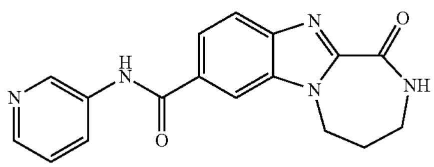 [SMILES: O=C(Nc1cccnc1)c1ccc2nc3n(c2c1)CCCNC3=O] | 1-oxo-N-(pyridin-3-yl)-2,3,4,5-tetrahydro-1H-[1,4]diazepino[1,2-a]benzimidazole-8-carboxamide |
| 2 | 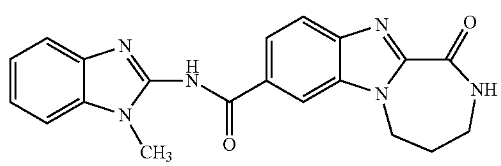 [SMILES: Cn1c(NC(=O)c2ccc3nc4n(c3c2)CCCNC4=O)nc2ccccc21] | N-(1-methyl-1H-benzimidazol-2-yl)-1-oxo-2,3,4,5-tetrahydro-1H-[1,4]diazepino[1,2-a]benzimidazole-8-carboxamide |
| 3 | 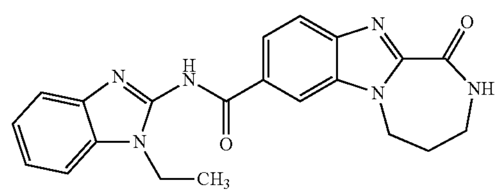 [SMILES: CCn1c(NC(=O)c2ccc3nc4n(c3c2)CCCNC4=O)nc2ccccc21] | N-(1-ethyl-1H-benzimidazol-2-yl)-1-oxo-2,3,4,5-tetrahydro-1H-[1,4]diazepino[1,2-a]benzimidazole-8-carboxamide |
| 4 | 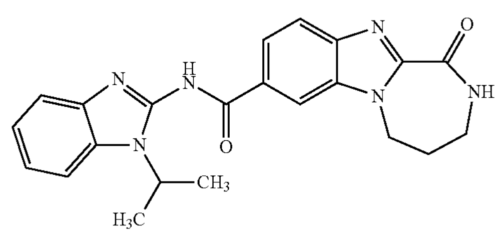 [SMILES: CC(C)n1c(NC(=O)c2ccc3nc4n(c3c2)CCCNC4=O)nc2ccccc21] | 1-oxo-N-[1-(propan-2-yl)-1H-benzimidazol-2-yl]-2,3,4,5-tetrahydro-1H-[1,4]diazepino[1,2-a]benzimidazole-8-carboxamide |
| 5 | 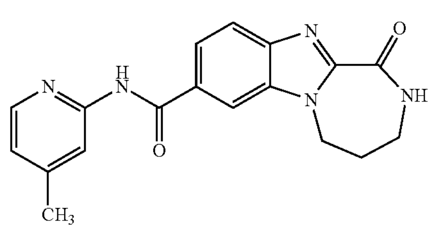 [SMILES: Cc1ccnc(NC(=O)c2ccc3nc4n(c3c2)CCCNC4=O)c1] | N-(4-methylpyridin-2-yl)-1-oxo-2,3,4,5-tetrahydro-1H-[1,4]diazepino[1,2-a]benzimidazole-8-carboxamide |

TABLE 1-continued

| Example | Structure | Name |
|---|---|---|
| 6 | 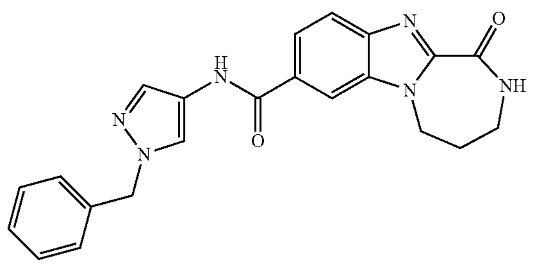 [SMILES: O=C(Nc1cnn(Cc2ccccc2)c1)c1ccc2nc3n(c2c1)CCCNC3=O] | N-(1-benzyl-1H-pyrazol-4-yl)-1-oxo-2,3,4,5-tetrahydro-1H-[1,4]diazepino[1,2-a]benzimidazole-8-carboxamide |
| 7 | 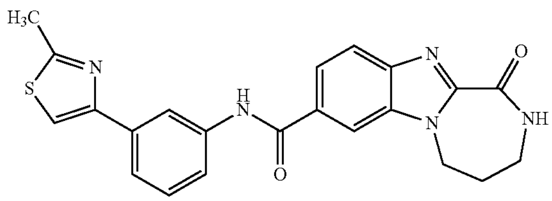 [SMILES: Cc1nc(-c2cccc(NC(=O)c3ccc4nc5n(c4c3)CCCNC5=O)c2)cs1] | N-[3-(2-methyl-1,3-thiazol-4-yl)phenyl]-1-oxo-2,3,4,5-tetrahydro-1H-[1,4]diazepino[1,2-a]benzimidazole-8-carboxamide |
| 8 | 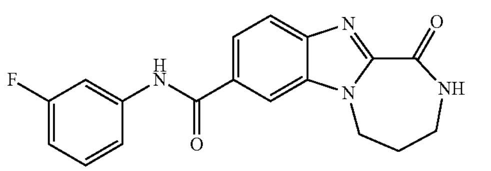 [SMILES: O=C(Nc1cccc(F)c1)c1ccc2nc3n(c2c1)CCCNC3=O] | N-(3-fluorophenyl)-1-oxo-2,3,4,5-tetrahydro-1H-[1,4]diazepino[1,2-a]benzimidazole-8-carboxamide |
| 9 | 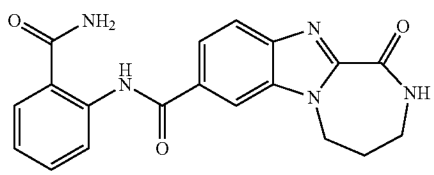 [SMILES: NC(=O)c1ccccc1NC(=O)c1ccc2nc3n(c2c1)CCCNC3=O] | N-(2-carbamoylphenyl)-1-oxo-2,3,4,5-tetrahydro-1H-[1,4]diazepino[1,2-a]benzimidazole-8-carboxamide |
| 10 | 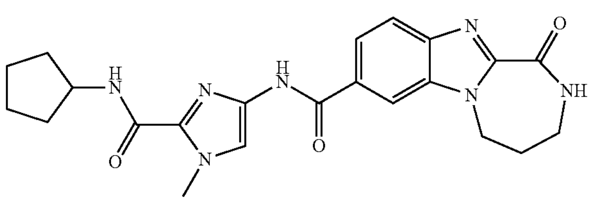 [SMILES: Cn1cc(NC(=O)c2ccc3nc4n(c3c2)CCCNC4=O)nc1C(=O)NC1CCCC1] | N-[2-(cyclopentylcarbamoyl)-1-methyl-1H-imidazol-4-yl]-1-oxo-2,3,4,5-tetrahydro-1H-[1,4]diazepino[1,2-a]benzimidazole-8-carboxamide |
| 11 | 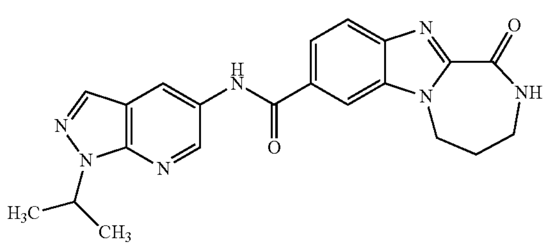 [SMILES: CC(C)n1ncc2cc(NC(=O)c3ccc4nc5n(c4c3)CCCNC5=O)cnc21] | 1-oxo-N-[1-(propan-2-yl)-1H-pyrazolo[3,4-b]pyridin-5-yl]-2,3,4,5-tetrahydro-1H-[1,4]diazepino[1,2-a]benzimidazole-8-carboxamide |
| 12 | 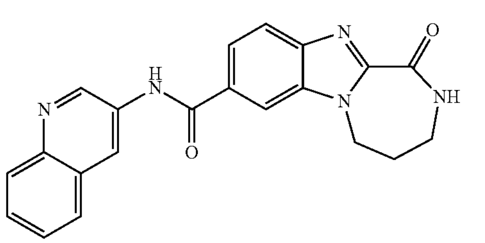 [SMILES: O=C(Nc1cnc2ccccc2c1)c1ccc2nc3n(c2c1)CCCNC3=O] | 1-oxo-N-(quinolin-3-yl)-2,3,4,5-tetrahydro-1H-[1,4]diazepino[1,2-a]benzimidazole-8-carboxamide |

TABLE 1-continued

| Example | Structure | Name |
|---|---|---|
| 13 | 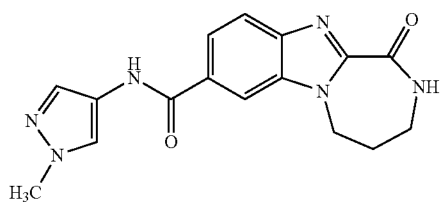 [SMILES: Cn1cc(NC(=O)c2ccc3nc4n(c3c2)CCCNC4=O)cn1] | N-(1-methyl-1H-pyrazol-4-yl)-1-oxo-2,3,4,5-tetrahydro-1H-[1,4]diazepino[1,2-a]benzimidazole-8-carboxamide |
| 14 | 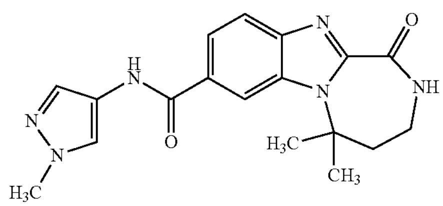 [SMILES: Cn1cc(NC(=O)c2ccc3nc4n(c3c2)C(C)(C)CCNC4=O)cn1] | 5,5-dimethyl-N-(1-methyl-1H-pyrazol-4-yl)-1-oxo-2,3,4,5-tetrahydro-1H-[1,4]diazepino[1,2-a]benzimidazole-8-carboxamide |
| 15 | 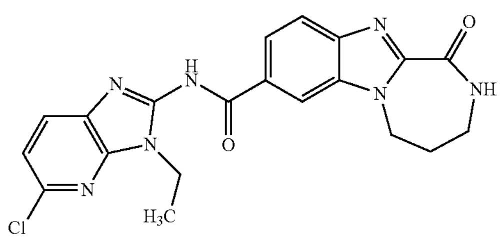 [SMILES: CCn1c(NC(=O)c2ccc3nc4n(c3c2)CCCNC4=O)nc2ccc(Cl)nc21] | N-(5-chloro-3-ethyl-3H-imidazo[4,5-b]pyridin-2-yl)-1-oxo-2,3,4,5-tetrahydro-1H-[1,4]diazepino[1,2-a]benzimidazole-8-carboxamide |
| 16 | 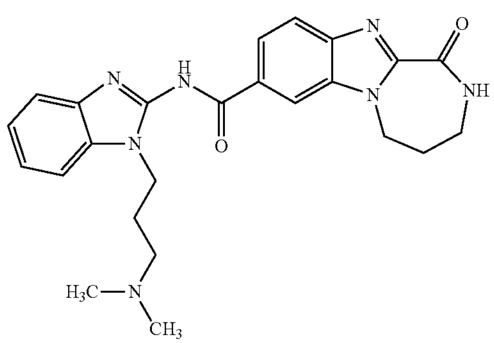 [SMILES: CN(C)CCCn1c(NC(=O)c2ccc3nc4n(c3c2)CCCNC4=O)nc2ccccc21] | N-{1-[3-(dimethylamino)propyl]-1H-benzimidazol-2-yl}-1-oxo-2,3,4,5-tetrahydro-1H-[1,4]diazepino[1,2-a]benzimidazole-8-carboxamide |
| 17 | 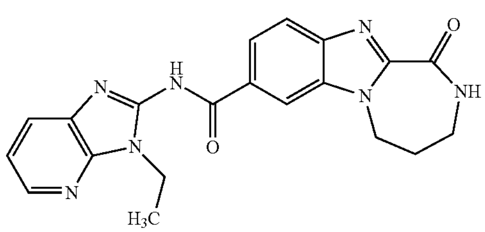 [SMILES: CCn1c(NC(=O)c2ccc3nc4n(c3c2)CCCNC4=O)nc2cccnc21] | N-(3-ethyl-3H-imidazol[4,5-b]pyridin-2-yl)-1-oxo-2,3,4,5-tetrahydro-1H-[1,4]diazepino[1,2-a]benzimidazole-8-carboxamide |
| 18 | 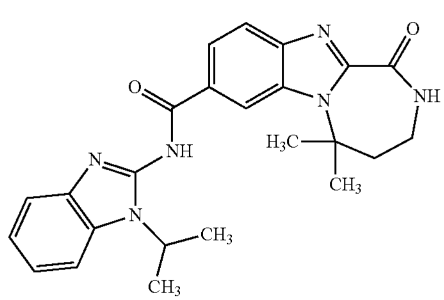 [SMILES: CC(C)n1c(NC(=O)c2ccc3nc4n(c3c2)C(C)(C)CCNC4=O)nc2ccccc21] | 5,5-dimethyl-1-oxo-N-[1-(propan-2-yl)-1H-benzimidazol-2-yl]-2,3,4,5-tetrahydro-1H-[1,4]diazepino[1,2-a]benzimidazole-8-carboxamide |

TABLE 1-continued

| Example | Structure | Name |
|---|---|---|
| 19 | 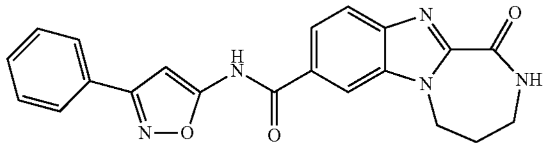 [SMILES: O=C(Nc1cc(-c2ccccc2)no1)c1ccc2nc3n(c2c1)CCCNC3=O] | 1-oxo-N-(3-phenyl-1,2-oxazol-5-yl)-2,3,4,5-tetrahydro-1H-[1,4]diazepino[1,2-a]benzimidazole-8-carboxamide |
| 20 | 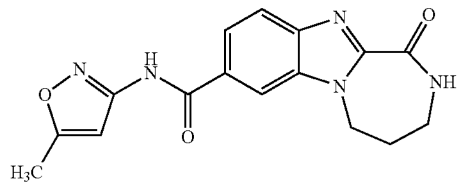 [SMILES: Cc1cc(NC(=O)c2ccc3nc4n(c3c2)CCCNC4=O)no1] | N-(5-methyl-1,2-oxazol-3-yl)-1-oxo-2,3,4,5-tetrahydro-1H-[1,4]diazepino[1,2-a]benzimidazole-8-carboxamide |
| 21 | 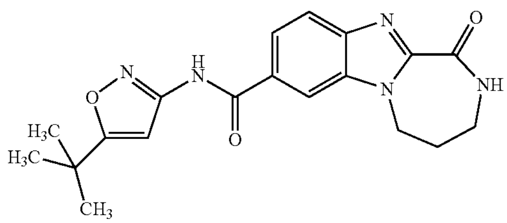 [SMILES: CC(C)(C)c1cc(NC(=O)c2ccc3nc4n(c3c2)CCCNC4=O)no1] | N-(5-tert-butyl-1,2-oxazol-3-yl)-1-oxo-2,3,4,5-tetrahydro-1H-[1,4]diazepino[1,2-a]benzimidazole-8-carboxamide |
| 22 | 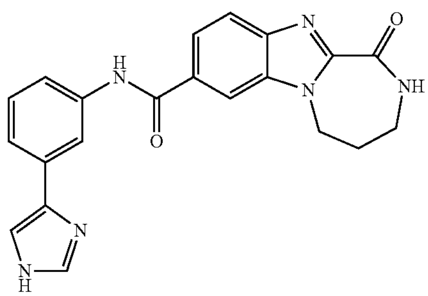 [SMILES: O=C(Nc1cccc(-c2c[nH]cn2)c1)c1ccc2nc3n(c2c1)CCCNC3=O] | N-[3-(1H-imidazol-4-yl)phenyl]-1-oxo-2,3,4,5-tetrahydro-1H-[1,4]diazepino[1,2-a]benzimidazole-8-carboxamide |
| 23 | 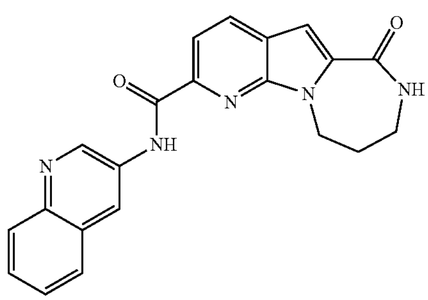 [SMILES: O=C(Nc1cnc2ccccc2c1)c1ccc2cc3n(c2n1)CCCNC3=O] | 6-oxo-N-(quinolin-3-yl)-7,8,9,10-tetrahydro-6H-pyrido[3',2':4,5]pyrrolo[1,2-a][1,4]diazepine-2-carboxamide |
| 24 | 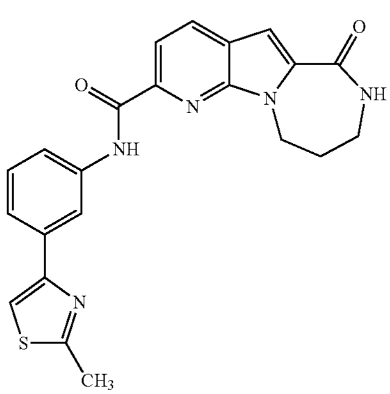 [SMILES: Cc1nc(-c2cccc(NC(=O)c3ccc4cc5n(c4n3)CCCNC5=O)c2)cs1] | N-[3-(2-methyl-1,3-triazol-4-yl)phenyl]-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 25 | 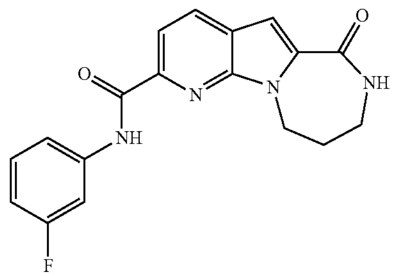 [SMILES: O=C(Nc1cccc(F)c1)c1ccc2cc3n(c2n1)CCCNC3=O] | N-(3-fluorophenyl)-6-oxo-7,8,9,10-tetrahydro-6H-pyrido[3',2':4,5]pyrrolo[1,2-a][1,4]diazepine-2-carboxamide |
| 26 | 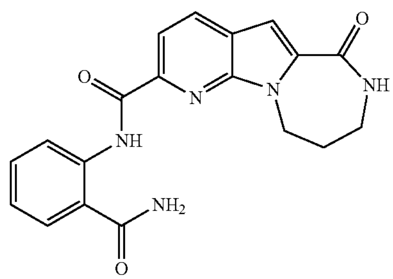 [SMILES: NC(=O)c1ccccc1NC(=O)c1ccc2cc3n(c2n1)CCCNC3=O] | N-(2-carbamoylphenyl)-6-oxo-7,8,9,10-tetrahydro-6H-pyrido[3',2':4,5]pyrrolo[1,2-a][1,4]diazepine-2-carboxamide |
| 27 | 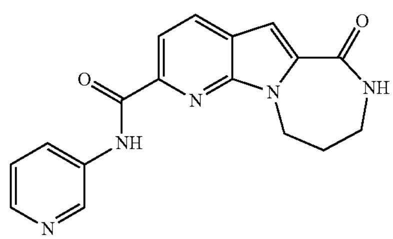 [SMILES: O=C(Nc1cccnc1)c1ccc2cc3n(c2n1)CCCNC3=O] | 6-oxo-N-(pyridin-3-yl)-7,8,9,10-tetrahydro-6H-pyrido[3',2':4,5]pyrrolo[1,2-a][1,4]diazepine-2-carboxamide |
| 28 | 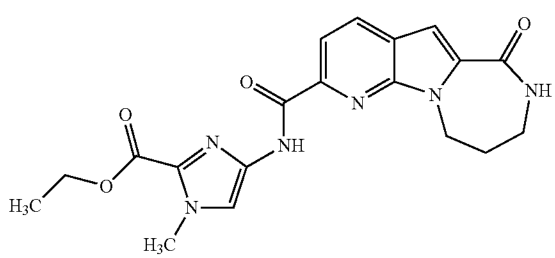 [SMILES: CCOC(=O)c1nc(NC(=O)c2ccc3cc4n(c3n2)CCCNC4=O)cn1C] | ethyl 1-methyl-4-{[(6-oxo-7,8,9,10-tetrahydro-6H-pyrido[3',2':4,5]pyrrolo[1,2-a][1,4]diazepin-2-yl)carbonyl]amino}-1H-imidazole-2-carboxylate |
| 29 | 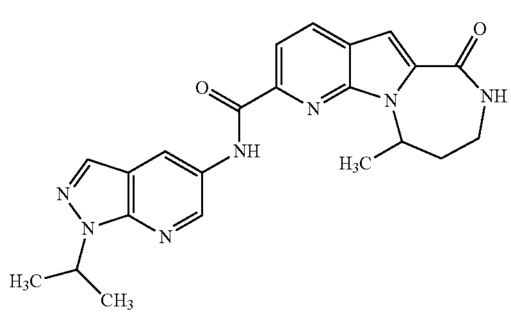 [SMILES: CC(C)n1ncc2cc(NC(=O)c3ccc4cc5n(c4n3)C(C)CCNC5=O)cnc21] | 10-methyl-6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 30 | 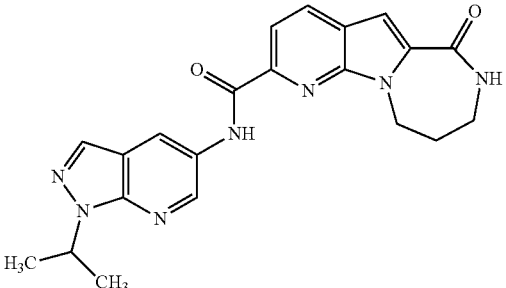 | 6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 31 | 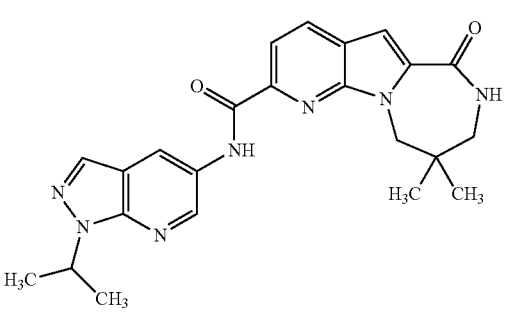 [SMILES: CC(C)n1ncc2cc(NC(=O)c3ccc4cc5n(c4n3)CC(C)(C)CNC5=O)cnc21] | 9,9-dimethyl-6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 32 | 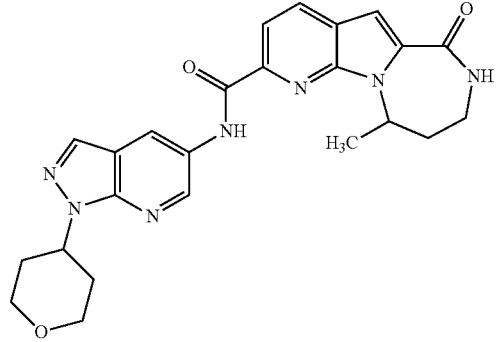 [SMILES: CC1CCNC(=O)c2cc3ccc(C(=O)Nc4cnc5c(cnn5C5CCOCC5)c4)nc3n21] | 10-methyl-6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 33 | 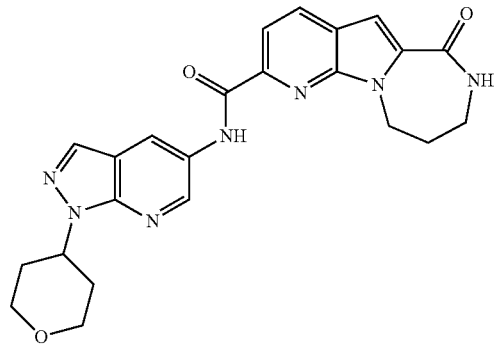 [SMILES: O=C(Nc1cnc2c(cnn2C2CCOCC2)c1)c1ccc2cc3n(c2n1)CCCNC3=O] | 6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 34 | 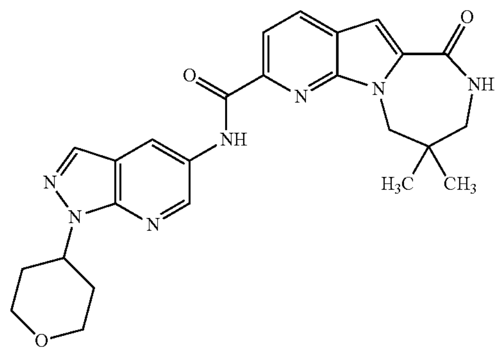 [SMILES: CC1(C)CNC(=O)c2cc3ccc(C(=O)Nc4cnc5c(cnn5C5CCOCC5)c4)nc3n2C1] | 9,9-dimethyl-6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 35 | 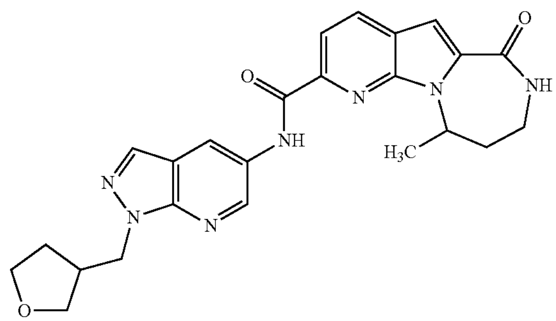 [SMILES: CC1CCNC(=O)c2cc3ccc(C(=O)Nc4cnc5c(cnn5CC5CCOC5)c4)nc3n21] | 10-methyl-6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 36 | 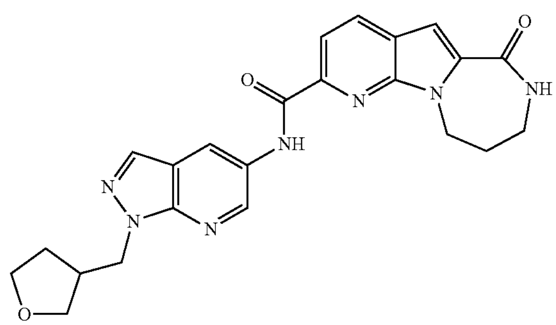 [SMILES: O=C(Nc1cnc2c(cnn2CC2CCOC2)c1)c1ccc2cc3n(c2n1)CCCNC3=O] | 6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 37 | 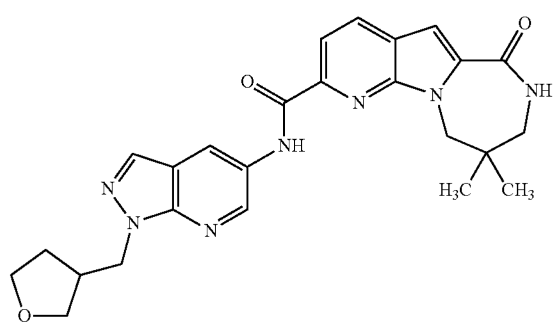 [SMILES: CC1(C)CNC(=O)c2cc3ccc(C(=O)Nc4cnc5c(cnn5CC5CCOC5)c4)nc3n2C1] | 9,9-dimethyl-6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide |
| 38 | 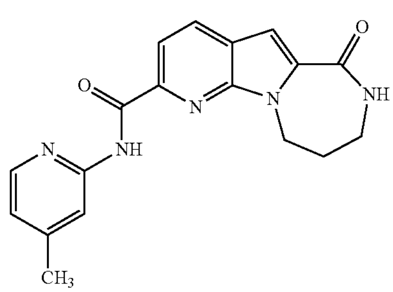 [SMILES: Cc1ccnc(NC(=O)c2ccc3cc4n(c3n2)CCCNC4=O)c1] | N-(4-methylpyridin-2-yl)-6-oxo-7,8,9,10-tetrahydro-6H-pyrido[3',2':4,5]pyrrolo[1,2-a][1,4]diazepine-2-carboxamide |

TABLE 1-continued

| Example | Name |
|---|---|
| 39 | 9,9-dimethyl-6-oxo-N-(quinolin-3-yl)-7,8,9,10-tetrahydro-6H-pyrido[3',2':4,5]pyrrolo[1,2-a][1,4]diazepine-2-carboxamide |
| 40 | 10-methyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide |
| 41 | N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide |
| 42 | 9,9-dimethyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide |
| 43 | N-(1-tert-butyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide |
| 44 | N-(1-tert-butyl-1H-pyrazol-4-yl)-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 45 | 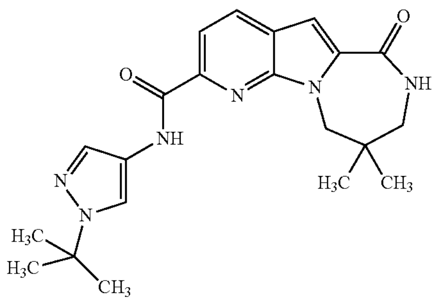 [SMILES: CC1(C)CNC(=O)c2cc3ccc(C(=O)Nc4cnn(C(C)(C)C)c4)nc3n2C1] | N-(1-tert-butyl-1H-pyrazol-4-yl)-9,9-dimethyl-6-oxo-7,8,9,10-tetrahydro-6H-pyrido[3',2':4,5]pyrrolo[1,2-a][1,4]diazepine-2-carboxamide |
| 46 | 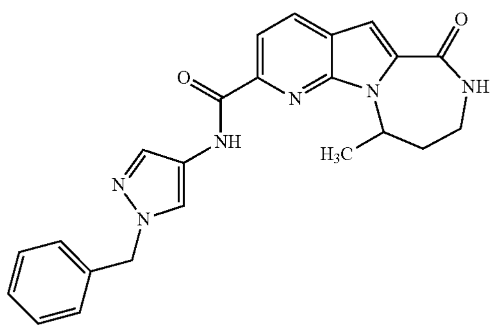 [SMILES: CC1CCNC(=O)c2cc3ccc(C(=O)Nc4cnn(Cc5ccccc5)c4)nc3n21] | N-(1-benzyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide |
| 47 | 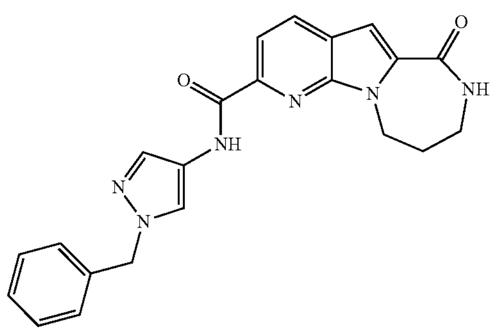 [SMILES: O=C(Nc1cnn(Cc2ccccc2)c1)c1ccc2cc3n(c2n1)CCCNC3=O] | N-(1-benzyl-1H-pyrazol-4-yl)-6-oxo-7,8,9,10-tetrahydro-6H-pyrido[3',2':4,5]pyrrolo[1,2-a][1,4]diazepine-2-carboxamide |
| 48 | 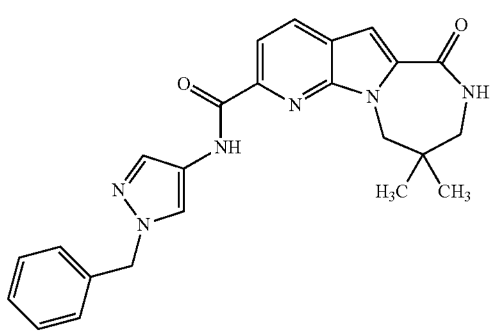 [SMILES: CC1(C)CNC(=O)c2cc3ccc(C(=O)Nc4cnn(Cc5ccccc5)c4)nc3n2C1] | N-(1-benzyl-1H-pyrazol-4-yl)-9,9-dimethyl-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 49 | 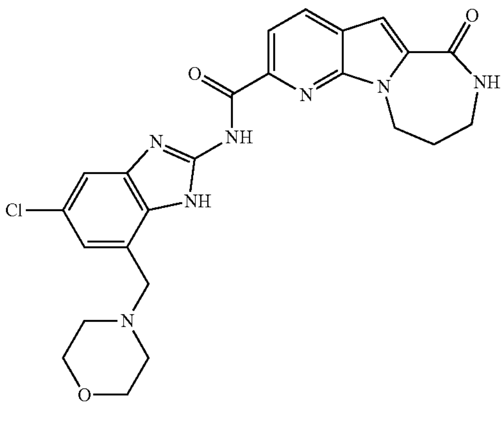 [SMILES: O=C(Nc1nc2cc(Cl)cc(CN3CCOCC3)c2[nH]1)c1ccc2cc3n(c2n1)CCCNC3=O] | N-[5-chloro-7-(morpholin-4-ylmethyl)-1H-benzimidazol-2-yl]-6-oxo-7,8,9,10-tetrahydro-6H-pyrido[3',2':4,5]pyrrolo[1,2-a][1,4]diazepine-2-carboxamide |
| 50 | 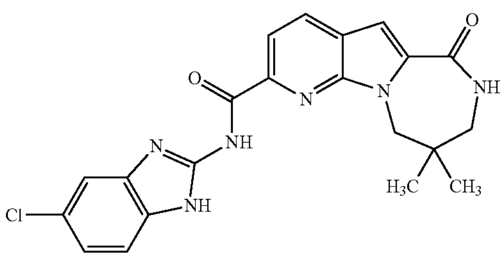 [SMILES: CC1(C)CNC(=O)c2cc3ccc(C(=O)Nc4nc5cc(Cl)ccc5[nH]4)nc3n2C1] | N-(5-chloro-1H-benzimidazol-2-yl)-9,9-dimethyl-6-oxo-7,8,9,10-tetrahydro-6H-pyrido[3',2':4,5]pyrrolo[1,2-a][1,4]diazepine-2-carboxamide |
| 51 | 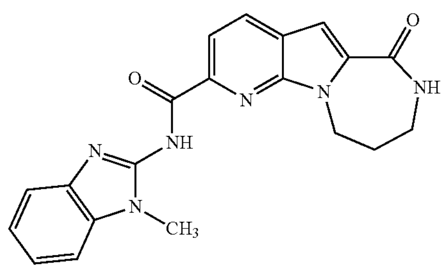 [SMILES: Cn1c(NC(=O)c2ccc3cc4n(c3n2)CCCNC4=O)nc2ccccc21] | N-(1-methyl-1H-benzimidazol-2-yl)-6-oxo-7,8,9,10-tetrahydro-6H-pyrido[3',2':4,5]pyrrolo[1,2-a][1,4]diazepine-2-carboxamide |
| 52 | 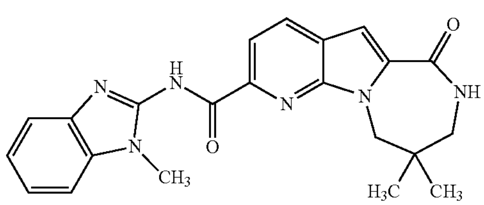 [SMILES: Cn1c(NC(=O)c2ccc3cc4n(c3n2)CC(C)(C)CNC4=O)nc2ccccc21] | 9,9-dimethyl-N-(1-methyl-1H-benzimidazol-2-yl)-6-oxo-7,8,9,10-tetrahydro-6H-pyrido[3',2':4,5]pyrrolo[1,2-a][1,4]diazepine-2-carboxamide |
| 53 | 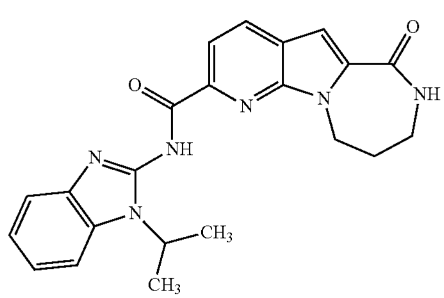 [SMILES: CC(C)n1c(NC(=O)c2ccc3cc4n(c3n2)CCCNC4=O)nc2ccccc21] | 6-oxo-N-[1-(propan-2-yl)-1H-benzimidazol-2-yl]-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 54 | 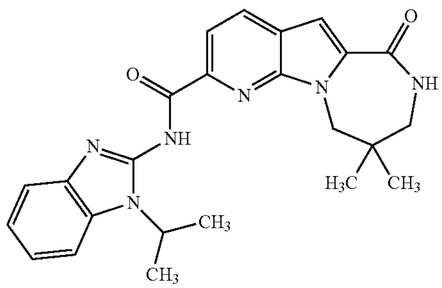 [SMILES: CC(C)n1c(NC(=O)c2ccc3cc4n(c3n2)CC(C)(C)CNC4=O)nc2ccccc21] | 9,9-dimethyl-6-oxo-N-[1-(propan-2-yl)-1H-benzimidazol-2-yl]-7,8,9,10-tetrahydro-6H-pyrido[3',2':4,5]pyrrolo[1,2-a][1,4]diazepine-2-carboxamide |
| 55 | 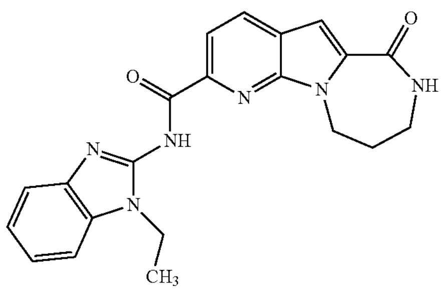 [SMILES: CCn1c(NC(=O)c2ccc3cc4n(c3n2)CCCNC4=O)nc2ccccc21] | N-(1-ethyl-1H-benzimidazol-2-yl)-6-oxo-7,8,9,10-tetrahydro-6H-pyrido[3',2':4,5]pyrrolo[1,2-a][1,4]diazepine-2-carboxamide |
| 56 | 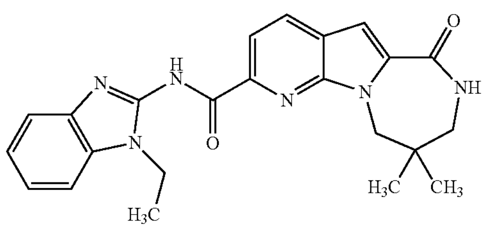 [SMILES: CCn1c(NC(=O)c2ccc3cc4n(c3n2)CC(C)(C)CNC4=O)nc2ccccc21] | N-(1-ethyl-1H-benzimidazol-2-yl)-9,9-dimethyl-6-oxo-7,8,9,10-tetrahydro-6H-pyrido[3',2':4,5]pyrrolo[1,2-a][1,4]diazepine-2-carboxamide |
| 57 | 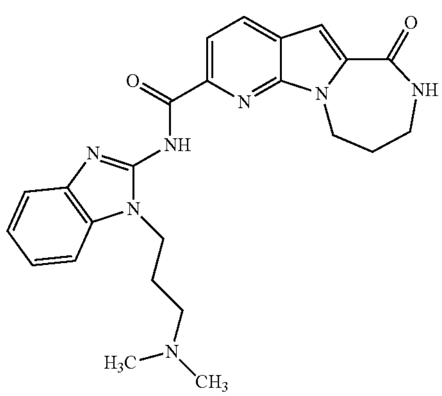 [SMILES: CN(C)CCCn1c(NC(=O)c2ccc3cc4n(c3n2)CCCNC4=O)nc2ccccc21] | N-{1-[3-(dimethylamino)propyl]-1H-benzimidazol-2-yl}-6-oxo-7,8,9,10-tetrahydro-6H-pyrido[3',2':4,5]pyrrolo[1,2-a][1,4]diazepine-2-carboxamide |
| 58 | 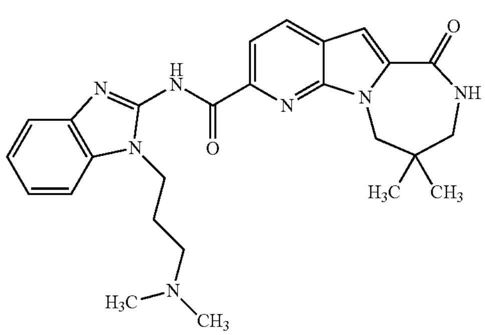 [SMILES: CN(C)CCCn1c(NC(=O)c2ccc3cc4n(c3n2)CC(C)(C)CNC4=O)nc2ccccc21] | N-{1-[3-(dimethylamino)propyl]-1H-benzimidazol-2-yl}-9,9-dimethyl-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 59 | 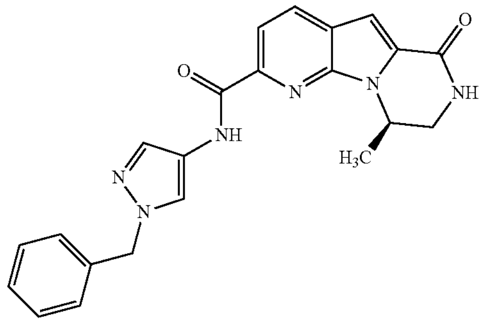 [SMILES: C[C@@H]1CNC(=O)c2cc3ccc(C(=O)Nc4cnn(Cc5ccccc5)c4)nc3n21] | (9R)-N-(1-benzyl-1H-pyrazol-4-yl)-9-methyl-6-oxo-6,7,8,9-tetrahydropyrido[3',2':4,5]pyrrolo[1,2-a]pyrazine-2-carboxamide |
| 60 | 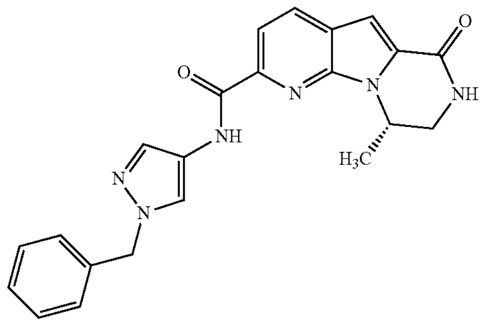 [SMILES: C[C@H]1CNC(=O)c2cc3ccc(C(=O)Nc4cnn(Cc5ccccc5)c4)nc3n21] | (9S)-N-(1-benzyl-1H-pyrazol-4-yl)-9-methyl-6-oxo-6,7,8,9-tetrahydropyrido[3',2':4,5]pyrrolo[1,2-a]pyrazine-2-carboxamide |
| 61 | 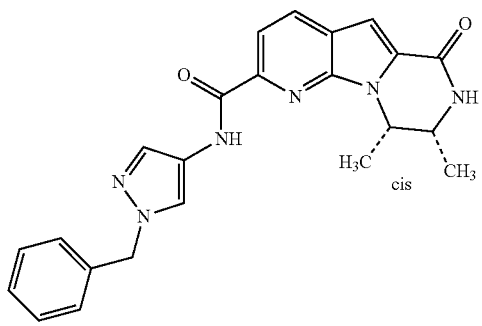 [SMILES: C[C@H]1NC(=O)c2cc3ccc(C(=O)Nc4cnn(Cc5ccccc5)c4)nc3n2[C@H]1C] | N-(1-benzyl-1H-pyrazol-4-yl)-cis-8,9-dimethyl-6-oxo-6,7,8,9-tetrahydropyrido[3',2':4,5]pyrrolo[1,2-a]pyrazine-2-carboxamide |
| 62 | 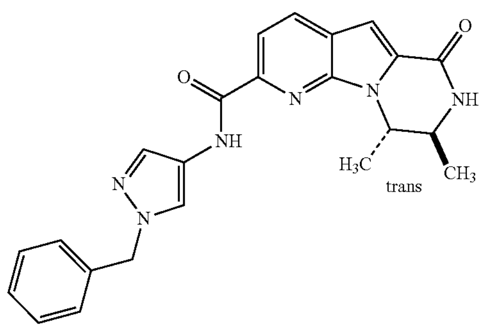 [SMILES: C[C@@H]1NC(=O)c2cc3ccc(C(=O)Nc4cnn(Cc5ccccc5)c4)nc3n2[C@H]1C] | N-(1-benzyl-1H-pyrazol-4-yl)-trans-8,9-dimethyl-6-oxo-6,7,8,9-tetrahydropyrido[3',2':4,5]pyrrolo[1,2-a]pyrazine-2-carboxamide |

TABLE 1-continued

| Example | Structure | Name |
|---|---|---|
| 63 | 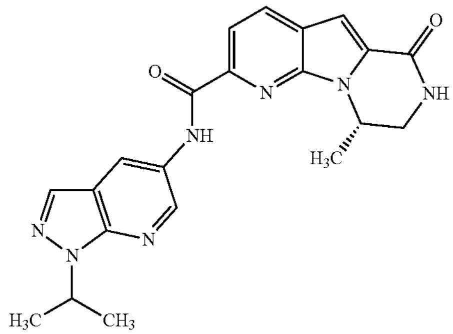 [SMILES: CC(C)n1ncc2cc(NC(=O)c3ccc4cc5n(c4n3)[C@@H](C)CNC5=O)cnc21] | (9S)-9-methyl-6-oxo-N-[1-(propan-2-yl)-1H-pyrazolo[3,4-b]pyridin-5-yl]-6,7,8,9-tetrahydropyrido[3',2':4,5]pyrrolo[1,2-a]pyrazine-2-carboxamide |
| 64 | 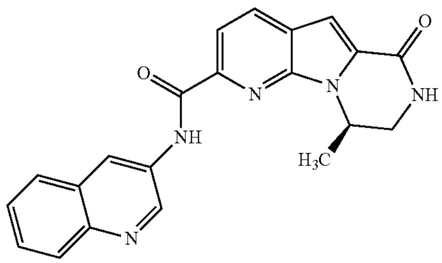 [SMILES: C[C@@H]1CNC(=O)c2cc3ccc(C(=O)Nc4cnc5ccccc5c4)nc3n21] | (9R)-9-methyl-6-oxo-N-(quinolin-3-yl)-6,7,8,9-tetrahydropyrido[3',2':4,5]pyrrolo[1,2-a]pyrazine-2-carboxamide |
| 65 | 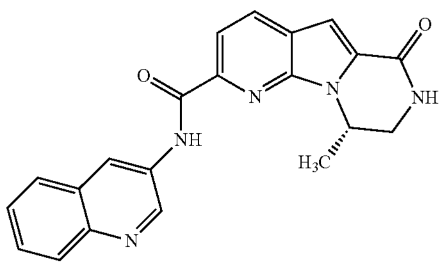 [SMILES: C[C@H]1CNC(=O)c2cc3ccc(C(=O)Nc4cnc5ccccc5c4)nc3n21] | (9S)-9-methyl-6-oxo-N-(quinolin-3-yl)-6,7,8,9-tetrahydropyrido[3',2':4,5]pyrrolo[1,2-a]pyrazine-2-carboxamide |
| 66 | 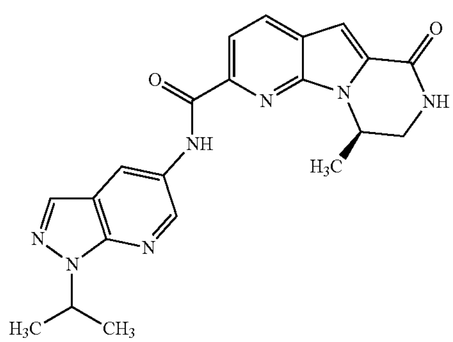 [SMILES: CC(C)n1ncc2cc(NC(=O)c3ccc4cc5n(c4n3)[C@H](C)CNC5=O)cnc21] | (9R)-9-methyl-6-oxo-N-[1-(propan-2-yl)-1H-pyrazolo[3,4-b]pyridin-5-yl]-6,7,8,9-tetrahydropyrido[3',2':4,5]pyrrolo[1,2-a]pyrazine-2-carboxamide |
| 67 | 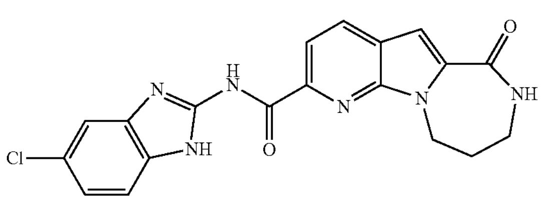 [SMILES: O=C(Nc1nc2cc(Cl)ccc2[nH]1)c1ccc2cc3n(c2n1)CCCNC3=O] | N-(5-chloro-1H-benzimidazol-2-yl)-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 68 | 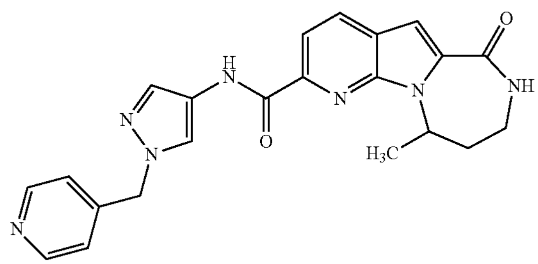 [SMILES: CC1CCNC(=O)c2cc3ccc(C(=O)Nc4cnn(Cc5ccncc5)c4)nc3n21] | 10-methyl-6-oxo-N-[1-(pyridin-4-ylmethyl)-1H-pyrazol-4-yl]-7,8,9,10-tetrahydro-6H-pyrido[3',2':4,5]pyrrolo[1,2-a][1,4]diazepine-2-carboxamide |
| 69 | 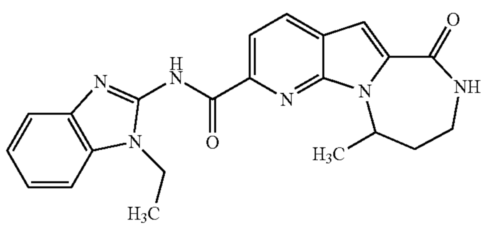 [SMILES: CCn1c(NC(=O)c2ccc3cc4n(c3n2)C(C)CCNC4=O)nc2ccccc21] | N-(1-ethyl-1H-benzimidazol-2-yl)-10-methyl-6-oxo-7,8,9,10-tetrahydro-6H-pyrido[3',2':4,5]pyrrolo[1,2-a][1,4]diazepine-2-carboxamide |
| 70 | 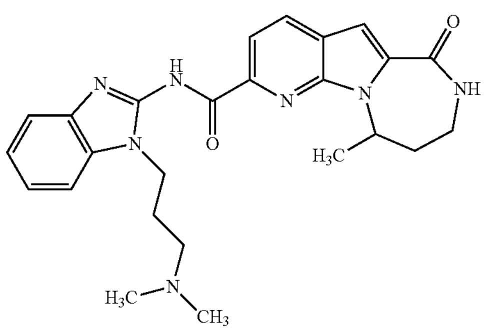 [SMILES: CC1CCNC(=O)c2cc3ccc(C(=O)Nc4nc5ccccc5n4CCCN(C)C)nc3n21] | N-{[3-(dimethylamino)propyl]-1H-benzimidazol-2-yl}-10-methyl-6-oxo-7,8,9,10-tetrahydro-6H-pyrido[3',2':4,5]pyrrolo[1,2-a][1,4]diazepine-2-carboxamide |
| 71 | 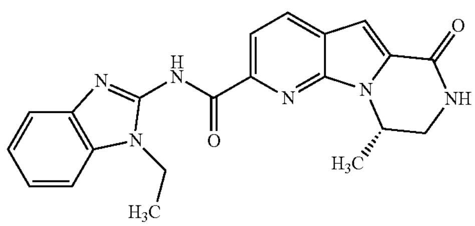 [SMILES: CCn1c(NC(=O)c2ccc3cc4n(c3n2)[C@@H](C)CNC4=O)nc2ccccc21] | (9S)-N-(1-ethyl-1H-benzimidazol-2-yl)-9-methyl-6-oxo-6,7,8,9-tetrahydropyrido[3',2':4,5]pyrrolo[1,2-a]pyrazine-2-carboxamide |
| 72 | 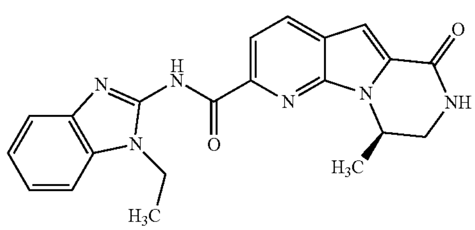 [SMILES: CCn1c(NC(=O)c2ccc3cc4n(c3n2)[C@H](C)CNC4=O)nc2ccccc21] | (9R)-N-(1-ethyl-1H-benzimidazol-2-yl)-9-methyl-6-oxo-6,7,8,9-tetrahydropyrido[3',2':4,5]pyrrolo[1,2-a]pyrazine-2-carboxamide |
| 73 | 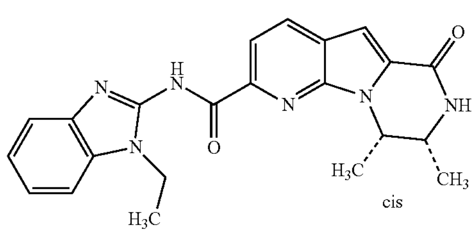 [SMILES: CCn1c(NC(=O)c2ccc3cc4n(c3n2)[C@@H](C)[C@@H](C)NC4=O)nc2ccccc21] | N-(1-ethyl-1H-benzimidazol-2-yl)-cis-8,9-dimethyl-6-oxo-6,7,8,9-tetrahydropyrido[3',2':4,5]pyrrolo[1,2-a]pyrazine-2-carboxamide |

TABLE 1-continued

| Example | Structure | Name |
|---|---|---|
| 74 | 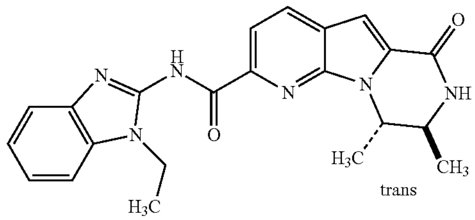 [SMILES: CCn1c(NC(=O)c2ccc3cc4n(c3n2)[C@@H](C)[C@H](C)NC4=O)nc2ccccc21] | N-(1-ethyl-1H-benzimidazol-2-yl)-trans-8,9-dimethyl-6-oxo-6,7,8,9-tetrahydropyrido[3',2':4,5]pyrrolo[1,2-a]pyrazine-2-carboxamide |
| 75 | 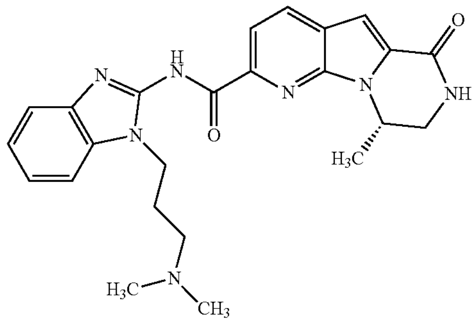 [SMILES: C[C@H]1CNC(=O)c2cc3ccc(C(=O)Nc4nc5ccccc5n4CCCN(C)C)nc3n21] | (9S)-N-{1-[3-(dimethylamino)propyl]-1H-benzimidazol-2-yl}-9-methyl-6-oxo-6,7,8,9-tetrahydropyrido[3',2':4,5]pyrrolo[1,2-a]pyrazine-2-carboxamide |
| 76 | 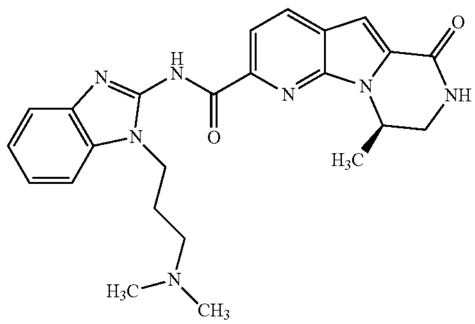 [SMILES: C[C@@H]1CNC(=O)c2cc3ccc(C(=O)Nc4nc5ccccc5n4CCCN(C)C)nc3n21] | (9R)-N-{1-[3-(dimethylamino)propyl]-1H-benzimidazol-2-yl}-9-methyl-6-oxo-6,7,8,9-tetrahydropyrido[3',2':4,5]pyrrolo[1,2-a]pyrazine-2-carboxamide |
| 77 | 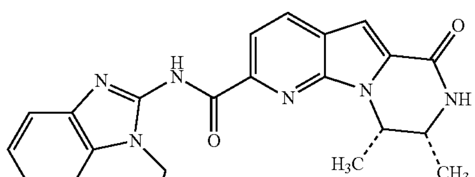 | N-{1-[3-(dimethylamino)propyl]-1H-benzimidazol-2-yl}-cis-8,9-dimethyl-6-oxo-6,7,8,9-tetrahydropyrido[3',2':4,5]pyrrolo[1,2-a]pyrazine-2-carboxamide |
| 78 | 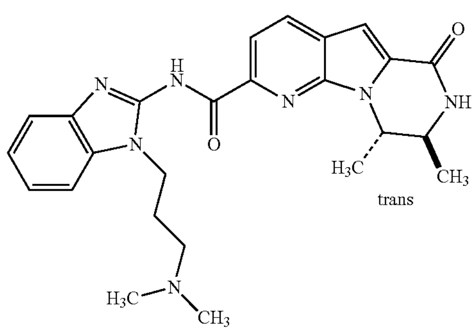 [SMILES: C[C@@H]1NC(=O)c2cc3ccc(C(=O)Nc4nc5ccccc5n4CCCN(C)C)nc3n2[C@H]1C] | N-{1-[3-(dimethylamino)propyl]-1H-benzimidazol-2-yl}-trans-8,9-dimethyl-6-oxo-6,7,8,9-tetrahydropyrido[3',2':4,5]pyrrolo[1,2-a]pyrazine-2-carboxamide |

TABLE 1-continued

| Example | Structure | Name |
|---|---|---|
| 79 | 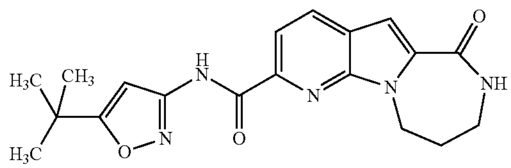 [SMILES: CC(C)(C)c1cc(NC(=O)c2ccc3cc4n(c3n2)CCCNC4=O)no1] | N-(5-tert-butyl-1,2-oxazol-3-yl)-6-oxo-7,8,9,10-tetrahydro-6H-pyrido[3',2':4,5]pyrrolo[1,2-a][1,4]diazepine-2-carboxamide |
| 80 | 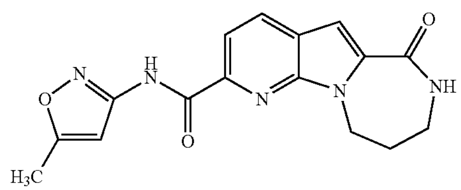 | N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide |
| 81 | 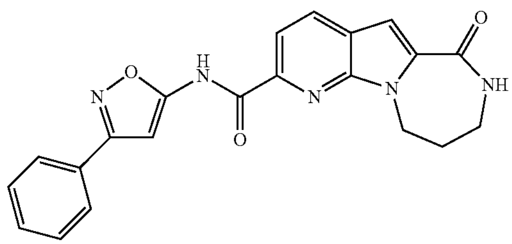 [SMILES: O=C(Nc1cc(-c2ccccc2)no1)c1ccc2cc3n(c2n1)CCCNC3=O] | 6-oxo-N-(3-phenyl-1,2-oxazol-5-yl)-7,8,9,10-tetrahydro-6H-pyrido[3',2':4,5]pyrrolo[1,2-a][1,4]diazepine-2-carboxamide |
| 82 | 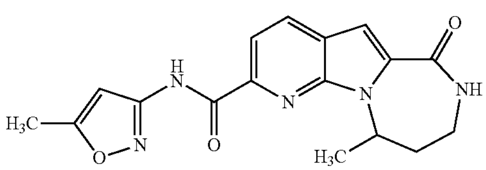 [SMILES: Cc1cc(NC(=O)c2ccc3cc4n(c3n2)C(C)CCNC4=O)no1] | 10-methyl-N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide |
| 83 | 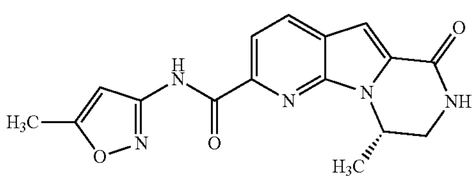 [SMILES: Cc1cc(NC(=O)c2ccc3cc4n(c3n2)[C@@H](C)CNC4=O)no1] | (9S)-9-methyl-N-(5-methyl-1,2-oxazol-3-yl)-6-oxo-6,7,8,9-tetrahydropyrido[3',2':4,5]pyrrolo[1,2-a]pyrazine-2-carboxamide |
| 84 | 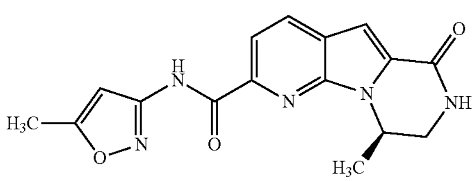 [SMILES: Cc1cc(NC(=O)c2ccc3cc4n(c3n2)[C@H](C)CNC4=O)no1] | (9R)-9-methyl-N-(5-methyl-1,2-oxazol-3-yl)-6-oxo-6,7,8,9-tetrahydropyrido[3',2':4,5]pyrrolo[1,2-a]pyrazine-2-carboxamide |
| 85 | 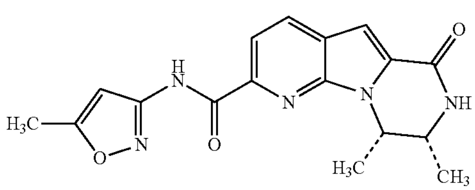 | Cis-8,9-dimethyl-N-(5-methyl-1,2-oxazol-3-yl)-6-oxo-6,7,8,9-tetrahydropyrido[3',2':4,5]pyrrolo[1,2-a]pyrazine-2-carboxamide |
| 86 | 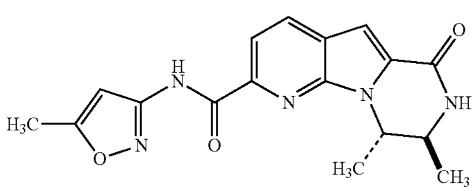 | Trans-8,9-dimethyl-N-(5-methyl-1,2-oxazol-3-yl)-6-oxo-6,7,8,9-tetrahydropyrido[3',2':4,5]pyrrolo[1,2-a]pyrazine-2-carboxamide |

TABLE 1-continued

| Example | Structure | Name |
|---|---|---|
| 87 | 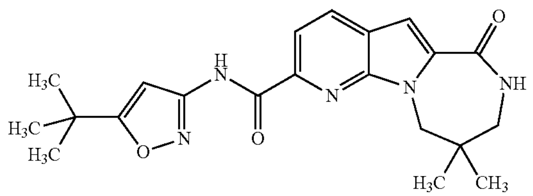 [SMILES: CC1(C)CNC(=O)c2cc3ccc(C(=O)Nc4cc(C(C)(C)C)on4)nc3n2C1] | N-(5-tert-butyl-1,2-oxazol-3-yl)-9,9-dimethyl-6-oxo-7,8,9,10-tetrahydro-6H-pyrido[3',2':4,5]pyrrolo[1,2-a][1,4]diazepine-2-carboxamide |
| 88 | 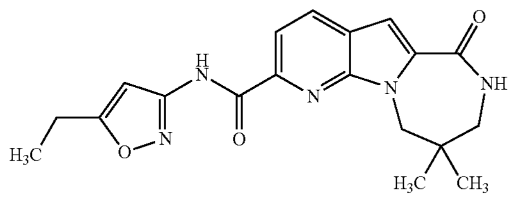 [SMILES: CCc1cc(NC(=O)c2ccc3cc4n(c3n2)CC(C)(C)CNC4=O)no1] | N-(5-ethyl-1,2-oxazol-3-yl)-9,9-dimethyl-6-oxo-7,8,9,10-tetrahydro-6H-pyrido[3',2':4,5]pyrrolo[1,2-a][1,4]diazepine-2-carboxamide |
| 89 | 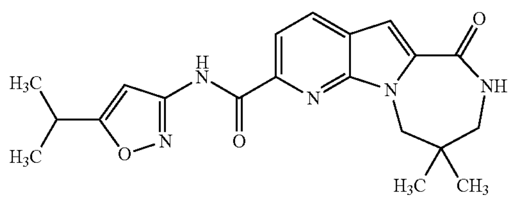 [SMILES: CC(C)c1cc(NC(=O)c2ccc3cc4n(c3n2)CC(C)(C)CNC4=O)no1] | 9,9-dimethyl-6-oxo-N-[5-(propan-2-yl)-1,2-oxazol-3-yl]-7,8,9,10-tetrahydro-6H-pyrido[3',2':4,5]pyrrolo[1,2-a][1,4]diazepine-2-carboxamide |
| 90 | 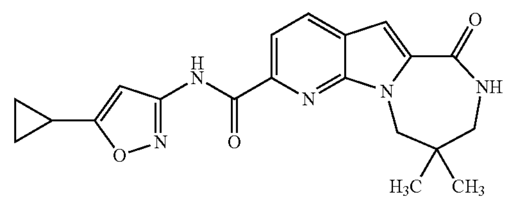 [SMILES: CC1(C)CNC(=O)c2cc3ccc(C(=O)Nc4cc(C5CC5)on4)nc3n2C1] | N-(5-cyclopropyl-1,2-oxazol-3-yl)-9,9-dimethyl-6-oxo-7,8,9,10-tetrahydro-6H-pyrido[3',2':4,5]pyrrolo[1,2-a][1,4]diazepine-2-carboxamide |
| 91 | 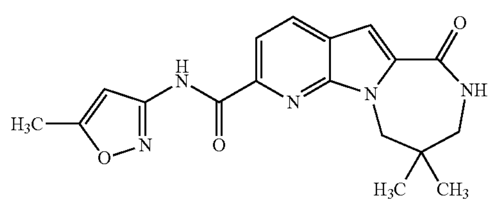 [SMILES: Cc1cc(NC(=O)c2ccc3cc4n(c3n2)CC(C)(C)CNC4=O)no1] | 9,9-dimethyl-N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide |
| 92 | 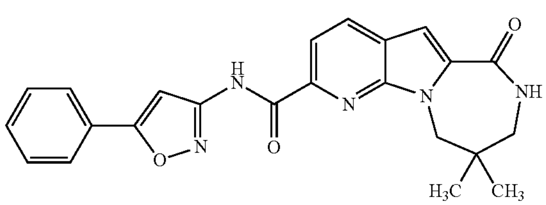 [SMILES: CC1(C)CNC(=O)c2cc3ccc(C(=O)Nc4cc(-c5ccccc5)on4)nc3n2C1] | 9,9-dimethyl-6-oxo-N-(5-phenyl-1,2-oxazol-3-yl)-7,8,9,10-tetrahydro-6H-pyrido[3',2':4,5]pyrrolo[1,2-a][1,4]diazepine-2-carboxamide |
| 93 | 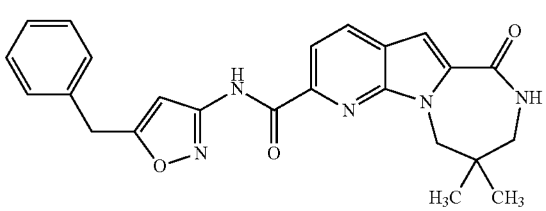 [SMILES: CC1(C)CNC(=O)c2cc3ccc(C(=O)Nc4cc(Cc5ccccc5)on4)nc3n2C1] | N-(5-benzyl-1,2-oxazol-3-yl)-9,9-dimethyl-6-oxo-7,8,9,10-tetrahydro-6H-pyrido[3',2':4,5]pyrrolo[1,2-a][1,4]diazepine-2-carboxamide |
| 94 | 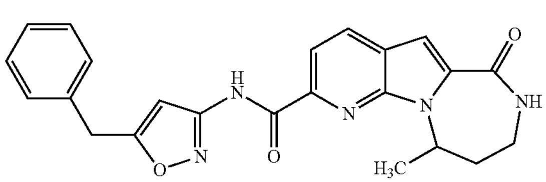 [SMILES: CC1CCNC(=O)c2cc3ccc(C(=O)Nc4cc(Cc5ccccc5)on4)nc3n21] | N-(5-benzyl-1,2-oxazol-3-yl)-10-methyl-6-oxo-7,8,9,10-tetrahydro-6H-pyrido[3',2':4,5]pyrrolo[1,2-a][1,4]diazepine-2-carboxamide |

TABLE 1-continued

| Example | Structure | Name |
|---|---|---|
| 95 | 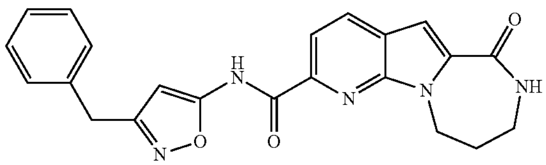 [SMILES: O=C(Nc1cc(Cc2ccccc2)no1)c1ccc2cc3n(c2n1)CCCNC3=O] | N-(3-benzyl-1,2-oxazol-5-yl)-6-oxo-7,8,9,10-tetrahydro-6H-pyrido[3',2':4,5]pyrrolo[1,2-a][1,4]diazepine-2-carboxamide |
| 96 | 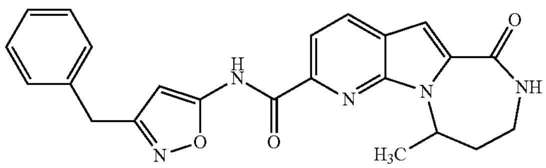 [SMILES: CC1CCNC(=O)c2cc3ccc(C(=O)Nc4cc(Cc5ccccc5)no4)nc3n21] | N-(3-benzyl-1,2-oxazol-5-yl)-10-methyl-6-oxo-7,8,9,10-tetrahydro-6H-pyrido[3',2':4,5]pyrrolo[1,2-a][1,4]diazepine-2-carboxamide |
| 97 | 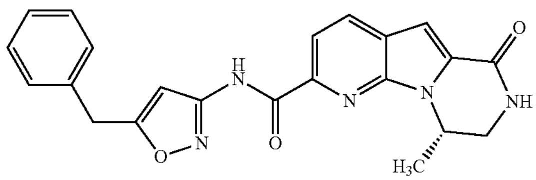 [SMILES: C[C@H]1CNC(=O)c2cc3ccc(C(=O)Nc4cc(Cc5ccccc5)on4)nc3n21] | (9S)-N-(5-benzyl-1,2-oxazol-3-yl)-9-methyl-6-oxo-6,7,8,9-tetrahydropyrido[3',2':4,5]pyrrolo[1,2-a]pyrazine-2-carboxamide |
| 98 | 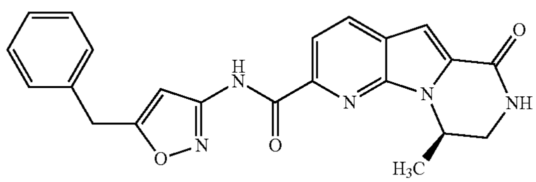 [SMILES: C[C@@H]1CNC(=O)c2cc3ccc(C(=O)Nc4cc(Cc5ccccc5)on4)nc3n21] | (9R)-N-(5-benzyl-1,2-oxazol-3-yl)-9-methyl-6-oxo-6,7,8,9-tetrahydropyrido[3',2':4,5]pyrrolo[1,2-a]pyrazine-2-carboxamide |
| 99 | 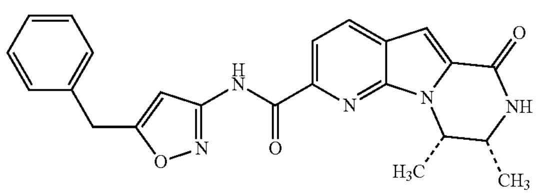 | N-(5-benzyl-1,2-oxazol-3-yl)-cis-8,9-dimethyl-6-oxo-6,7,8,9-tetrahydropyrido[3',2':4,5]pyrrolo[1,2-a]pyrazine-2-carboxamide |
| 100 | 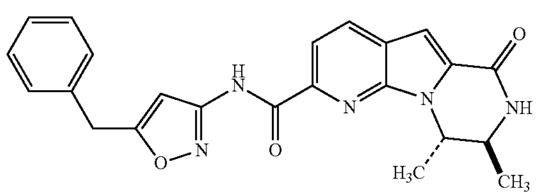 | N-(5-benzyl-1,2-oxazol-3-yl)-trans-8,9-dimethyl-6-oxo-6,7,8,9-tetrahydropyrido[3',2':4,5]pyrrolo[1,2-a]pyrazine-2-carboxamide |
| 101 | 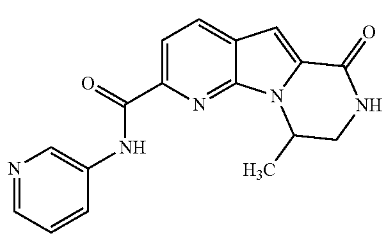 [SMILES: CC1CNC(=O)c2cc3ccc(C(=O)Nc4cccnc4)nc3n21] | 9-methyl-6-oxo-N-(pyridin-3-yl)-6,7,8,9-tetrahydropyrido[3',2':4,5]pyrrolo[1,2-a]pyrazine-2-carboxamide |

TABLE 1-continued

| Example | Structure | Name |
|---|---|---|
| 102 | 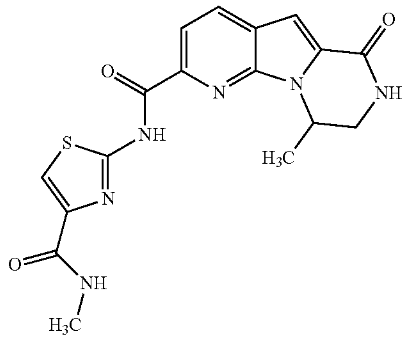 [SMILES: CNC(=O)c1csc(NC(=O)c2ccc3cc4n(c3n2)C(C)CNC4=O)n1] | 9-methyl-N-[4-(methylcarbamoyl)-1,3-thiazol-2-yl]-6-oxo-6,7,8,9-tetrahydropyrido[3',2':4,5]pyrrolo[1,2-a]pyrazine-2-carboxamide |
| 103 | 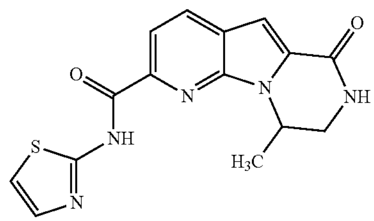 [SMILES: CC1CNC(=O)c2cc3ccc(C(=O)Nc4nccs4)nc3n21] | 9-methyl-6-oxo-N-(1,3-thiazol-2-yl)-6,7,8,9-tetrahydropyrido[3',2':4,5]pyrrolo[1,2-a]pyrazine-2-carboxamide |
| 104 | 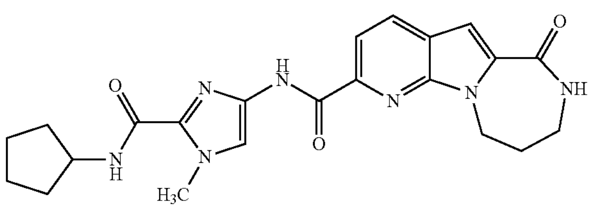 [SMILES: Cn1cc(NC(=O)c2ccc3cc4n(c3n2)CCCNC4=O)nc1C(=O)NC1CCCC1] | N-[2-(cyclopentylcarbamoyl)-1-methyl-1H-imidazol-4-yl]-6-oxo-7,8,9,10-tetrahydro-6H-pyrido[3',2':4,5]pyrrolo[1,2-a][1,4]diazepine-2-carboxamide |
| 105 | 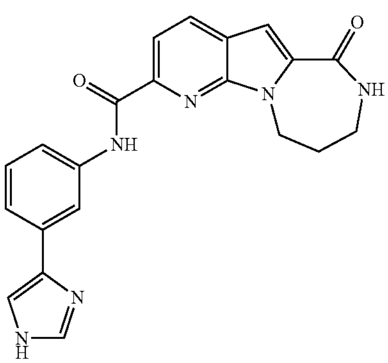 [SMILES: O=C(Nc1cccc(-c2c[nH]cn2)c1)c1ccc2cc3n(c2n1)CCCNC3=O] | N-[3-(1H-imidazol-4-yl)phenyl]-6-oxo-7,8,9,10-tetrahydro-6H-pyrido[3',2':4,5]pyrrolo[1,2-a][1,4]diazepine-2-carboxamide |

For all compounds disclosed hereinabove in this application, in the event the nomenclature is in conflict with the structure, it shall be understood that the compound is defined by the structure.

In one embodiment, the invention relates to a compound selected from consisting of:

10-methyl-6-oxo-N-[1-(pyridin-4-ylmethyl)-1H-pyrazol-4-yl]-7,8,9,10-tetrahydro-6H-pyrido[3',2':4,5]pyrrolo[1,2-a][1,4]diazepine-2-carboxamide;

N-(1-benzyl-1H-pyrazol-4-yl)-trans-8,9-dimethyl-6-oxo-6,7,8,9-tetrahydropyrido[3',2':4,5]pyrrolo[1,2-a]pyrazine-2-carboxamide;

(9R)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide;

N-(1-benzyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide;

(9S)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide;

(9R)-9-methyl-N-(5-methyl-1,2-oxazol-3-yl)-6-oxo-6,7,8,9-tetrahydropyrido[3',2':4,5]pyrrolo[1,2-a]pyrazine-2-carboxamide;

(9R)-9-methyl-6-oxo-N-[1-(propan-2-yl)-1H-pyrazolo[3,4-b]pyridin-5-yl]-6,7,8,9-tetrahydropyrido[3',2':4,5]pyrrolo[1,2-a]pyrazine-2-carboxamide;

(9R)-9-methyl-6-oxo-N-(quinolin-3-yl)-6,7,8,9-tetrahydropyrido[3',2':4,5]pyrrolo[1,2-a]pyrazine-2-carboxamide;

N-(2-carbamoylphenyl)-6-oxo-7,8,9,10-tetrahydro-6H-pyrido[3',2':4,5]pyrrolo[1,2-a][1,4]diazepine-2-carboxamide;

N-[2-(cyclopentylcarbamoyl)-1-methyl-1H-imidazol-4-yl]-6-oxo-7,8,9,10-tetrahydro-6H-pyrido[3',2':4,5]pyrrolo[1,2-a][1,4]diazepine-2-carboxamide;

N-(1-benzyl-1H-pyrazol-4-yl)-6-oxo-7,8,9,10-tetrahydro-6H-pyrido[3',2':4,5]pyrrolo[1,2-a][1,4]diazepine-2-carboxamide;
10-methyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide;
N-(1-tert-butyl-1H-pyrazol-4-yl)-6-oxo-7,8,9,10-tetrahydro-6H-pyrido[3',2':4,5]pyrrolo[1,2-a][1,4]diazepine-2-carboxamide;
N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide;
N-(1-tert-butyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide;
N-[5-chloro-7-(morpholin-4-ylmethyl)-1H-benzimidazol-2-yl]-6-oxo-7,8,9,10-tetrahydro-6H-pyrido[3',2':4,5]pyrrolo[1,2-a][1,4]diazepine-2-carboxamide;
N-(5-benzyl-1,2-oxazol-3-yl)-cis-8,9-dimethyl-6-oxo-6,7,8,9-tetrahydropyrido[3',2':4,5]pyrrolo[1,2-a]pyrazine-2-carboxamide;
6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
6-oxo-N-(quinolin-3-yl)-7,8,9,10-tetrahydro-6H-pyrido[3',2':4,5]pyrrolo[1,2-a][1,4]diazepine-2-carboxamide;
10-methyl-6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
(9R)—N-(5-benzyl-1,2-oxazol-3-yl)-9-methyl-6-oxo-6,7,8,9-tetrahydropyrido[3',2':4,5]pyrrolo[1,2-a]pyrazine-2-carboxamide;
N-(4-methylpyridin-2-yl)-6-oxo-7,8,9,10-tetrahydro-6H-pyrido[3',2':4,5]pyrrolo[1,2-a][1,4]diazepine-2-carboxamide;
N-(1-ethyl-1H-benzimidazol-2-yl)-1-oxo-2,3,4,5-tetrahydro-1H-[1,4]diazepino[1,2-a]benzimidazole-8-carboxamide;
N-(3-benzyl-1,2-oxazol-5-yl)-6-oxo-7,8,9,10-tetrahydro-6H-pyrido[3',2':4,5]pyrrolo[1,2-a][1,4]diazepine-2-carboxamide; and
the pharmaceutically acceptable salts thereof.

In another embodiment, the invention relates to a compound selected from the group consisting of:
N-(5-benzyl-1,2-oxazol-3-yl)-10-methyl-6-oxo-7,8,9,10-tetrahydro-6H-pyrido[3',2':4,5]pyrrolo[1,2-a][1,4]diazepine-2-carboxamide;
10-methyl-6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
10-methyl-6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
N-(1-benzyl-1H-pyrazol-4-yl)-cis-8,9-dimethyl-6-oxo-6,7,8,9-tetrahydropyrido[3',2':4,5]pyrrolo[1,2-a]pyrazine-2-carboxamide;
N-(3-benzyl-1,2-oxazol-5-yl)-10-methyl-6-oxo-7,8,9,10-tetrahydro-6H-pyrido[3',2':4,5]pyrrolo[1,2-a][1,4]diazepine-2-carboxamide;
10-methyl-N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide;
Cis-8,9-dimethyl-N-(5-methyl-1,2-oxazol-3-yl)-6-oxo-6,7,8,9-tetrahydropyrido[3',2':4,5]pyrrolo[1,2-a]pyrazine-2-carboxamide;
N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide;
N-(3-fluorophenyl)-6-oxo-7,8,9,10-tetrahydro-6H-pyrido[3',2':4,5]pyrrolo[1,2-a][1,4]diazepine-2-carboxamide;
5,5-dimethyl-1-oxo-N-[1-(propan-2-yl)-1H-benzimidazol-2-yl]-2,3,4,5-tetrahydro-1H-[1,4]diazepino[1,2-a]benzimidazole-8-carboxamide;
6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;
N-(1-ethyl-1H-benzimidazol-2-yl)-cis-8,9-dimethyl-6-oxo-6,7,8,9-tetrahydropyrido[3',2':4,5]pyrrolo[1,2-a]pyrazine-2-carboxamide;
1-oxo-N-[1-(propan-2-yl)-1H-benzimidazol-2-yl]-2,3,4,5-tetrahydro-1H-[1,4]diazepino[1,2-a]benzimidazole-8-carboxamide;
N-(1-benzyl-1H-pyrazol-4-yl)-9,9-dimethyl-6-oxo-7,8,9,10-tetrahydro-6H-pyrido[3',2':4,5]pyrrolo[1,2-a][1,4]diazepine-2-carboxamide;
9-methyl-6-oxo-N-(pyridin-3-yl)-6,7,8,9-tetrahydropyrido[3',2':4,5]pyrrolo[1,2-a]pyrazine-2-carboxamide;
N-(1-ethyl-1H-benzimidazol-2-yl)-10-methyl-6-oxo-7,8,9,10-tetrahydro-6H-pyrido[3',2':4,5]pyrrolo[1,2-a][1,4]diazepine-2-carboxamide;
9,9-dimethyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide; and
the pharmaceutically acceptable salts thereof.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

The term "carbocycle" or "cycloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds depicted in Table 1. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

DETAILED DESCRIPTION OF THE INVENTION

General Synthetic Methods

The invention also provides processes for making compounds of Formula (I). In all methods, unless specified otherwise, $R^1$, $R^2$, $R^3$, $R^4$, $R^5$ and n in the formulas below shall have the meaning of $R^1$, $R^2$, $R^3$, $R^4$, $R^5$ and n in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) may be synthesized by the method shown in scheme 1

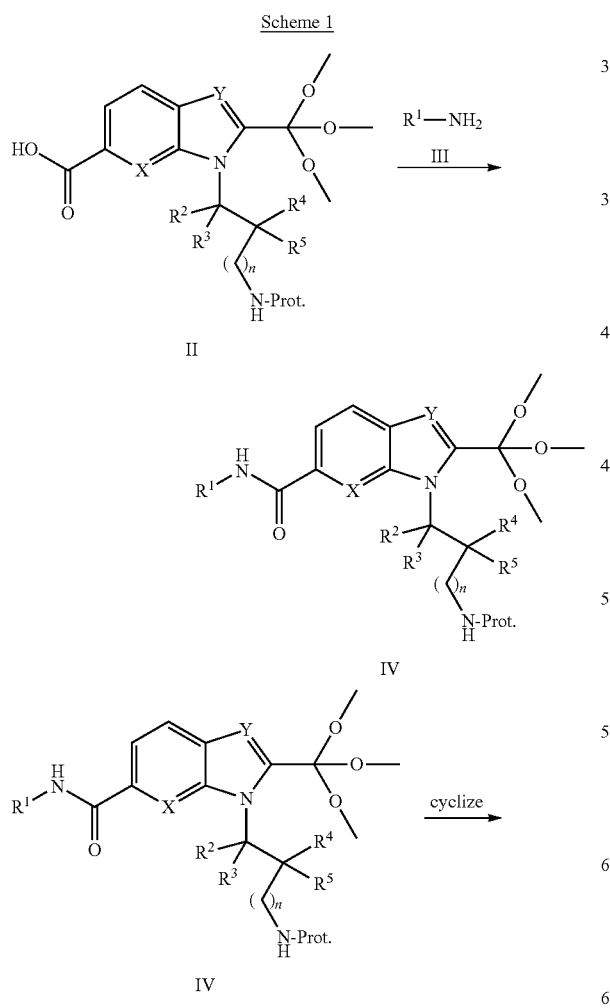

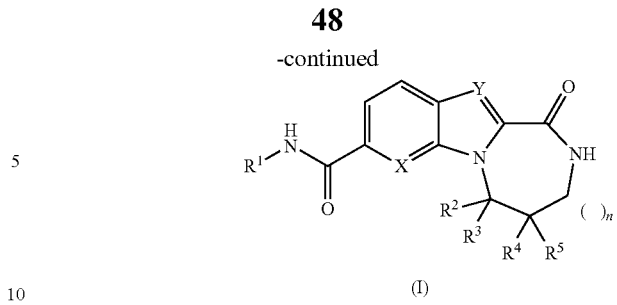

As illustrated in scheme 1, an acid of formula II is coupled with an amine of formula III under standard coupling conditions, to provide a compound of formula IV. Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, TBTU, PyBOP and a base such as diisopropylethylamine, followed by the desired amine of formula III, to provide a compound of IV. Alternatively, reacting the acid of formula II with a reagent such as thionyl chloride or oxalyl chloride, provides the acid chloride which is then reacted with an amine of formula III, in a suitable solvent, in the presence of a suitable base, to provide a compound of formula IV wherein Prot.=protecting group such as BOC. Deprotection followed by cyclization of the intermediate of formula IV, under standard reaction conditions, provides a compound of Formula (I)

Compounds of Formula (I) may also be synthesized by the method shown in scheme 2

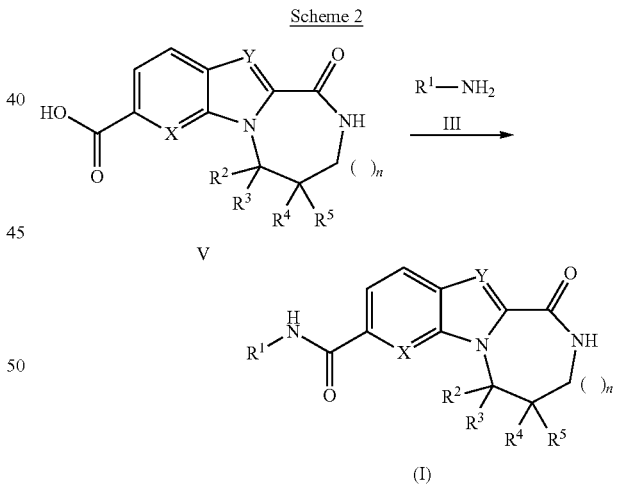

As shown in scheme 2, an acid of formula V is coupled with an amine of formula III under standard coupling conditions, as described in scheme 1 and in the examples, to provide a compound of Formula (I).

Further modification of the initial product of Formula (I) by methods known in the art and illustrated in the Examples below, may be used to prepare additional compounds of this invention.

The intermediate acid of formula II may be prepared according to the method outlined in scheme 3

Scheme 3

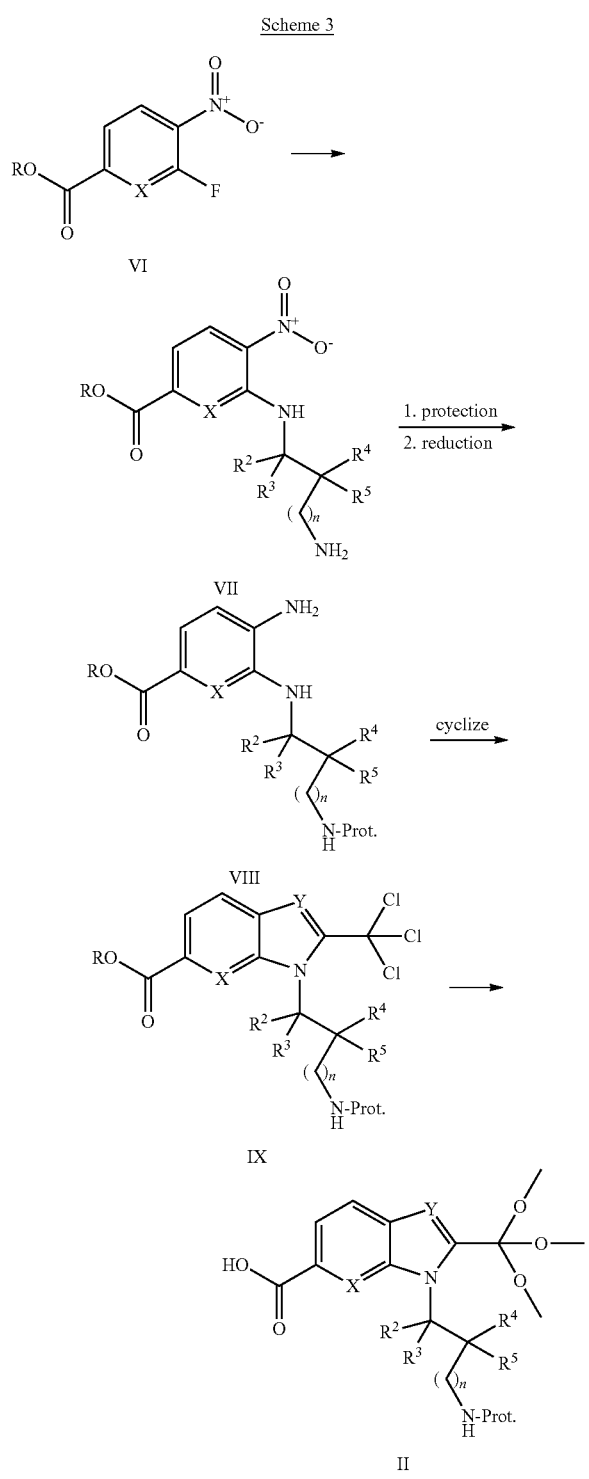

As outlined in scheme 3, reaction of a nitro compound of formula VI with a diamino alkyl compound, in a suitable solvent, provides the corresponding intermediate of formula VII. Protection of the amino group of intermediate VII followed by the reduction of the nitro group, under standard conditions, provides the corresponding amino compound of formula VIII. Cyclization of the intermediate of formula VIII using a reagent such as methyl trichloroacetimidate, in a suitable solvent provides cyclized trichloro compound of formula IX. Reaction of the trichloro compound of formula IX with sodium methoxide provides the acid of formula II.

The intermediate acid of formula V may be prepared according to the method outlined in scheme 4

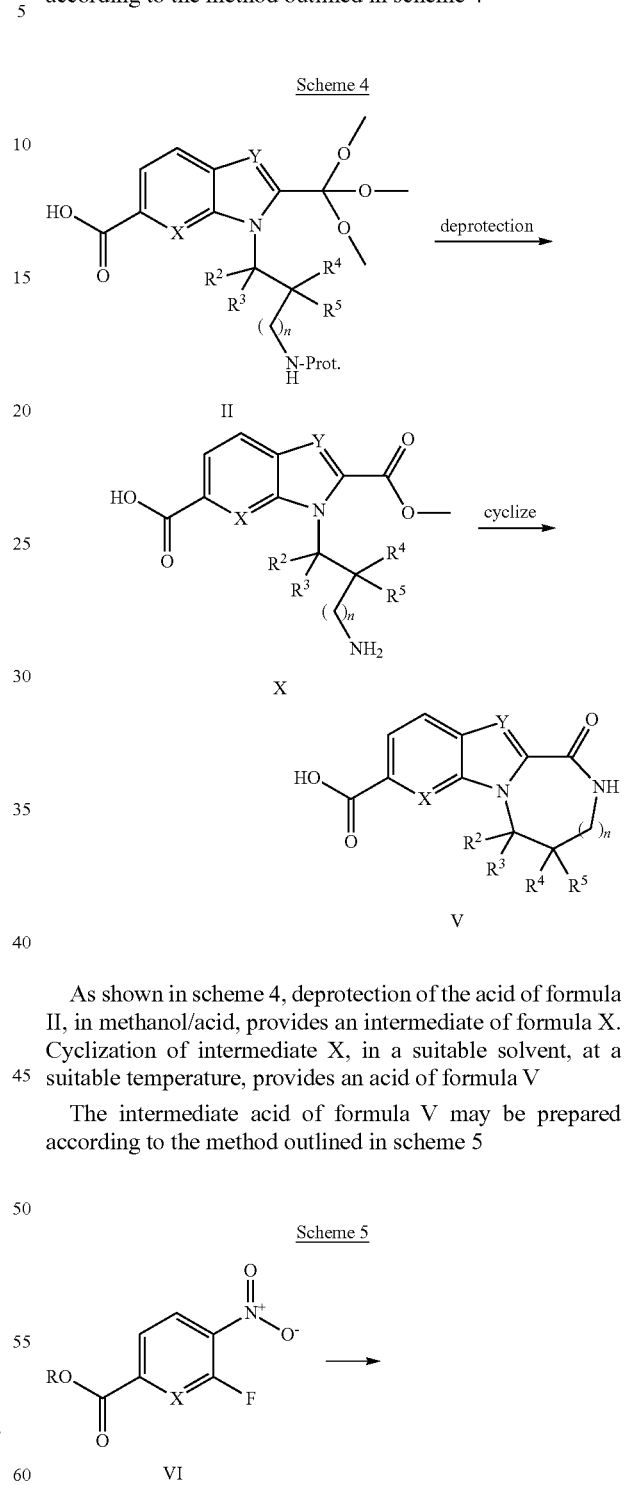

As shown in scheme 4, deprotection of the acid of formula II, in methanol/acid, provides an intermediate of formula X. Cyclization of intermediate X, in a suitable solvent, at a suitable temperature, provides an acid of formula V The intermediate acid of formula V may be prepared according to the method outlined in scheme 5

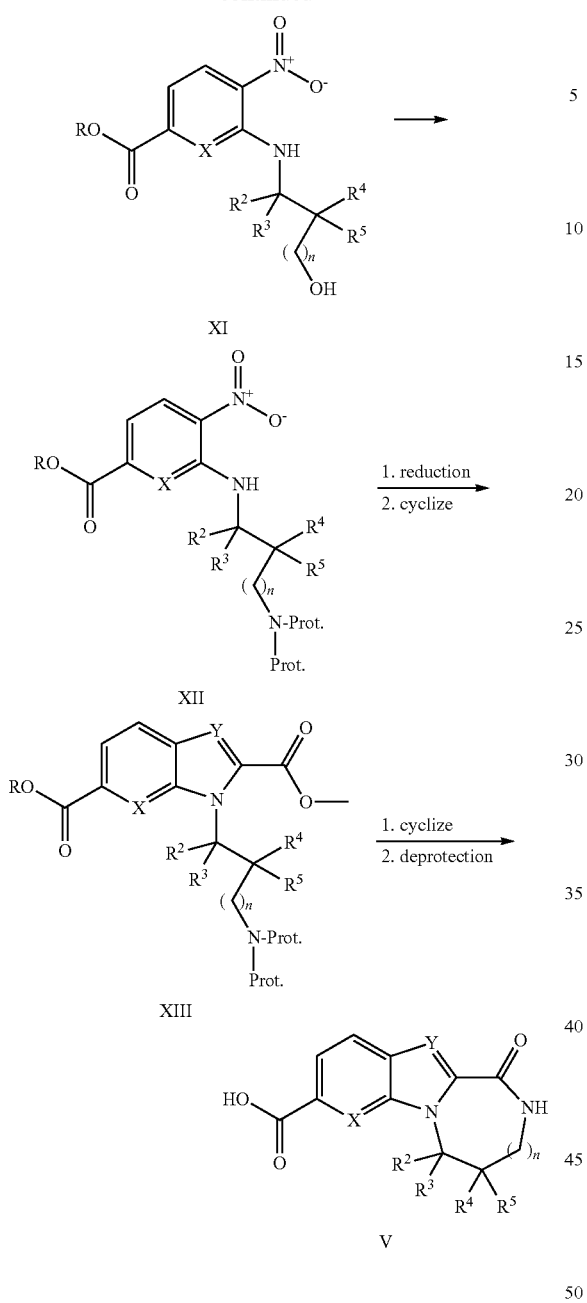
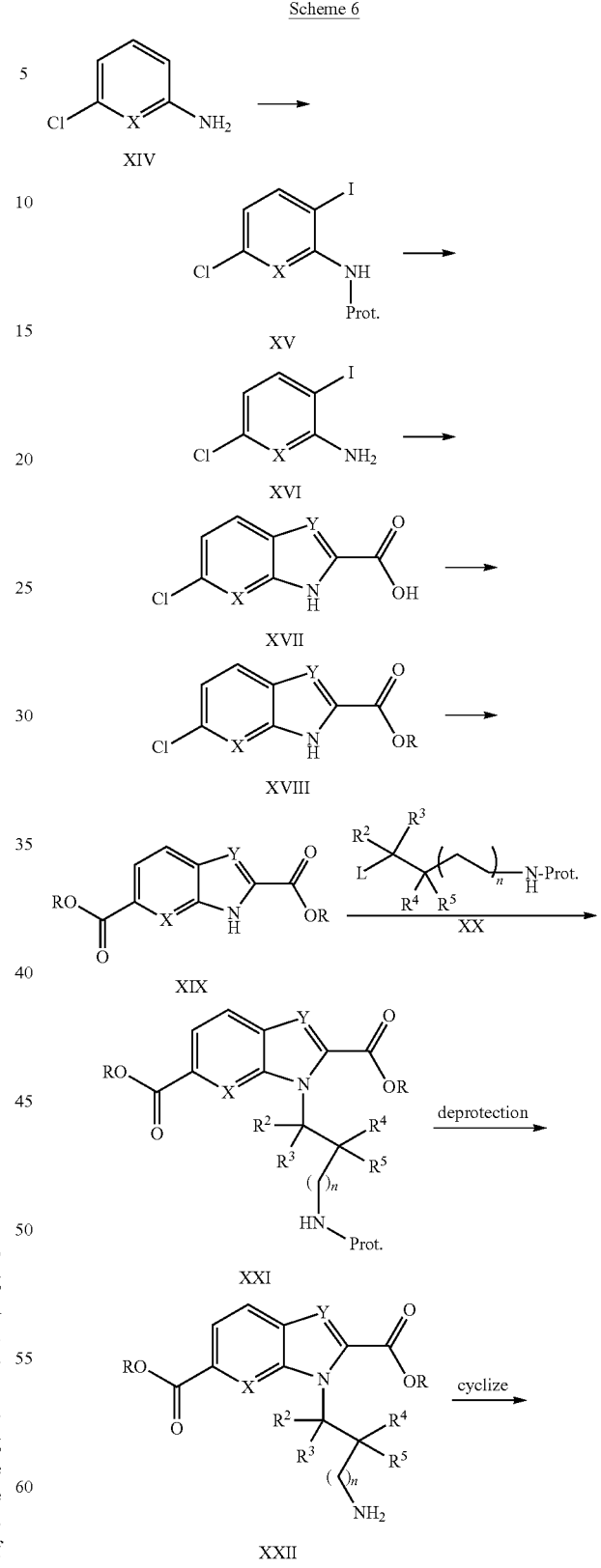

Reaction of a nitro compound of formula VI with an amino alcohol, in a suitable solvent, provides the corresponding intermediate of formula XI. Reaction of intermediate XI with reagents such as di-t-butyl iminodicarboxylate, triphenyl phosphine and dialkyl azidodicarboxylate, in a suitable solvent, provides an intermediate compound of formula XII. Reduction of the nitro group in intermediate XII, under standard conditions followed by cyclization of the resulting amine using a reagent such as ethyl glyoxalate, provides the cyclized compound of formula XIII. Deprotection of the amino group in compound XIII followed by cyclization provides the corresponding cyclized product. Deprotection of this cyclized product affords an acid of formula V.

The intermediate acid of formula V may be prepared according to the method outlined in scheme 6

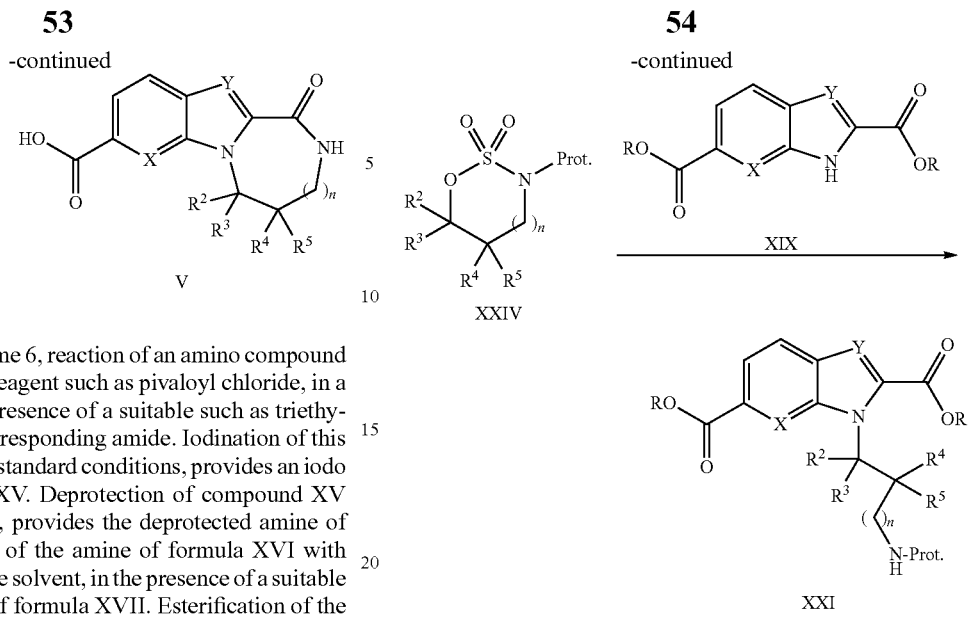

As illustrated in scheme 6, reaction of an amino compound of formula XIV with a reagent such as pivaloyl chloride, in a suitable solvent in the presence of a suitable such as triethylamine, provides the corresponding amide. Iodination of this amide compound under standard conditions, provides an iodo compound of formula XV. Deprotection of compound XV under acidic conditions, provides the deprotected amine of formula XVI. Reaction of the amine of formula XVI with pyruvic acid, in a suitable solvent, in the presence of a suitable base, provides an acid of formula XVII. Esterification of the compound XVII provides the corresponding ester of formula XVIII. Pd catalyzed carbonylation of compound of formula XVIII, provides a diester of formula XIX.

Reaction of the intermediate XIX with compound of formula XX under suitable reaction conditions, provides an intermediate of formula XXI. L=leaving group such as bromo. When L is hydroxyl, it is converted to a leaving group using standard methodology known to one skilled in the art. Deprotection of compound XXI provides the amino compound of formula XXII. Cyclization of compound XXII followed by hydrolysis of the ester group affords the acid of formula V.

The intermediate acid of formula V may be prepared according to the method outlined in scheme 7

As illustrated in scheme 7, reaction of a compound of formula XX, wherein L=OH, with thionyl chloride, in a suitable solvent, in the presence of a suitable base, provides an oxathiazinane intermediate of formula XXIII. Oxidation of compound XXIII provides the corresponding dioxide of formula XXIV. Reaction of compound XXIV with compound XIX, in a suitable solvent, in the presence of a suitable base, provides the intermediate of formula XXI. Compound XXI is converted to the desired acid of formula V by the reaction scheme outlined in scheme 6.

Retention times for the compounds are obtained on an HPLC system using the conditions shown in Table 2 below.

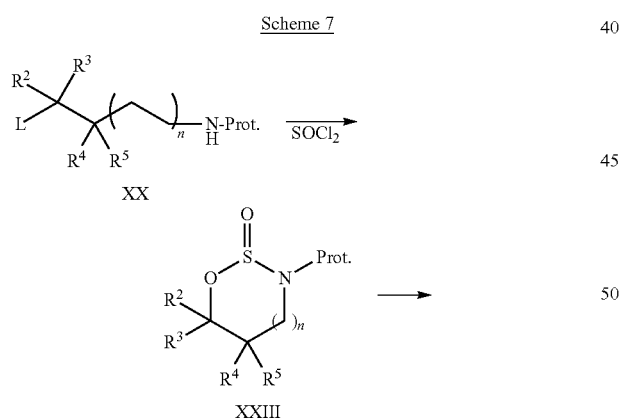

Scheme 7

TABLE 2

| Method | Time (min) | Water + 0.1% HCO$_2$H | CH$_3$CN + 0.1% HCO$_2$H | Flow (mL/min) | Column |
|---|---|---|---|---|---|
| T | 0 | 95 | 5 | 2.5 | Agilent Zorbax C18 |
|  | 1.7 | 5 | 95 | 2.5 | SB 3.5 um 4.6 × 30 mm |
|  | 2 | 5 | 95 | 2.5 | cartridge |
|  | 2.1 | 95 | 5 | 2.5 |  |
|  | 2.3 | 95 | 5 | 2.5 |  |
| V | 0 | 88 | 12 | 1.5 | Agilent SB-C18 |
|  | 0.25 | 70 | 30 | 1.5 | 1.8 um 3 × 50 mm |

TABLE 2-continued

| Method | Time (min) | Water + 0.1% HCO₂H | CH₃CN + 0.1% HCO₂H | Flow (mL/min) | Column |
|---|---|---|---|---|---|
|   | 0.3  | 60 | 40  | 1.5 | column |
|   | 1.19 | 5  | 95  | 1.5 |  |
|   | 1.75 | 0  | 100 | 1.5 |  |
| H | 0    | 90 | 10  | 0.8 | Waters BEH |
|   | 1.19 | 5  | 95  | 0.8 | 2.1 × 50 mm C18 |
|   | 1.7  | 5  | 95  | 0.8 | 1.7 um column |
| B | 0    | 99 | 1   | 1.5 | Agilent Zorbax |
|   | 2    | 80 | 20  | 1.5 | Eclipse XDB-C8 |
|   | 7    | 5  | 95  | 1.5 | 5 um 4.6 × 150 mm |
|   | 9    | 5  | 95  | 1.5 | column |
|   | 9.3  | 99 | 1   | 1.5 |  |
|   | 10   | 99 | 1   | 1.5 |  |

SYNTHETIC EXAMPLES

Intermediate A: 1-(3-tert-Butoxycarbonylaminopropyl)-2-trimethoxymethyl-3H-benzimidazole-5-carboxylic acid

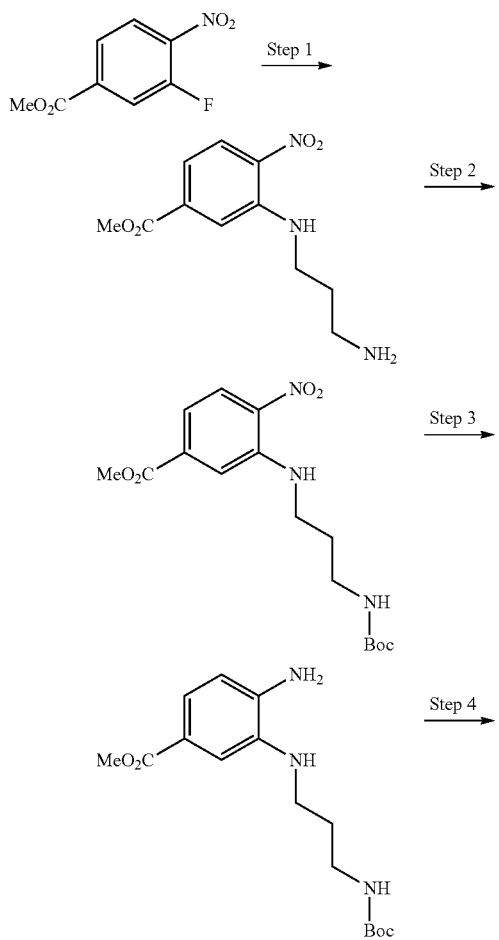

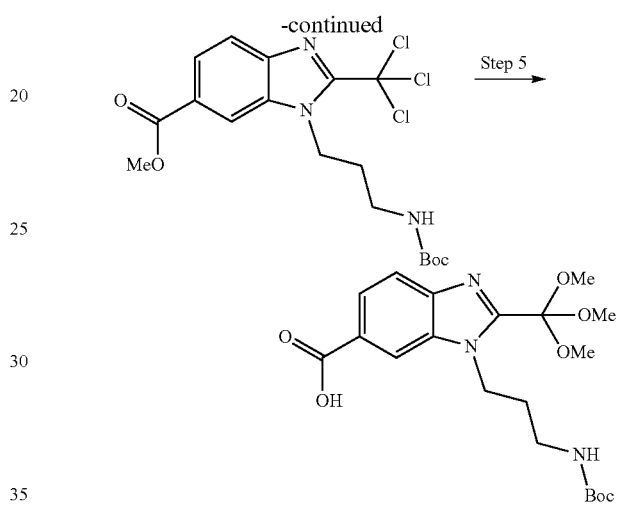

Step 1: Synthesis of Methyl 3-[(3-aminopropyl)amino]-4-nitrobenzoate

To a stirred solution of methyl 3-fluoro-2-nitrobenzoate (22.0 g, 110.0 mmol) in acetonitrile (200 ml) is added 1,3-diaminopropane (89.3 g, 1.21 mol) and the reaction is stirred at room temperature for 3 h. The solvent is evaporated, H₂O (100 mL) is added to the residue, and the mixture is extracted with EtOAc (5×100 mL). The combined organic layers are dried (Na₂SO₄) and evaporated to afford the title compound (22.4 g, 80%) which is used in the next step without purification. LCMS (Method T) 1.05 min, 254.58 (MH+).

Step 2: Synthesis of Methyl 3-({3-[(tert-butoxycarbonyl)amino]propyl}amino)-4-nitrobenzoate To a stirred solution of methyl 3-[(3-aminopropyl)amino]-4-nitrobenzoate (25.0 g, 98.7 mmol) in CH₂Cl₂ (1 L) at 0° C. is added a solution of di-tert-butyl dicarbonate (23.6 g, 109 mmol) in CH₂Cl₂ (200 mL). The solution is stirred at room temperature for 17 h. The solvent is evaporated to leave a solid. The crystals are triturated with methanol, filtered washing with methanol, and dried to afford the title compound as bright yellow crystals, (30.1 g, 85%), which is used directly for the next step. LCMS (Method T) 1.79 min, 354.72 (MH+).

Step 3: Synthesis of Methyl 4-amino-3-({3-[(tert-butoxycarbonyl)amino]propyl}amino)benzoate A stirred suspension of methyl 3-({3-[(tert-butoxycarbonyl)amino]propyl}amino)-4-nitrobenzoate (6.5 g, 18.4 mmol) in ethyl acetate (500 mL) is hydrogenated over 10% palladium on carbon (2.6 g) under balloon pressure for 4 h. The catalyst is removed by filtration through Celite, washing well with ethyl acetate. The solvent is evaporated to afford the title compound (4.72 g, 80%) as a white solid. LCMS (Method T) 1.39 min, 324.70 (MH+).

Step 4: Synthesis of Methyl 1-{3-[(tert-butoxycarbonyl)amino]propyl}-2-(trichloromethyl)-1H-benzimidazole-6-carboxylate To a stirred solution of methyl 4-amino-3-({3-[(tert-butoxycarbonyl)amino]propyl}amino)benzoate (4.7 g, 14.5 mmol) in acetic acid (50 mL) is added methyl trichloroacetimidate (3.1 g, 17.4 mmol). After 3 h at room temperature, the solvent is evaporated, the residue is dissolved in EtOAc, and is washed with $Na_2CO_3$ and brine. The organic layer is dried ($Na_2SO_4$) and evaporated. The residue is triturated with hexanes to afford the title compound (5.2 g, 80%) as a fine powder. LCMS (Method T), 1.85 min, 450.63 (MH+).

Step 5: 1-{3-[(tert-Butoxycarbonyl)amino]propyl}-2-(trimethoxymethyl)-1H-benzimidazole-6-carboxylic acid To a solution of methyl 1-{3-[(tert-butoxycarbonyl)amino]propyl}-2-(trichloromethyl)-1H-benzimidazole-6-carboxylate (9.6 g, 117.4 mmol) in methanol (400 mL) at 0° C. is added a 25% solution of sodium methoxide in methanol (9.6 g, 117.4 mmol). The stirred solution is heated to reflux for 20 h. The solution is cooled, most of the methanol evaporated, and water is added. The solution is washed with $CH_2Cl_2$ twice, and the extracts set aside. The aqueous layer is acidified with 1M $NaHSO_4$, and extracted with $CH_2Cl_2$ (3×). The combined organic phases are dried ($Na_2SO_4$) and evaporated to afford the title compound (9.3 g, 50%) as an off-white solid. LCMS (Method T) 1.31 min, 424.77 (MH+).

Intermediate B: 1-oxo-2,3,4,5-tetrahydro-1H-[1,4]diazepino[1,2-a]benzimidazole-8-carboxylic acid Step 1: Synthesis of 1-(3-aminopropyl)-2-(methoxycarbonyl)-1H-benzimidazole-6-carboxylic acid hydrochloride To a solution of 1-{3-[(tert-Butoxycarbonyl)amino]propyl}-2-(trimethoxymethyl)-1H-benzimidazole-6-carboxylic acid (Intermediate A, 20 g, 68.7 mmol) in methanol (200 mL) is added conc. HCl (5 mL) and the reaction mixture is stirred at room temperature for 1 h. The solvent is evaporated to afford the title compound as a solid (20 g, 92%) which is used in the next reaction without purification.

Step 2: Synthesis of 1-Oxo-2,3,4,5-tetrahydro-1H-[1,4]diazepino[1,2-a]benzimidazole-8-carboxylic acid Triethylamine (14.3 g, 141.7 mmol) is added to a solution of the crude 1-(3-aminopropyl)-2-(methoxycarbonyl)-1H-benzimidazole-6-carboxylic acid hydrochloride (20 g, 47.2 mmol) in methanol (100 mL) and reaction mixture is refluxed for 1 h. The reaction mixture is cooled and acidified with 1M HCl. The solvent is evaporated and water is added. The resultant solid is collected by filtration and purified by acid-base neutralization using sodium bicarbonate and conc. HCl to afford the title compound (3.4 g, 30%) as a solid.

Intermediate C: 5,5-Dimethyl-1-oxo-2,3,4,5-tetrahydro-1H-[1,4]diazepino[1,2-a]benzimidazole-8-carboxylic acid

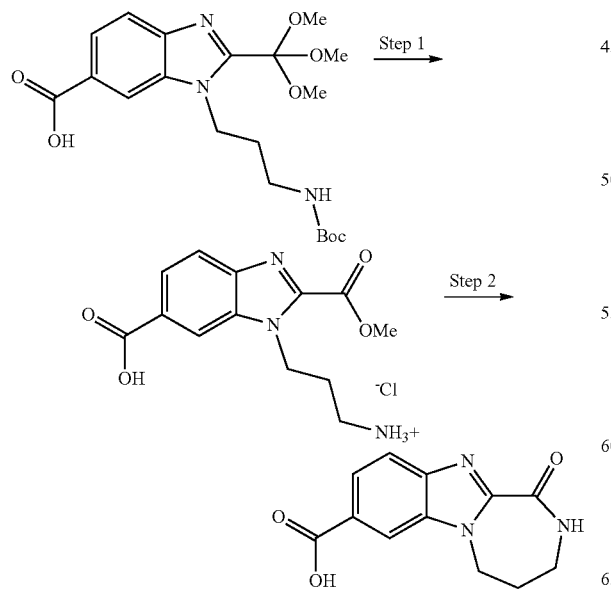

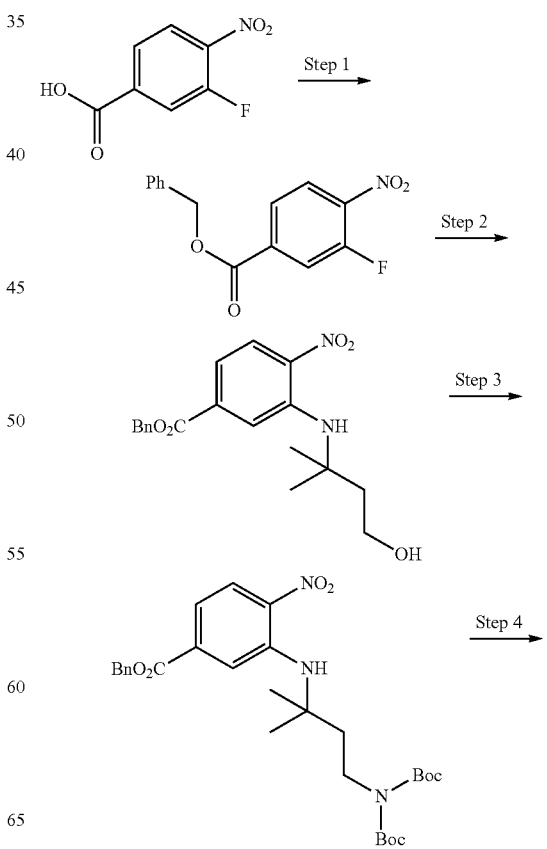

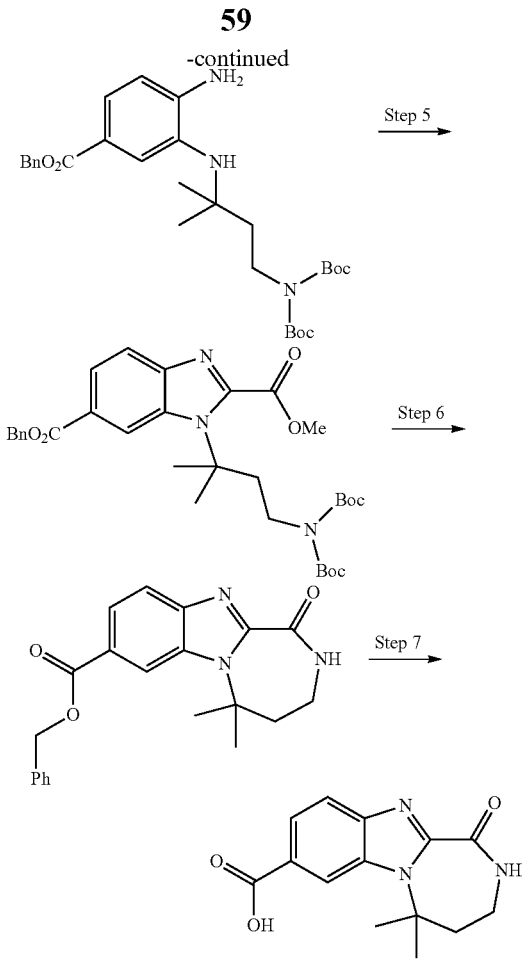

Step 1: Synthesis of Benzyl 3-fluoro-4-nitrobenzoate

Oxalyl chloride (4.60 mL), 53.6 mmol) is added to a stirred suspension of 3-fluoro-4-nitrobenzoic acid (5.11 g, 26.8 mmol) in CH$_2$Cl$_2$ (100 mL). DMF (0.1 mL) is added, and the solution stirred for 2 h at room temperature. The solvent is evaporated, and the residue is dissolved in CH$_2$Cl$_2$ (100 mL). Benzyl alcohol (5.54 mL, 53.6 mmol) and pyridine (2 mL) are added and the solution stirred for 16 h. The solvent is removed and the residue purified by filtration through a pad of silica gel, eluting with EtOAc/heptanes (1:9) to afford the title compound (6.8 g, 24.7 mmol).

Step 2: Synthesis of Benzyl 3-[(4-hydroxy-2-methylbutan-2-yl)amino]-4-nitrobenzoate A stirred solution of benzyl 3-fluoro-4-nitrobenzoate (2.67 g, 9.69 mmol) and 3-amino-3-methylbutan-1-ol (1.00 g, 9.69 mmol) in acetonitrile (20 mL) containing potassium carbonate (1.34 g, 9.69 mmol) is heated to 80° C. for 16 h. The solvent is evaporated, water (100 mL) is added, and the mixture is extracted with EtOAc (3×100 mL). The combined organic layers are dried (MgSO$_4$), concentrated and purified by flash chromatography in heptanes/EtOAc to afford the title compound (395 mg, 1.10 mmol).

Step 3: Synthesis of Benzyl 3-({4-[bis(tert-butoxycarbonyl)amino]-2-methylbutan-2-yl}amino)-4-nitrobenzoate To a stirred solution of benzyl 3-[(4-hydroxy-2-methylbutan-2-yl)amino]-4-nitrobenzoate (395 mg, 1.10 mmol), di- tert-butyl iminodicarboxylate (367 mg, 1.65 mmol), and triphenylphosphine (430 mg, 1.65 mmol) in THF (5 mL) is added diisopropyl azodicarboxylate (0.34 mL, 1.65 mmol). After 16 h at room temperature the solvent is evaporated and the residue is purified by flash chromatography on silica eluting with a heptane/EtOAc gradient to afford the title compound (280 mg, 0.50 mmol, 46%).

Step 4: Synthesis of Benzyl 4-amino-3-({4-[bis(tert-butoxycarbonyl)amino]-2-methylbutan-2-yl}amino)benzoate To a stirred suspension of benzyl 3-({4-[bis(tert-butoxycarbonyl)amino]-2-methylbutan-2-yl}amino)-4-nitrobenzoate (280 mg, 0.50 mmol) and zinc dust (344 mg, 5.27 mmol) in methanol (9 mL) is added acetic acid (0.34 mL), dropwise. The mixture is stirred for 20 min, methanol (50 mL) is added and the mixture is filtered through Celite. The filtrate is concentrated and partitioned between EtOAc and H$_2$O, adjusting the pH to 5 by adding 1M HCl. The organic layer is washed with NaHCO$_3$ and H$_2$O, dried (MgSO$_4$) and evaporated to afford the title compound (250 mg, 94%) which is used in the next step without further purification.

Step 5: Synthesis of 1-({4-[Bis(tert-butoxycarbonyl)amino]-2-methylbutan-2-yl}-1H-benzimidazole-2,6-dicarboxylic acid 6-benzyl ester 2-methyl ester To a stirred solution of crude benzyl 4-amino-3-({4-[bis(tert-butoxycarbonyl)amino]-2-methylbutan-2-yl}amino)benzoate (250 mg, 0.47 mmol) in methanol (10 mL) is added a 50% solution of ethyl glyoxalate in toluene (0.38 mL, 1.90 mmol). After 16 h, the solvent is evaporated to afford the title compound (295 mg, >99%), which is used in the next step without purification.

Step 6: Synthesis of Benzyl 5,5-dimethyl-1-oxo-2,3,4,5-tetrahydro-1H-[1,4]diazepino[1,2-a]benzimidazole-8-carboxylate To a stirred solution of crude 1-({4-[bis(tert-butoxycarbonyl)amino]-2-methylbutan-2-yl}-1H-benzimidazole-2,6-dicarboxylic acid 6-benzyl ester 2-methyl ester (289 mg, 0.47 mmol) in CH$_2$Cl$_2$ (5 mL) is added TFA (1 mL). After 1 h the solvent is evaporated, and CH$_2$Cl$_2$ is added and evaporated from the residue three times to remove excess TFA. The residue is dissolved in methanol (10 mL) and triethylamine (0.72 mL, 5.16 mmol) added. The solution is stirred at room temperature for 16 h. The solvent is evaporated and the residue partitioned between H$_2$O and EtOAc. The organic layer is dried (MgSO$_4$) and purified by flash chromatography, eluting with CH$_2$Cl$_2$/methanol to afford the title compound (80 mg, 44%).

Step 7: Synthesis of 5,5-Dimethyl-1-oxo-2,3,4,5-tetrahydro-1H-[1,4]diazepino[1,2-a]benzimidazole-8-carboxylic acid A suspension of benzyl 5,5-dimethyl-1-oxo-2,3,4,5-tetrahydro-1H-[1,4]diazepino[1,2-a]benzimidazole-8-carboxylate (88 mg, 0.22 mmol) in methanol (2 mL) is hydrogenated over 10% palladium on carbon (23 mg) under balloon pressure for 3 h. The catalyst is removed by filtration, and the filtrate concentrated to afford the title compound (38 mg, 63%).

Intermediate D: Diethyl 1H-pyrrolo[2,3-b]pyridine-2,6-dicarboxylate

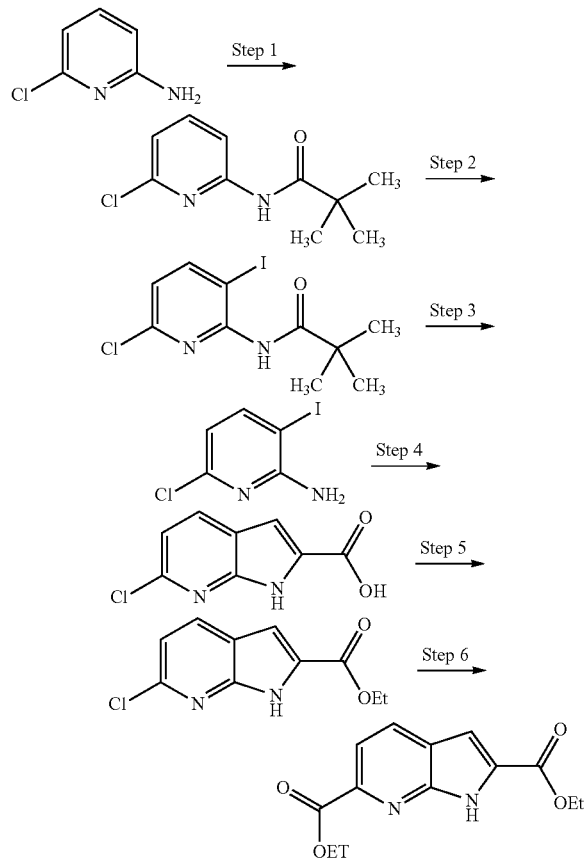

Step 1: Synthesis of N-(6-Chloropyridin-2-yl)-2,2-dimethylpropionamide

To a solution of 6-chloro-2-aminopyidine (50 g, 389 mmol) and triethylamine (68 mL, 486 mmol) in dry CH$_2$Cl$_2$ (250 mL) at 0° C. is added pivaloyl chloride (52 g, 428 mmol), dropwise. The reaction mixture is stirred at ambient temperature for 16 h. Saturated NH$_4$Cl solution (100 mL) is added and the mixture is extracted with CH$_2$Cl$_2$ (3×200 mL). The combined organic layers are washed with saturated NaHCO$_3$ solution, dried (Na$_2$SO$_4$) and evaporated to afford the title compound as an off-white solid (70 g, 86%) which is used in the next step without purification.

Step 2: Synthesis of N-(6-Chloro-3-iodopyridin-2-yl)-2,2-dimethylpropionamide To a solution of N-(6-chloropyridin-2-yl)-2,2-dimethyl-propionamide (20 g, 94 mmol) in dry THF (500 mL) at −78° C., 1.3 M t-BuLi in hexane (220 mL, 282 mmol) is added dropwise. The reaction mixture is stirred for 30 min and a solution of iodine (29 g, 114 mmol) in dry THF is added. The reaction mixture is stirred for 3 h at −78° C. then is warmed to ambient temperature and stirred for another 1 h. The reaction mixture is quenched with 1N HCl and is extracted with ethyl acetate (2×250 mL). The organic layers are separated and washed with Na$_2$S$_2$O$_3$ solution and saturated NaHCO$_3$ solution, respectively. The combined organic layers are dried (Na$_2$SO$_4$) and evaporated under reduced pressure. The crude residue is purified by flash column chromatography using 20% EtOAc/petroleum ether to afford the title compound as a pale yellow solid (15 g, 49%).

Step 3: Synthesis of 6-Chloro-3-iodopyridin-2-amine

N-(6-Chloro-3-iodopyridin-2-yl)-2,2-dimethylpropiona-mide (33 g, 97 mmol) is dissolved in 1N HCl (300 mL) in the presence of catalytic amount of methanol (0.5 mL) at 0° C. The reaction mixture is heated at 110° C. for 5 h. After cooling, the reaction mixture is extracted with ethyl acetate (2×250 mL). The organic layers are separated and the solvent is evaporated to afford the title compound as a viscous liquid (24 g, 97%) which is used in the next step without purification.

Step 4: Synthesis of 6-Chloro-1H-pyrrolo[2,3-b]pyridine-2-carboxylic acid

To a solution of 6-chloro-3-iodopyridin-2-amine (24 g, 94 mmol) in DMF is added DABCO (32 g, 283 mmol) and pyruvic acid (20 mL, 283 mmol). The mixture is degassed by bubbling argon gas through the mixture for 20 min. Pd(OAc)$_2$ (1 g, 4.7 mmol) is added and the mixture is again degassed. The reaction mixture is heated at 110° C. for 3 h, and the solvent is evaporated to afford the title compound as a viscous liquid (36 g, >99%) which is used in the next step without purification.

Step 5: Synthesis of Ethyl 6-chloro-1H-pyrrolo[2,3-b]pyridine-2-carboxylate

HCl gas is bubbled through a solution of 6-chloro-1H-pyrrolo[2,3-b]pyridine-2-carboxylic acid (36 g, 183 mmol) in ethanol (500 mL) at 0° C. for 30 min. The reaction mixture is then heated at reflux for 16 h. The solvent is evaporated and the residue is diluted with CH$_2$Cl$_2$ and filtered. The filtrate is evaporated and the residue is washed with diethyl ether (2×250 mL). The organic layers are dried (Na$_2$SO$_4$) and concentrated. The crude residue is purified by passing through the column of neutral alumina, eluting with 10% EtOAc/hexane to afford the title compound as a white solid (10 g, 25%).

Step 6: Synthesis of Diethyl 1H-pyrrolo[2,3-b]pyridine-2,6-dicarboxylate

Reagents are charged into a 600 mL autoclave in the following order: ethanol (350 mL), sodium acetate (17.0 g, 200 mmol), 6-chloro-1H-pyrrolo[2,3-b]pyridine-2-carboxylic acid ethyl ester (24 g, 107 mmol), 1,1'-bis-(diphenylphos-phino)ferrocene (2.5 g, 2.25 mmol [2.25 mol %]), and palladium acetate (180 mg, 0.75 mmol [0.75 mol %]). The air in the autoclave is replaced with carbon monoxide and the pressure is adjusted to 250 psi. The reaction is then heated to 110° C. for 15 h. The reaction mixture is cooled to room temperature and is filtered through Celite. The solvent is replaced with 500 mL EtOAc followed by 100 mL aqueous wash. The organic layer is concentrated to 50 mL EtOAc and is then heated to 60° C. After cooling to room temperature, the solids are filtered to afford 20 g of the title compound. The mother liquor is concentrated and is purified by flash column chromatography using gradient elution of 20-60% ethyl acetate in hexanes to afford an additional 3.5 g of title compound which affords total of 23.5 g in 84% isolated yield.

Intermediate E: 6-Oxo-7,8,9,10-tetrahydro-6H-pyrido[3',2':4,5]pyrrolo[1,2-a][1,4]diazepine-2-carboxylic acid

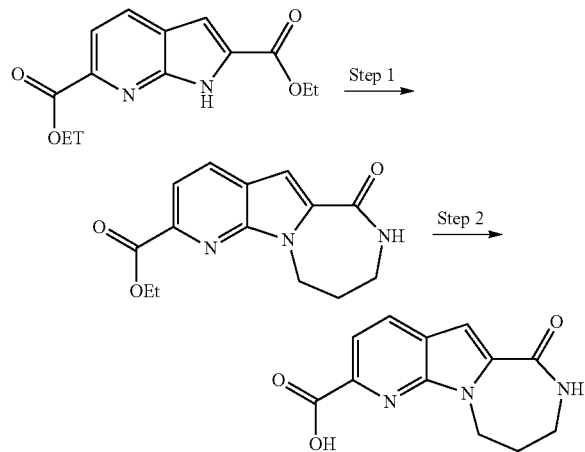

Step 1: Synthesis of Ethyl 6-oxo-7,8,9,10-tetrahydro-6H-pyrido[3',2':4,5]pyrrolo[1,2-a][1,4]diazepine-2-carboxylate To a solution of diethyl 1H-pyrrolo[2,3-b]pyridine-2,6-dicarboxylate (Intermediate D, 2.00 g, 7.23 mmol) in NMP (20 mL) is added potassium carbonate (3.16 g, 22.9 mmol) and 1-(3-bromopropyl)-2,2,5,5-tetramethyl-1-aza-2,5-disilacyclopentane (2.28 mL, 9.15 mmol). The mixture is stirred at room temperature for 16 h. 1M TBAF in THF (9.15 mL, 9.15 mmol) is added and the mixture is stirred at room temperature for 3 h. The reaction is poured over ice and the resulting solid is collected by filtration. The crude material is purified via trituration with CH$_2$Cl$_2$/diethyl ether to afford the title compound as a yellow solid (1.84 g, 88%). LCMS: 274.70 (M+H$^+$).

Step 2: Synthesis of 6-Oxo-7,8,9,10-tetrahydro-6H-pyrido[3',2':4,5]pyrrolo[1,2-a][1,4]diazepine-2-carboxylic acid To a solution of ethyl 6-oxo-7,8,9,10-tetrahydro-6H-pyrido[3',2':4,5]pyrrolo[1,2-a][1,4]diazepine-2-carboxylate (1.84 g, 6.73 mmol) in ethanol (30 mL) is added 1N NaOH solution (16.8 mL, 16.8 mmol). The reaction is stirred at 50° C. for 5 h then is cooled to room temperature. The ethanol is removed in vacuo and the aqueous mixture is acidified to pH 5 with 1N hydrochloric acid. The resulting solid is collected by filtration and dried in vacuo at 50° C. to afford the title compound as a tan solid (1.4 g, quantitative). LCMS: 264.63 (M+H$^+$).

Intermediate F: 9,9-Dimethyl-6-oxo-7,8,9,10-tetrahydro-6H-pyrido[3',2':4,5]pyrrolo[1,2-a][1,4]diazepine-2-carboxylic acid

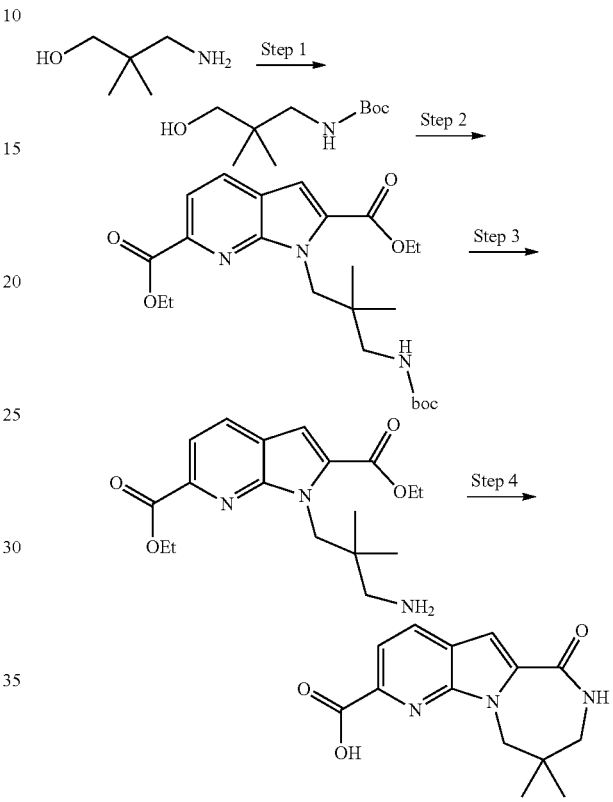

Step 1: Synthesis of tert-Butyl (3-hydroxy-2,2-dimethylpropyl)carbamate

To a solution of 3-amino-2,2-dimethyl-1-propanol (1.50 g, 14.5 mmol) in CH$_2$Cl$_2$ (70 ml) is added di-tert-butyl dicarbonate (3.49 g, 16.0 mmol). The mixture is stirred at room temperature for 16 h. Saturated NH$_4$Cl solution is added and the mixture is stirred for 10 min. The layers are separated and the organic phase is washed with saturated NaHCO$_3$ solution and is dried (Na$_2$SO$_4$) and concentrated in vacuo to afford the title compound as a white solid (3.40 g, quantitative). LCMS: 226.20 (M+Na+).

Step 2: Synthesis of Diethyl 1-{3-[(tert-butoxycarbonyl)amino]-2,2-dimethylpropyl}-1H-pyrrolo[2,3-b]pyridine-2,6-dicarboxylate To a solution of tert-butyl (3-hydroxy-2,2-dimethylpropyl)carbamate (2.13 g, 10.5 mmol), diethyl 1H-pyrrolo[2,3-b]pyridine-2,6-dicarboxylate (Intermediate D, 2.50 g, 9.53 mmol), and triphenylphosphine (5.00 g, 19.1 mmol) in THF (15 mL) is added diisopropyl azodicarboxylate (3.95 mL, 19.1 mmol). The reaction is stirred at room temperature for 64 h. The solvent is removed in vacuo and the crude material is purified via silica gel chromatography using a gradient elution of 0-30% ethyl acetate/hexanes to afford the title compound as a yellow oil which crystallized upon standing (4.20 g, 99%). LCMS: 478.86 (M+Na+).

Step 3: Synthesis of Diethyl 1-(3-amino-2,2-dimethylpropyl)-1H-pyrrolo[2,3-b]pyridine-2,6-dicarboxylate To a solution of diethyl 1-{3-[(tert-butoxycarbonyl)amino]-2,2-dimethylpropyl}-1H-pyrrolo[2,3-b]pyridine-2,6-dicarboxylate (4.20 g, 9.39 mmol) in CH$_2$Cl$_2$ (20 mL) is added TFA (10 mL). The mixture is stirred at room temperature for 4 hr. The solvent is evaporated and the residue is partitioned between ethyl acetate and saturated NaHCO$_3$ solution. The layers are separated and the aqueous layer is further extracted with ethyl acetate. The combined organic phases are washed with brine, and are dried (Na$_2$SO$_4$) and concentrated in vacuo to afford the title compound (3.30 g, quantitative). LCMS: 348.79 (M+H+).

Step 4: Synthesis of 9,9-Dimethyl-6-oxo-7,8,9,10-tetrahydro-6H-pyrido[3',2':4,5]pyrrolo[1,2-a][1,4]diazepine-2-carboxylic acid To a solution of diethyl 1-(3-amino-2,2-dimethylpropyl)-1H-pyrrolo[2,3-b]pyridine-2,6-dicarboxylate (3.30 g, 9.50 mmol) in ethanol (45 mL) is added potassium carbonate (3.94 g, 28.5 mmol). The mixture is stirred at 60° C. for 16 h and is then cooled to room temperature. The ethanol is evaporated and the aqueous mixture is acidified to pH 5 with 1N hydrochloric acid. The resulting solid is collected by filtration and dried in vacuo to afford the title compound as a pale yellow solid (2.80 g, quantitative). LCMS: 274.70 (M+H+).

Intermediate G: 10-Methyl-6-oxo-7,8,9,10-tetrahydro-6H-pyrido[3',2':4,5]pyrrolo[1,2-a][1,4]diazepine-2-carboxylic acid

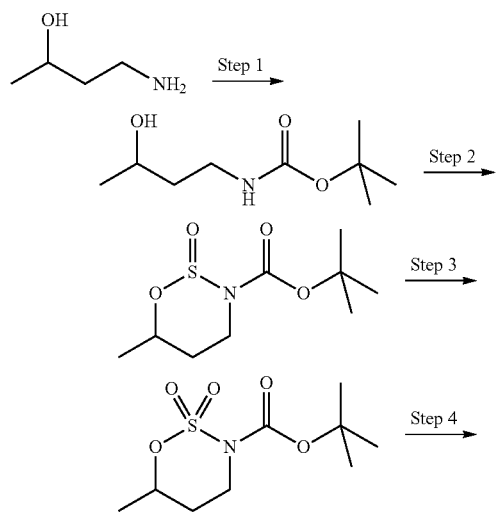

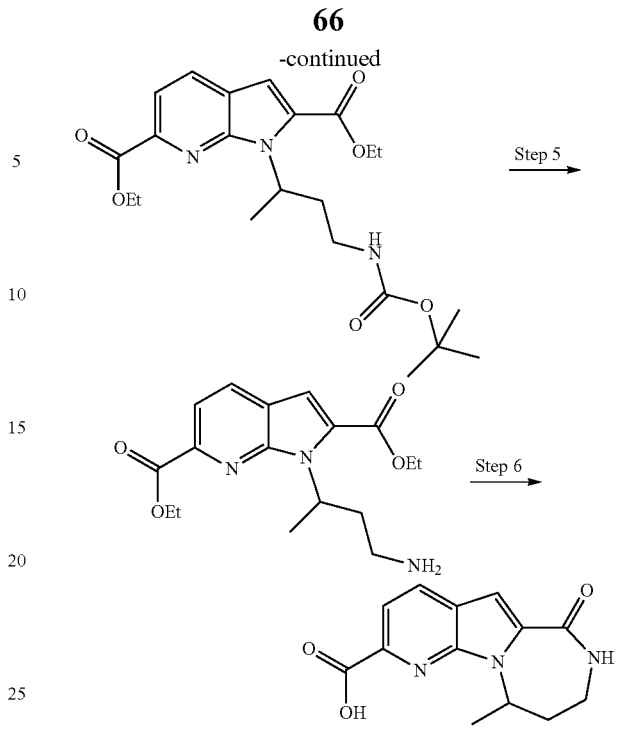

Step 1: Synthesis of tert-Butyl (3-hydroxybutyl)carbamate

To a stirred solution of 4-amino-butan-2-ol (1.0 g, 11.2 mmol) in CH$_2$Cl$_2$ (20 mL) is added a solution of di-tert-butyl dicarbonate (2.45 g, 11.2 mmol) in CH$_2$Cl$_2$ (20 mL). The reaction mixture is stirred for 18 h. The solution is washed with citric acid and saturated NaHCO$_3$ solution, dried (MgSO$_4$) and evaporated to afford the title compound as a colorless oil (2.1 g, 99%).

Step 2: Synthesis of tert-Butyl 6-methyl-1,2,3-oxathiazinane-3-carboxylate 2-oxide A stirred solution of thionyl chloride (2.0 mL, 27.9 mmol) in acetonitrile (15 mL) is cooled down to −45° C. and a solution of tert-butyl (3-hydroxybutyl)carbamate (2.1 g, 11.2 mmol) in acetonitrile (20 mL) is added by syringe over about 10 min, keeping the internal temperature below −40° C. Then DMAP (136 mg, 1.1 mmol) is added followed by the dropwise addition of pyridine (4.5 mL, 55.8 mmol) by syringe, keeping the temperature below −40° C. The addition takes 1.5 h. Ethyl acetate (50 mL) is added to the suspension. The mixture is filtered at −35° C. to remove the solid and the solid is washed with EtOAc before it is discarded. Then the filtrates are combined, and sat. Na$_2$HPO$_4$ solution (20 mL) is added. Again the mixture is stirred vigorously for 30 min. Then the organic layer is separated, washed with 1M NaHSO$_4$ to remove residual pyridine, dried (MgSO$_4$) and concentrated to afford the title compound as an oil (2.52 g, 96%) which is used in the next step without purification.

Step 3: Synthesis of tert-Butyl 6-methyl-1,2,3-oxathiazinane-3-carboxylate 2,2-dioxide The crude tert-butyl 6-methyl-1,2,3-oxathiazinane-3-carboxylate 2-oxide (2.52 g, 10.7 mmol) is dissolved in acetonitrile (25 mL) and H₂O (15 mL) is added. The solution is cooled in an ice bath and sodium periodate (3.4 g, 16.1 mmol) is added in one portion. After 5 min, the pH is adjusted to 7-8 by addition of saturated Na₂HPO₄ solution. Then RuCl₃ (22 mg, 0.11 mmol) in H₂O (0.5 mL) is added. The pH is kept between 6 and 9 by addition of Na₂HPO₄ solution. After 2 h, H₂O (100 mL) is added and pH is adjusted to 6 by addition of 2M HCl solution. The reaction mixture is extracted with EtOAc and the organic layer is washed with NaHCO₃ and brine and the washes are back extracted once with EtOAc. The combined organic layers are dried (MgSO₄), filtered and concentrated. The crude product is purified via by flash column chromatography using a gradient elution of 5-80% ethyl acetate/hexanes which affords the title compound (1.63 g, 61%).

Step 4: Synthesis of Diethyl 1-{4-[(tert-butoxycarbonyl)amino]butan-2-yl}-1H-pyrrolo[2,3-b]pyridine-2,6-dicarboxylate To a solution of diethyl 1H-pyrrolo[2,3-b]pyridine-2,6-dicarboxylate (Intermediate D, 1.00 g, 3.81 mmol) in DMF (15 mL) cooled to 0° C. is added 60% sodium hydride in mineral oil (168 mg, 4.19 mmol). The mixture is stirred at 0° C. for 20 min after which a solution of tert-butyl 6-methyl-1,2,3-oxathiazinane-3-carboxylate 2,2-dioxide (1.05 g, 4.19 mmol) in DMF (2 mL) is added. After being stirred overnight, the mixture is concentrated under reduced pressure and the residue is partitioned between ethyl acetate and saturated NaHCO₃ solution. The layers are separated and the aqueous layer is further extracted with ethyl acetate. The combined organic phases are washed with brine, and are dried (Na₂SO₄). The solvent is removed in vacuo and the crude material is purified via flash column chromatography using a gradient elution of 0-30% ethyl acetate/heptanes to afford the title compound as a yellow oil (1.20 g, 73%). LCMS: 434.89 (M+H⁺).

Step 5: Synthesis of Diethyl 1-(4-aminobutan-2-yl)-1H-pyrrolo[2,3-b]pyridine-2,6-dicarboxylate To a solution of diethyl 1-{4-[(tert-butoxycarbonyl)amino]butan-2-yl}-1H-pyrrolo[2,3-b]pyridine-2,6-dicarboxylate (1.20 g, 2.77 mmol) in CH₂Cl₂ (16 mL) is added TFA (4 mL). The mixture is stirred at room temperature for 3 hr. The mixture is concentrated under reduced pressure and the residue is partitioned between ethyl acetate and saturated NaHCO₃ solution. The layers are separated and the aqueous layer is further extracted with ethyl acetate. The combined organic phases are washed with brine, and are dried (Na₂SO₄) and concentrated in vacuo to afford the title compound (1.20 g, >99%) which is used in the next step without purification. LCMS: 334.75 (M+H⁺).

Step 6: Synthesis of 10-Methyl-6-oxo-7,8,9,10-tetrahydro-6H-pyrido[3',2':4,5]pyrrolo[1,2-a][1,4]diazepine-2-carboxylic acid To a solution of diethyl 1-(4-aminobutan-2-yl)-1H-pyrrolo[2,3-b]pyridine-2,6-dicarboxylate (1.20 g, 3.60 mmol) in ethanol (35 mL) is added potassium carbonate (1.49 g, 10.8 mmol). The mixture is stirred at 60° C. for 16 h and is then cooled to room temperature. The ethanol is removed in vacuo and the aqueous mixture is acidified to pH 5 with 1N hydrochloric acid and is extracted with ethyl acetate. The combined organic phases are washed with brine, and are dried (Na₂SO₄) and concentrated in vacuo to afford the title compound as a yellow solid (500 mg, 54%). LCMS: (M+H⁺).

Intermediate H: cis-8,9-Dimethyl-6-oxo-6,7,8,9-tetrahydropyrido[3',2':4,5]pyrrolo[1,2-a]pyrazine-2-carboxylic acid Intermediate I: trans-8,9-Dimethyl-6-oxo-6,7,8,9-tetrahydropyrido[3',2':4,5]pyrrolo[1,2-a]pyrazine-2-carboxylic acid

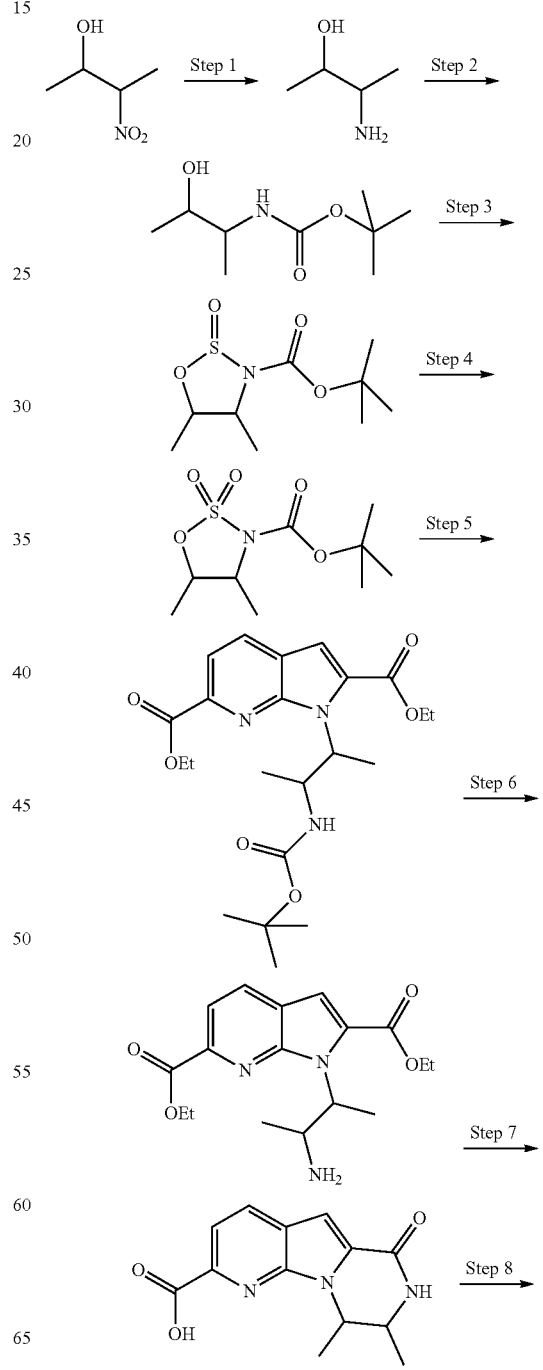

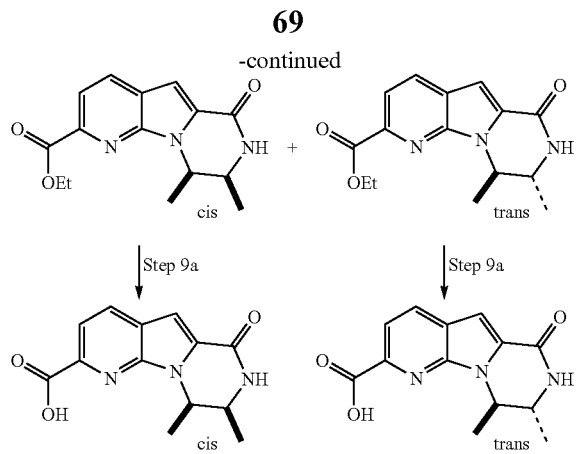

Step 1: Synthesis of 3-Aminobutan-2-ol

Ammonium formate (9.0 g, 142.9 mmol) is added to a solution of 3-nitro-butan-2-ol (2.5 g, 21.0 mmol) in methanol (20 mL). 10% Palladium on carbon (250 mg) is then added as a slurry in methanol. The reaction mixture is stirred at room temperature for 18 h. Then Celite is added and the mixture is filtered though a plug of more Celite. The solid is washed again with methanol and the filtrates are combined and concentrated to afford the crude title compound (2.42 g, >99%) which is used in the next step without purification.

Step 2: Synthesis of tert-Butyl (3-hydroxybutan-2-yl)carbamate

To a stirred solution of 3-aminobutan-2-ol (2.42 g, 21.7 mmol) in CH$_2$Cl$_2$ (20 mL) is added a solution of di-tert-butyl dicarbonate (4.7 g, 21.4 mmol) in CH$_2$Cl$_2$ (20 mL). The reaction mixture is stirred for 18 h and then the solution is washed with 1M NaHSO$_4$ and NaHCO$_3$. The organic layer is separated, dried (MgSO$_4$) and concentrated to afford the title compound (4.33 g, >99%) as a colorless oil which was used in the next step without purification.

Step 3: Synthesis of tert-Butyl 4,5-dimethyl-1,2,3-oxathiazolidine-3-carboxylate 2-oxide A stirred solution of thionyl chloride (4.1 mL, 56.8 mmol) in acetonitrile (30 mL) is cooled to −45° C. A solution of tert-butyl (3-hydroxybutan-2-yl)carbamate (4.3 g, 22.7 mmol) in acetonitrile (40 mL) is added by syringe over about 10 min, keeping the internal temperature below −40° C. When the addition is completed, 4-dimethylamino pyridine (278 mg, 2.3 mmol) is added. Then pyridine (9.2 mL, 114 mmol) is added dropwise by syringe, keeping the temperature below −40° C. The reaction mixture is stirred at −40° C. for 1 hr. Ethyl acetate (70 mL) is added to the suspension and the mixture is filtered at −35° C. The solid is washed with EtOAc and the filtrates are combined. Saturated Na$_2$HPO$_4$ solution (40 mL) is added and the mixture is stirred vigorously for 30 min. The organic layer is separated, washed with 1M NaHSO$_4$, dried (MgSO$_4$) and concentrated to afford the title compound (4.8 g, 90%) as an oil.

Step 4: Synthesis of tert-Butyl 4,5-dimethyl-1,2,3-oxathiazolidine-3-carboxylate 2,2-dioxide tert-Butyl 4,5-dimethyl-1,2,3-oxathiazolidine-3-carboxylate 2-oxide (4.7 g, 20.0 mmol) is dissolved in acetonitrile (50 mL) and H$_2$O (30 mL) is added. The reaction mixture is cooled to 0° C. and sodium periodate (6.4 g, 30.0 mmol) is added. After 5 min, the pH of the mixture is adjusted to 7-8 by addition of saturated Na$_2$HPO$_4$ solution. Then the solution of RuCl$_3$ (42 mg, 0.2 mmol) in H$_2$O (0.5 mL) is added. The pH of the reaction mixture is kept between 6 and 9 by addition of Na$_2$HPO$_4$ solution. After stirring for 2 h, H$_2$O (100 mL) is added and the pH is adjusted to 6 by addition of 2M HCl solution. The mixture is extracted with EtOAc and the organic layer is separated, washed with NaHCO$_3$ and brine. The aqueous layers are back extracted once with EtOAc. Then all organic layers are combined, dried (MgSO$_4$) and concentrated. Purification by flash column chromatography using a gradient elution of 5-80% ethyl acetate/hexanes affords the title compound (4.48 g, 89%).

Step 5: Synthesis of Diethyl 1-{3-[(tert-butoxycarbonyl)amino]butan-2-yl}-1H-pyrrolo[2,3-b]pyridine-2, 6-dicarboxylate To a solution of diethyl 1H-pyrrolo[2,3-b]pyridine-2,6-dicarboxylate (Intermediate D, 3.40 g, 13.0 mmol) in DMF (15 mL) cooled to 0° C. is added 60% sodium hydride in mineral oil (570 mg, 14.3 mmol). The mixture is stirred at 0° C. for 20 min after which a solution of tert-butyl 4,5-dimethyl-1,2,3-oxathiazolidine-3-carboxylate 2,2-dioxide (5.35 g, 14.3 mmol) in DMF (10 mL) is added. The mixture is stirred at 0° C. for 30 min after which the reaction was allowed to warm and stir at ambient temperature overnight. The reaction is quenched with H$_2$O and was stirred for 15 min. The mixture is extracted with ethyl acetate and the combined organic phases are washed with brine, and are dried (Na$_2$SO$_4$). The solvent is removed in vacuo and the crude material is purified via flash column chromatography using a gradient elution of 0-20% ethyl acetate/heptane to afford the title compound as a colorless oil (6.00 g, quantitative). LCMS: 434.83 (M+H$^+$).

Step 6: Synthesis of Diethyl 1-(3-aminobutan-2-yl)-1H-pyrrolo[2,3-b]pyridine-2,6-dicarboxylate To a solution of diethyl 1-{3-[(tert-butoxycarbonyl)amino]butan-2-yl}-1H-pyrrolo[2,3-b]pyridine-2,6-dicarboxylate (6.00 g, 13.8 mmol) in CH$_2$Cl$_2$ (20 mL) is added TFA (10 mL). The mixture is stirred at room temperature for 16 h. The mixture is concentrated under reduced pressure and the residue is partitioned between ethyl acetate and saturated NaHCO$_3$ solution. The resulting white solid was collected by filtration and dried in vacuo to afford the title compound (3.83 g, 83%). LCMS: 334.80 (M+H$^+$).

Step 7: Synthesis of 8,9-Dimethyl-6-oxo-6,7,8,9-tetrahydropyrido[3',2':4,5]pyrrolo[1,2-a]pyrazine-2-carboxylic acid To a solution of diethyl 1-(3-aminobutan-2-yl)-1H-pyrrolo[2,3-b]pyridine-2,6-dicarboxylate (3.83 g, 11.5 mmol) in ethanol (45 mL) is added potassium carbonate (4.76 g, 34.5 mmol). The mixture is stirred at room temperature for 64 h. The ethanol is removed in vacuo and the aqueous mixture is acidified to pH 6 with 1N aqueous HCl. The resulting solid is collected by filtration and dried in vacuo to afford the title compound as a white solid (2.00 g, 54%). LCMS: 260.67 (M+H$^+$).

Step 8: Synthesis of Ethyl cis-8,9-dimethyl-6-oxo-6, 7,8,9-tetrahydropyrido[3',2':4,5]pyrrolo[1,2-a]pyrazine-2-carboxylate and Ethyl trans-8,9-dimethyl-6-oxo-6,7,8,9-tetrahydropyrido[3',2':4,5]pyrrolo[1,2-a]pyrazine-2-carboxylate To a solution of 8,9-dimethyl-6-oxo-6,7,8,9-tetrahydropyrido[3',2':4,5]pyrrolo[1,2-a]pyrazine-2-carboxylic acid (1.62 g, 6.25 mmol) in ethanol (10 mL) is added thionyl chloride (2.28 mL, 31.2 mmol). The mixture is stirred at room temperature for 16 h. The ethanol is evaporated and the residue is partitioned between ethyl acetate and saturated $NaHCO_3$ solution. The layers are separated and the aqueous layer is further extracted with ethyl acetate. The combined organic phases are washed with brine, and are dried ($Na_2SO_4$). The solvent is removed in vacuo and the crude material is purified via flash column chromatography using a gradient elution of 50-100% ethyl acetate/heptane to afford the cis isomer (907 mg, 51%) and the trans isomer (658 mg, 37%) LCMS: 434.83 ($M+H^+$).

Step 9a: Synthesis of cis-8,9-Dimethyl-6-oxo-6,7,8,9-tetrahydropyrido[3',2':4,5]pyrrolo[1,2-a]pyrazine-2-carboxylic acid To a suspension of ethyl cis-8,9-dimethyl-6-oxo-6,7,8,9-tetrahydropyrido[3',2':4,5]pyrrolo[1,2-a]pyrazine-2-carboxylate (1.04 g, 3.62 mmol) in ethanol (30 mL) is added 1M aqueous NaOH (9.05 mL, 9.05 mmol). The reaction mixture is heated at 50° C. for 90 min and is cooled to room temperature. The ethanol is removed in vacuo and the aqueous mixture is acidified with 1N aqueous HCl. The resulting solid is collected by filtration and dried in vacuo to afford the title compound as a white solid (890 mg, 95%). LCMS: 260.65 ($M+H^+$).

Step 9b: Synthesis of trans-8,9-Dimethyl-6-oxo-6,7,8,9-tetrahydropyrido[3',2':4,5]pyrrolo[1,2-a]pyrazine-2-carboxylic acid To a suspension of ethyl trans-8,9-dimethyl-6-oxo-6,7,8,9-tetrahydropyrido[3',2':4,5]pyrrolo[1,2-a]pyrazine-2-carboxylate (702 mg, 2.44 mmol) in ethanol (20 mL) is added 1M aqueous NaOH solution (6.11 mL, 6.11 mmol). The reaction mixture is heated at 50° C. for 90 min and is cooled to room temperature. The ethanol is removed in vacuo and the aqueous mixture is acidified with 1N aqueous HCl. The resulting solid is collected by filtration and dried in vacuo to afford the title compound as a white solid (580 mg, 92%). LCMS: 260.64 ($M+H^+$).

Intermediate J: 9-Methyl-6-oxo-6,7,8,9-tetrahydropyrido[3',2':4,5]pyrrolo[1,2-a]pyrazine-2-carboxylic acid

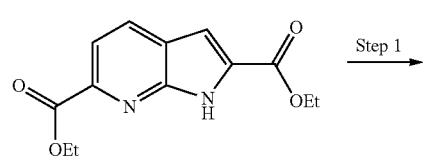

Step 1 →

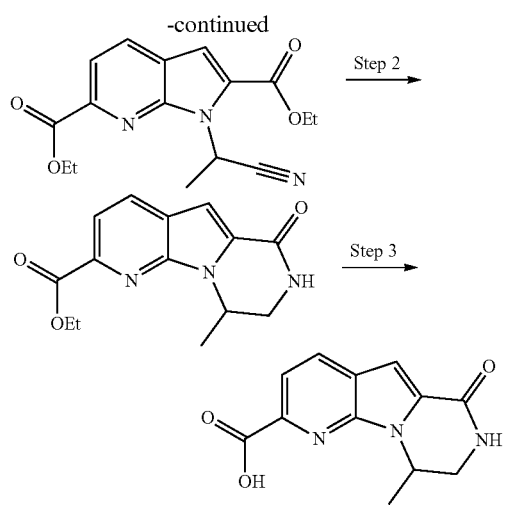

Step 1: Synthesis of Diethyl 1-(1-cyanoethyl)-1H-pyrrolo[2,3-b]pyridine-2,6-dicarboxylate To a solution of diethyl 1H-pyrrolo[2,3-b]pyridine-2,6-dicarboxylate (Intermediate D, 1.55 g, 5.91 mmol) in DMF (15 mL) is added potassium carbonate (2.45 g, 17.7 mmol), and the mixture is stirred at room temperature for 20 min. 2-bromopropionitrile (1.05 mL, 11.8 mmol) is added, the mixture is warmed to 80° C., and is stirred overnight. After being cooled to room temperature, the mixture is poured onto $H_2O$, and the aqueous layer is extracted with EtOAc (3×100 mL). The combined organic extracts are dried ($MgSO_4$), filtered, and concentrated. The crude material is purified via flash column chromatography using a gradient elution of 10-50% ethyl acetate/hexanes to afford the title compound as a bright yellow solid (809 mg, 43%).

Step 2: Synthesis of Ethyl 9-methyl-6-oxo-6,7,8,9-tetrahydropyrido[3',2':4,5]pyrrolo[1,2-a]pyrazine-2-carboxylate To a solution of diethyl 1-(1-cyanoethyl)-1H-pyrrolo[2,3-b]pyridine-2,6-dicarboxylate (807 mg, 2.56 mmol) in methanol/THF (14 mL, 1:1 v/v) at 0° C. is added sodium borohydride (968 mg, 25.6 mmol). The cold bath is removed and the reaction mixture is stirred for 30 min, at which point the reaction vessel is sealed and warmed to 60° C. After being stirred for 4 h, the mixture is cooled to room temperature and diluted with EtOAc. The organic phase is washed twice with 1Ma aqueous $NaHSO_4$ and once with brine, is dried ($Na_2SO_4$), filtered and concentrated to provide the title compound as a light yellow solid (298 mg, 43%).

Step 3: Synthesis of 9-Methyl-6-oxo-6,7,8,9-tetrahydropyrido[3',2':4,5]pyrrolo[1,2-a]pyrazine-2-carboxylic acid To a suspension of 9-methyl-6-oxo-6,7,8,9-tetrahydropyrido[3',2':4,5]pyrrolo[1,2-a]pyrazine-2-carboxylate (298 mg, 1.09 mmol) in methanol (0.5 mL) is added a solution of 2M aqueous NaOH (2.2 mL, 4.4 mmol). The mixture is warmed to 60° C. and stirred for 2 h, at which point it is acidified with concentrated HCl. The volume of the mixture is reduced to approximately 5 mL, and it is chilled to 0° C. The resultant suspension is filtered and the solid is washed with H₂O and hexanes, to provide the title compound as a light yellow solid (135 mg, 51%).

Intermediate K: (9R)-9-Methyl-6-oxo-6,7,8,9-tetrahydropyrido[3',2':4,5]pyrrolo[1,2-a]pyrazine-2-carboxylic acid

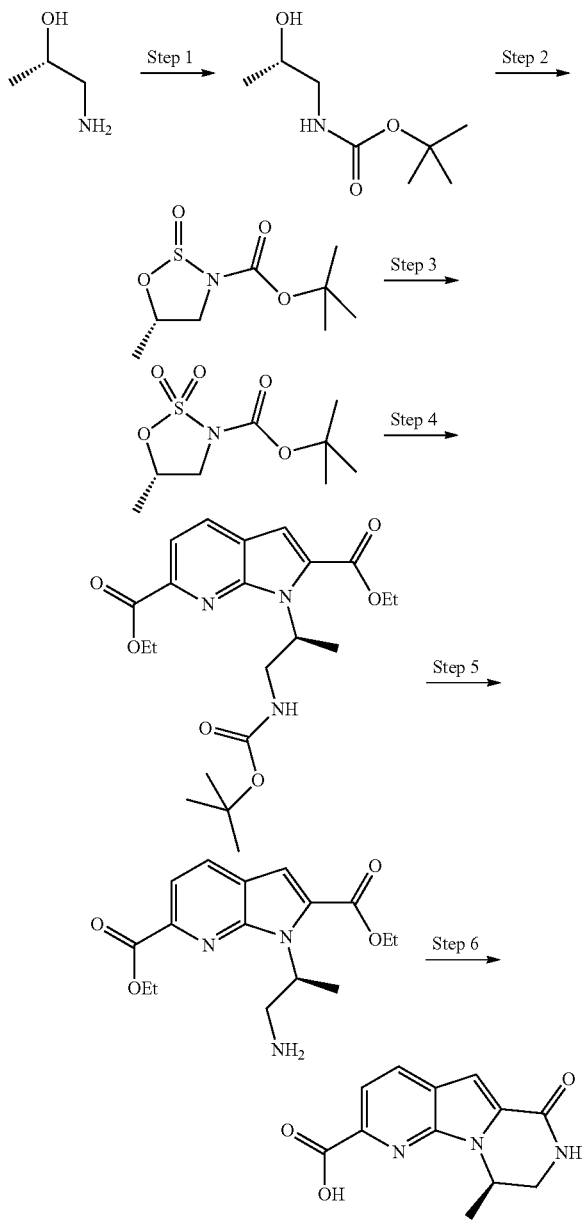

Step 1: Synthesis of tert-Butyl [(2S)-2-hydroxypropyl]carbamate

To a stirred solution of (S)-1-Aminopropan-2-ol (2.0 g, 26.6 mmol) in CH₂Cl₂ (50 mL) is added a solution of di-tert-butyl dicarbonate (6.1 g, 28 mmol) in CH₂Cl₂ (50 mL). The reaction mixture is stirred for 18 h. The solution is washed with citric acid and NaHCO₃, dried (Na₂SO₄) and evaporated to afford the title compound (5.1 g, >99%) as a colorless oil.

Step 2: Synthesis of tert-Butyl (5S)-5-Methyl-1,2,3-oxathiazolidine-3-carboxylate 2-oxide A stirred solution of thionyl chloride (4.8 mL, 66.3 mmol) in acetonitrile (30 mL) is cooled down to −45° C. and a solution of tert-butyl [(2S)-2-hydroxypropyl]carbamate (5.1 g, 26.6 mmol) in acetonitrile (40 mL) is added by an addition funnel over 20 min, keeping the internal temperature below −40° C. DMAP (324 mg, 2.6 mmol) is added followed by the dropwise addition of pyridine (10.7 mL, 133.7 mmol), keeping the temperature below −40° C. The addition takes 1.5 h. Ethyl acetate (100 mL) is added to the suspension. The mixture is filtered at −35° C. to remove the solid and the solid is washed with EtOAc before it is discarded. Then the filtrates are combined, and sat. Na₂HPO₄ solution (40 mL) is added. Again the mixture is stirred vigorously for 30 min. Then the organic layer is separated, washed with 1M aqueous NaHSO₄ to remove residual pyridine, dried (Na₂SO₄) and concentrated to afford a clear oil. The residue was taken up in diethyl ether, a small amount of insoluble material was removed and the filtrate was concentrated to afford the title compound (5.7 g, 97%) as an oil which was used in the next step without purification.

Step 3: Synthesis of tert-Butyl (5S)-5-methyl-1,2,3-oxathiazolidine-3-carboxylate 2,2-dioxide To a solution of tert-butyl (5S)-5-methyl-1,2,3-oxathiazolidine-3-carboxylate 2-oxide (5.7 g, 25.8 mmol) in acetonitrile (60 mL) and H₂O (30 mL) is added sodium periodate (8.3 g, 38.7 mmol). After 5 min, a few crystals of RuCl₃ are added. The reaction is stirred for 3 hours and the resulting thick slurry is diluted with H₂O (100 mL) and ethyl acetate (20 mL) and passed through a bed of Celite, rinsing with additional EtOAc. The filtrate is concentrated to remove the organic solvents and the resulting solid is isolated by filtration to afford the title compound (6.0 g, 97%).

Step 4: Synthesis of Diethyl 1-{(2S)-1-[(tert-butoxycarbonyl)amino]propan-2-yl}-1H-pyrrolo[2,3-b]pyridine-2,6-dicarboxylate To a suspension of 60% sodium hydride in mineral oil (503 mg, 12.6 mmol) in DMF (10 mL) cooled to 0° C. is added a solution of diethyl 1H-pyrrolo[2,3-b]pyridine-2,6-dicarboxylate (Intermediate D, 3.00 g, 11.4 mmol) in DMF (10 mL), dropwise. The mixture is stirred at 0° C. for 30 min after which a solution of tert-butyl (5S)-5-methyl-1,2,3-oxathiazolidine-3-carboxylate 2,2-dioxide (2.71 g, 11.4 mmol) in DMF (10 mL) is added. The mixture is allowed to warm and stir at room temperature for 16 h. The reaction is quenched with H₂O and is stirred for 15 min. The mixture is extracted with ethyl acetate and the combined organic phases are washed with brine and are dried (Na₂SO₄). The solvent is removed in vacuo and the crude material is purified via flash column chromatography using a gradient elution of 0-30% ethyl acetate/heptane to afford the title compound (3.00 g, 63%). LCMS: 442.86 (M+Na⁺).

Step 5: Synthesis of Diethyl 1-[(2S)-1-aminopropan-2-yl]-1H-pyrrolo[2,3-b]pyridine-2,6-dicarboxylate To a solution of diethyl 1-{(2S)-1-[(tert-butoxycarbonyl)amino]propan-2-yl}-1H-pyrrolo[2,3-b]pyridine-2,6-dicarboxylate (3.00 g, 7.15 mmol) in CH₂Cl₂ (20 mL) is added TFA (10 mL). The mixture is stirred at room temperature for 3 hr then is concentrated under reduced pressure. The residue is taken up in ethyl acetate and is washed with brine, is dried (Na$_2$SO$_4$) and concentrated in vacuo to afford the title compound (2.17 g) which is used in the next step without purification.

Step 6: Synthesis of (9R)-9-Methyl-6-oxo-6,7,8,9-tetrahydropyrido[3',2':4,5]pyrrolo[1,2-a]pyrazine-2-carboxylic acid To a solution of diethyl 1-[(2S)-1-aminopropan-2-yl]-1H-pyrrolo[2,3-b]pyridine-2,6-dicarboxylate (2.17 g, 6.80 mmol) in ethanol (40 mL) is added potassium carbonate (2.82 g, 20.4 mmol). The mixture is stirred at 60° C. for 16 h and is then cooled to room temperature. The ethanol is removed in vacuo and the aqueous mixture is acidified to pH 5 with 1N aqueous hydrochloric acid. The resulting solid is collected by filtration and dried in vacuo to afford the title compound as a pale yellow solid (1.40 g, 84%). LCMS: 246.64 (M+H+).

Intermediate L: (9S)-9-Methyl-6-oxo-6,7,8,9-tetrahydropyrido[3',2':4,5]pyrrolo[1,2-a]pyrazine-2-carboxylic acid

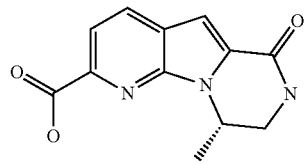 [SMILES: C[C@H]1CNC(=O)c2cc3ccc(C(=O)O)nc3n21]

(9S)-9-Methyl-6-oxo-6,7,8,9-tetrahydropyrido[3',2':4,5]pyrrolo[1,2-a]pyrazine-2-carboxylic acid is synthesized using the similar procedure used to prepare (9R)-9-methyl-6-oxo-6,7,8,9-tetrahydropyrido[3',2':4,5]pyrrolo[1,2-a]pyrazine-2-carboxylic acid (Intermediate J), replacing (S)-1-Aminopropan-2-ol with (R)-1-Aminopropan-2-ol in Step 1.

Intermediate M: 1-(Propan-2-yl)-1H-benzimidazol-2-amine hydrobromide

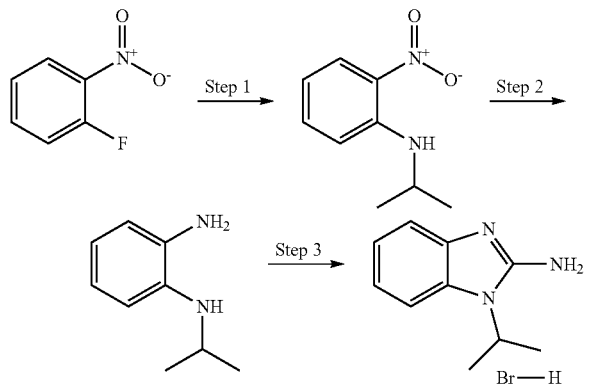

Step 1: Synthesis of 2-Nitro-N-(propan-2-yl)aniline

To a solution of 2-fluoronitrobenzene (0.5 mL, 4.7 mmol) in DMSO (10 mL) is added isopropylamine (0.6 mL, 7.1 mmol), followed by Hunig's base (1.2 mL, 7.1 mmol). The reaction flask is sealed and heated to 80° C. overnight. The reaction is then cooled to room temperature and poured over ice H$_2$O and extracted ethyl acetate. The organic layer is washed with H$_2$O, brine, dried (Na$_2$SO$_4$) and concentrated to afford the title compound (828 mg, 97%) as an orange oil.

Step 2: Synthesis of N-(Propan-2-yl)benzene-1,2-diamine

To a solution of 2-nitro-N-(propan-2-yl)aniline (828 mg, 4.6 mmol) in ethanol (10 mL) under a nitrogen atmosphere is carefully added 20% palladium on carbon (50 mg, Degussa type) followed by ammonium formate (1.4 g, 23 mmol) and the reaction is stirred for 16 h. The suspension is carefully filtered through a bed of Celite and the filter cake is rinsed with additional ethanol (10 mL). The filtrate is concentrated and the residue is partitioned between H$_2$O and ethyl acetate. The organic layer is dried (Na$_2$SO$_4$) and concentrated and the residue is purified by chromatography through a short bed of silica gel using 5% methanol/CH$_2$Cl$_2$ affords the title compound (552 mg, 80%) as an oil.

Step 3: Synthesis of 1-(Propan-2-yl)-1H-benzimidazol-2-amine; hydrobromide

To a solution of N-(propan-2-yl)benzene-1,2-diamine (552 mg, 3.4 mmol) in ethanol (10 mL) is added a 3M solution of cyanogen bromide (1.35 mL, 4.04 mmol) in CH$_2$Cl$_2$. The reaction is stirred overnight and then concentrated. The crude residue is triturated with diethyl ether and the suspension is filtered to afford the title compound (870 mg, 92%) as a purple solid.

Intermediate N: 3-(1-Trityl-1H-imidazol-4-yl)aniline

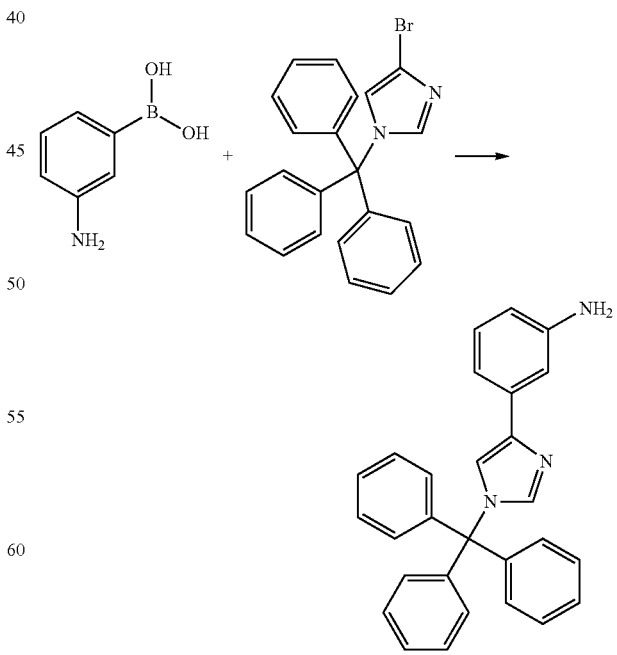

(3-Aminophenyl)boronic acid (1.0 g, 7.3 mmol), 4-bromo-1-trityl-1H-imidazole (2.8 g, 7.3 mmol), tri-t-butylphosphonium tetrafluoroborate (424 mg, 1.5 mmol) and KF (1.4 g, 24.1 mmol) are added into dry THF (20 mL) and argon is bubbled through the mixture for 10 min. Tris-(dibenzylideneacetone)dipalladium(0) (669 mg, 0.7 mmol) is added and the reaction mixture is sealed and heated at 60° C. for 16 hrs. The solid is filtered and the filtrate is diluted with EtOAc (250 mL). The solution is washed with $H_2O$ (3×100 mL), brine (100 mL), dried ($Na_2SO_4$) and concentrated. The crude product is purified by flash column chromatography using methanol/$CH_2Cl_2$ to afford the title compound (1.1 g, 36%).

Intermediate O: 4-Amino-N-cyclopentyl-1-methyl-1H-imidazole-2-carboxamide trifluoroacetate

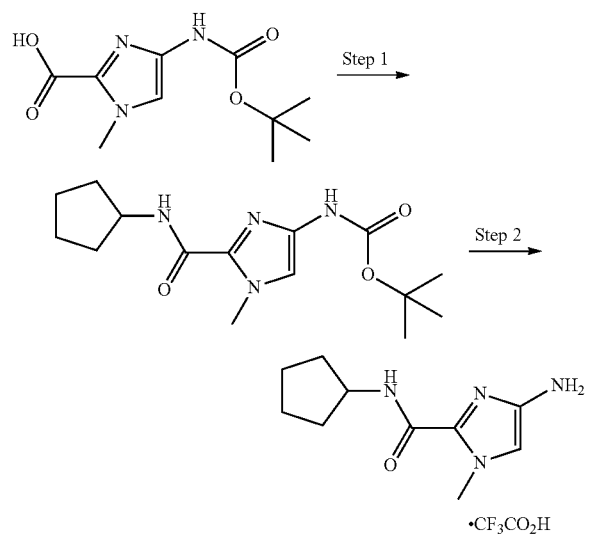

Step 1: Synthesis of tert-butyl[2-(cyclopentylcarbamoyl)-1-methyl-1H-imidazol-4-yl]carbamate To a stirred suspension of 4-[(tert-butoxycarbonyl)amino]-1-methyl-1H-imidazole-2-carboxylic acid (724 mg, 3.0 mmol) in DMF (6 mL) is added TBTU (1.16 g, 3.6 mmol). After 15 min cyclopentylamine (0.44 mL, 4.5 mmol) is added. After 20 h an additional portion of cyclopentylamine (0.44 mL, 4.5 mmol) is added, and stifling continued for a further 24 h. The mixture is diluted with EtOAc and washed in turn with 1M aqueous $NaHSO_4$, $Na_2CO_3$ and brine. The organic layer is dried ($MgSO_4$) and evaporated. The crude material is purified by column chromatography using a gradient of 10-100% EtOAc/heptane to afford the title compound (345 mg, 37%).

Step 2: Synthesis of 4-Amino-N-cyclopentyl-1-methyl-1H-imidazole-2-carboxamide trifluoroacetate To a stirred solution of tert-butyl[2-(cyclopentylcarbamoyl)-1-methyl-1H-imidazol-4-yl]carbamate (88 mg, 0.29 mmol) in $CH_2Cl_2$ (1 mL) is added TFA (1 mL). The solution is stirred at room temperature for 1 h and evaporated. $CH_2Cl_2$ is evaporated from the residue twice to remove excess TFA, to afford the title compound as the trifluoroacetate salt as an oil, which is used immediately in the amide coupling step without purification.

Intermediate P: 1-(Tetrahydrofuran-3-ylmethyl)-1H-pyrazolo[3,4-b]pyridin-5-amine

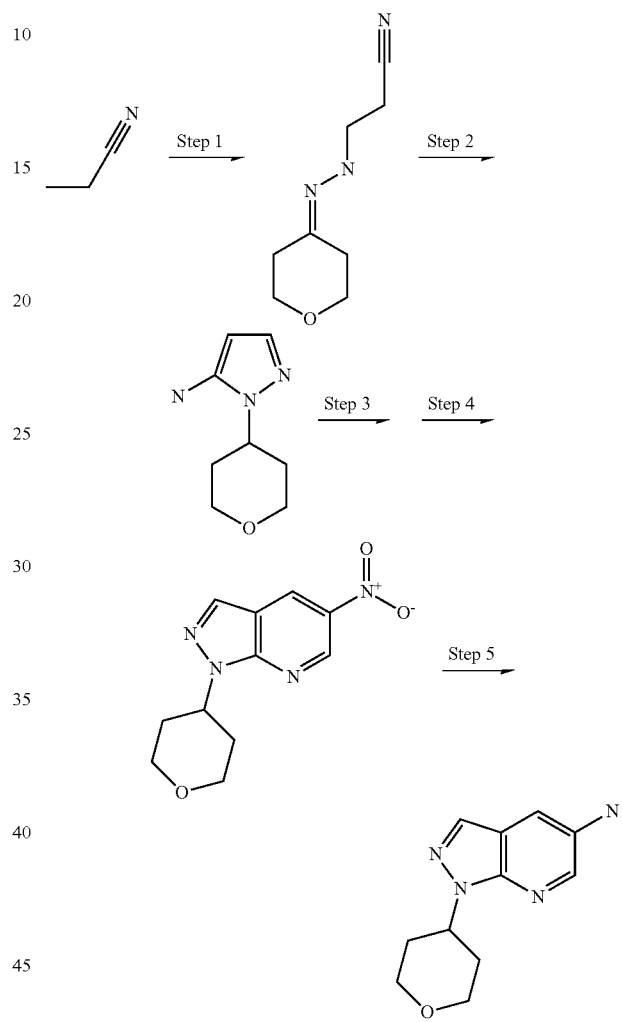

Step 1: Synthesis of 3-[2-(Tetrahydro-4H-pyran-4-ylidene)hydrazinyl]propanenitrile To a solution of propanenitrile (5 g, 94 mmol) in ethanol at 0° C. is added hydrazine hydrate (4.6 g, 91 mmol), dropwise. The reaction mixture is stirred at ambient temperature for 16 h after. The mixture is cooled to 0° C. and tetrahydropyran-4-one (9 g, 90 mmol) is added slowly. The reaction continues to stir at ambient temperature for an additional 5 h. The solvent is evaporated under reduced pressure to afford the title compound as a highly viscous liquid (15 g, >99%) which is used in the next step without purification.

Step 2: Synthesis of 1-(Tetrahydro-2H-pyran-4-yl)-1H-pyrazol-5-amine

To a solution of 3-[2-(tetrahydro-4H-pyran-4-ylidene)hydrazinyl]propanenitrile (5 g, 30 mmol) in 1-propanol (50 mL)

is added NaOH (29 mg, 0.74 mmol) and reaction mixture is heated at reflux for 16 h. The solvent is evaporated under reduced pressure and the residue is filtered through neutral alumina eluting with ethyl acetate to afford the title compound as a yellow solid (1.6 g, 32%) which is used in the next step without purification.

Step 3: Synthesis of 5-Nitro-1-(tetrahydro-2H-pyran-4-yl)-1H-pyrazolo[3,4-b]pyridine To a solution of 1-(tetrahydro-2H-pyran-4-yl)-1H-pyrazol-5-amine (1.6 g, 9.6 mmol) in 70% acetic acid (15 mL) is added nitromalonaldehyde (1.3 g, 9.6 mmol) and the reaction mixture is heated to 108° C. for 3 h. The solvent is evaporated under reduced pressure and the residue is purified by flash column chromatography using a gradient of 20% ethyl acetate/petroleum ether to afford the title compound as a pale yellow solid (1.6 g, 70%).

Step 4: Synthesis of 1-(Tetrahydro-2H-pyran-4-yl)-1H-pyrazolo[3,4-b]pyridin-5-amine Iron (2.41 g, 42.3 mmol) and ammonium chloride (2.58 g, 48.4 mmol) are added to a solution of 5-nitro-1-(tetrahydro-2H-pyran-4-yl)-1H-pyrazolo[3,4-b]pyridine (3 g, 12 mmol) in ethanol/THF/H$_2$O (4:2:1, 35 mL). The mixture is heated at 100° C. for 2 h. The iron is removed by filtration through pad of Celite® and the filtrate was evaporated under reduced pressure. The residue is purified by flash column chromatography using a gradient of 70% ethyl acetate/petroleum ether to afford the title compound as an off-white solid (2.85 g, 93%).

Intermediate Q: 1-(Tetrahydrofuran-3-ylmethyl)-1H-pyrazolo[3,4-b]pyridin-5-amine

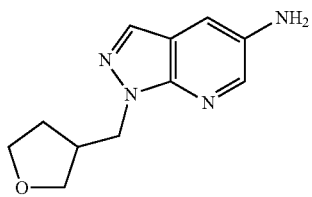 [SMILES: Nc1cnc2c(cnn2CC2CCOC2)c1]

1-(Tetrahydro-furan-3-ylmethyl)-1H-pyrazolo[3,4-b]pyridin-5-ylamine is synthesized using a similar procedure used to prepare (1-(Tetrahydro-pyran-4-yl)-1H-pyrazolo[3,4-b]pyridin-5-ylamine (Intermediate P), replacing tetrahydropyran-4-one with tetrahydro-furan-3-carbaldehyde in Step 1.

Intermediate R: 5-Chloro-7-(morpholin-4-ylmethyl)-1H-benzimidazol-2-amine dihydrobromide

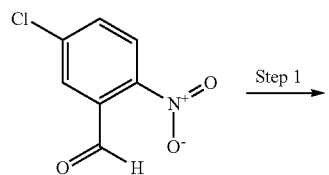

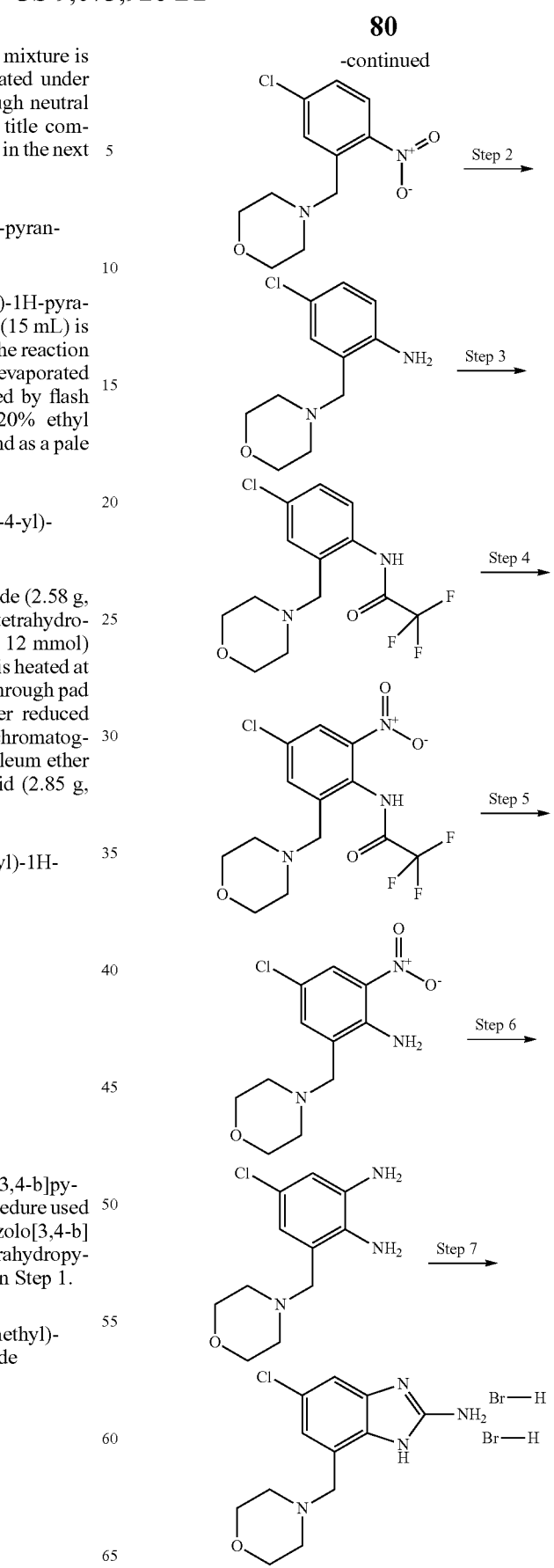

Step 1: Synthesis of 4-(5-Chloro-2-nitrobenzyl)morpholine

To a solution of morpholine (2.8 mL, 32.3 mmol) in tetrahydrofuran (100 mL) is added 5-chloro-2-nitrobenzaldehyde (5 g, 26.9 mmol) followed by sodium triacetoxyborohydride (11.4 g, 53.9 mmol) and HOAc (3.2 mL, 53.9 mmol) and the reaction is stirred overnight. The reaction is poured into a saturated aqueous $Na_2CO_3$ solution and extracted with ethyl acetate. The combined extracts are washed with $H_2O$, brine, dried ($Na_2SO_4$) and concentrated to afford a clear oil. The residue is taken up in 1N aqueous HCl and removed insoluble material by filtration. The filtrate is neutralized with 2M aqueous $K_2CO_3$ and partitioned into ethyl acetate. The organic layer is dried ($Na_2SO_4$) and concentrated to afford the title compound (5.1 g, 74%) as an oil.

Step 2: Synthesis of 4-Chloro-2-(morpholin-4-ylmethyl)aniline

To a solution of 4-(5-chloro-2-nitrobenzyl)morpholine (5.1 g, 19.9 mmol) in HOAc (75 mL) is carefully added zinc dust (3.9 g, 59.6 mmol). After 2 hours, the reaction is filtered through a bed of Celite and the filtrate is concentrated to remove most of the HOAc. The residue is then taken up in 2M aqueous $K_2CO_3$ and extracted with ethyl acetate. The organic layer is dried ($Na_2SO_4$) and concentrated to afford a brown oil. The crude material is purified by flash column chromatography using a gradient of 0-5% methanol/$CH_2Cl_2$ to afford the title compound (4.0 g, 12.4 mmol, 70% purity).

Step 3: Synthesis of N-[4-Chloro-2-(morpholin-4-ylmethyl)phenyl]-2,2,2-trifluoroacetamide To a solution of 4-chloro-2-(morpholin-4-ylmethyl)aniline (4.0 g, 12.4 mmol) in 1,4-dioxane (75 mL) cooled to 0° C. is added trifluoroacetic anhydride (2.4 mL, 17.4 mmol) and the reaction is warmed to room temperature overnight. The reaction is diluted with diethyl ether and the insoluble material is removed by filtration. The filtrate is concentrated and partitioned between 2M aqueous $K_2CO_3$ and diethyl ether. The organic layer is separated, dried over ($Na_2SO_4$) and concentrated to afford the title compound (3.8 g, 95%) as an orange oil which is used in the next step without purification.

Step 4: Synthesis of N-[4-Chloro-2-(morpholin-4-ylmethyl)-6-nitrophenyl]-2,2,2-trifluoroacetamide To a solution of N-[4-chloro-2-(morpholin-4-ylmethyl)phenyl]-2,2,2-trifluoroacetamide (3.8 g, 11.8 mmol) in concentrated sulfuric acid (35 mL) cooled to 0° C. is added potassium nitrate (1.4 g, 14.1 mmol). The reaction is slowly warmed to room temperature over a period of 2 h and then poured into ice $H_2O$. The mixture is neutralized with saturated aqueous $K_2CO_3$ and the resulting solid is collected by filtration to afford the title compound (3.6 g, 82%).

Step 5: Synthesis of 4-Chloro-2-(morpholin-4-ylmethyl)-6-nitroaniline

To a solution of N-[4-chloro-2-(morpholin-4-ylmethyl)-6-nitrophenyl]-2,2,2-trifluoroacetamide (3.6 g, 9.6 mmol) in ethanol (60 mL) is added a 10% aqueous NaOH solution (60 mL, 150 mmol). The reaction is heated to 80° C. for 3 hours and then left at room temperature overnight. Most of the ethanol is removed under reduced pressure and the resulting solid is isolated by filtration to afford the title compound (2 g, 77%).

Step 6: Synthesis of 5-Chloro-3-(morpholin-4-ylmethyl)benzene-1,2-diamine

To a solution of tin (II) chloride (1.1 g, 6 mmol) in concentrated HCl (1.5 mL) is added 4-chloro-2-(morpholin-4-ylmethyl)-6-nitroaniline (543 mg, 2 mmol) as a solution in concentrated HCl (1 mL). The reaction is stirred for 1 hour. The thick slurry is filtered and the filter cake rinsed with HCl. The filter cake is dissolved in $H_2O$ (10 mL) and treated with 2M aqueous $K_2CO_3$ and extracted with $CH_2Cl_2$. The organic layer is separated, dried ($Na_2SO_4$) and concentrated to afford the title compound (458 mg, 95%) as an oil.

Step 7: 5-Chloro-7-(morpholin-4-ylmethyl)-1H-benzimidazol-2-amine dihydrobromide To a solution of 5-chloro-3-(morpholin-4-ylmethyl)benzene-1,2-diamine (458 mg, 1.9 mmol) in ethanol (5 mL) is added a 48% aqueous HBr solution (0.21 mL, 1.9 mmol) followed by a 3M solution of cyanogen bromide (0.95 mL, 2.8 mmol) in $CH_2Cl_2$. The reaction is stirred at room temperature for 4 h and is diluted with diethyl ether. The resulting solid is isolated by filtration to afford the title compound as the dihydrobromide salt (595 mg, 73%).

Intermediate S: 1-(Pyridin-4-ylmethyl)-1H-pyrazol-4-amine

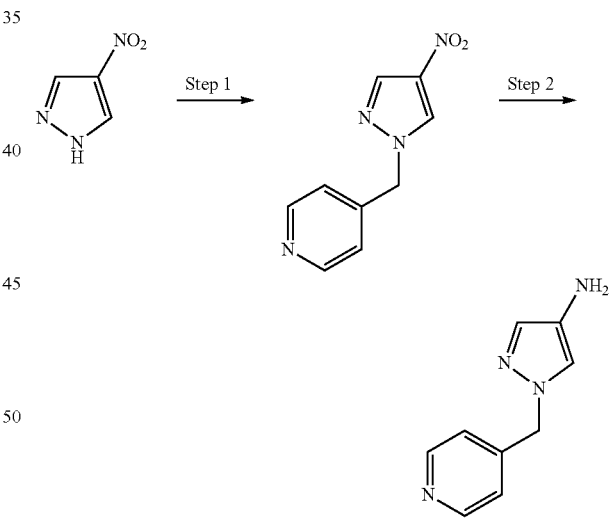

Step 1. 4-[(4-Nitro-1H-pyrazol-1-yl)methyl]pyridine

To a stirred solution of 4-nitro-1H-pyrazole (211 mg, 1.87 mmol), pyridine-4-methanol (0.28 ml, 2.56 mmol), and triphenylphosphine (538 mg, 2.05 mmol) in THF (10 ml) under nitrogen is added di-t-butyl azodicarboxylate (472 mg, 2.05 mmol) over 3 min. The reaction mixture was stirred at room temperature for 16 h. The mixture is concentrated and purified via flash column chromatography using a gradient elution of 0-3% $CH_2Cl_2$/methanol to afford the desired compound as a yellow oil (247 mg, 65%).

Step 2. Synthesis of 1-(Pyridin-4-ylmethyl)-1H-pyrazol-4-amine

A solution of 4-[(4-nitro-1H-pyrazol-1-yl)methyl]pyridine (247 mg, 1.21 mmol) in methanol (10 mL) is hydrogenated over 10% palladium on carbon (30 mg) under balloon pressure for 3 h. The mixture is filtered through Celite® and the filtrate is concentrated under reduced pressure. The residue is purified via flash column chromatography using a gradient elution of 0-10% $CH_2Cl_2$/methanol to afford the title compound as a brown oil (198 mg, 94%).

Intermediate T: 5-Phenyl-1,2-oxazol-3-amine

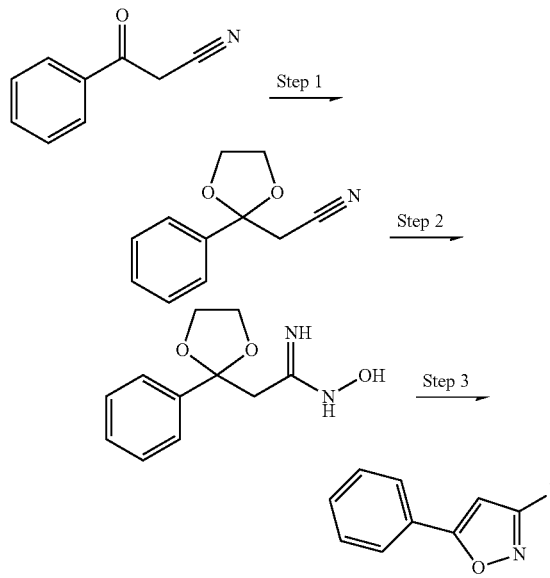

Step 1: Synthesis of (2-Phenyl-1,3-dioxolan-2-yl)acetonitrile

To a solution of 3-oxo-3-phenylpropanenitrile (10 g, 69 mmol) and PTSA (27 mg, 1.37 mmol) in toluene (120 mL) is added ethylene glycol (120 mL, 2057 mmol). The azeotropic mixture is heated at 150° C. for 14 h. The solvent is evaporated under reduced pressure and the residue is washed with 10% aqueous NaOH solution. The aqueous layer is extracted with diethyl ether (2×100 mL) and the combined organic layers are dried ($Na_2SO_4$) and evaporated to provide the crude compound. The crude material is purified over neutral alumina eluting with 1% of ethyl acetate/hexane to afford the title compound as an off-white solid (10 g, 77%).

Step 2: Synthesis of N-Hydroxy-2-(2-phenyl-1,3-dioxolan-2-yl)-ethanimidamide NaOH (3.1 g, 77 mmol) is added to hydroxylamine hydrochloride (5.2 g, 75 mmol) at 0° C. and is stirred for 15 min. A solution of (2-phenyl-1,3-dioxolan-2-yl)acetonitrile (7 g, 37 mmol) in methanol (25 mL) is added dropwise to the reaction mixture at 0° C. The reaction mixture is allowed to warm to room temperature and is heated at 90° C. for 16 h. The solvent was evaporated under reduced pressure to afford the title compound as a brown solid (7 g, 85%) which is used in the next step without purification.

Step 3: Synthesis of 5-Phenyl-1,2-oxazol-3-amine

Ethanol (125 mL) and $H_2O$ (25 mL) are added to N-hydroxy-2-(2-phenyl-1,3-dioxolan-2-yl)ethanimidamide (7 g, 32 mmol). The pH is adjusted to 1 with the addition concentrated HCl and the reaction mixture is heated at 90° C. for 2 h. The solvent is evaporated to dryness and the resulting residue is neutralized using phosphate buffer. The mixture is extracted with ethyl acetate and the combined organic phases are dried ($Na_2SO_4$) and concentrated in vacuo. The crude residue is purified over neutral alumina eluting with 30% ethyl acetate/hexane to afford the title compound as an off-white solid (1.7 g, 34%).

| Structure | Intermediate |
|---|---|
| 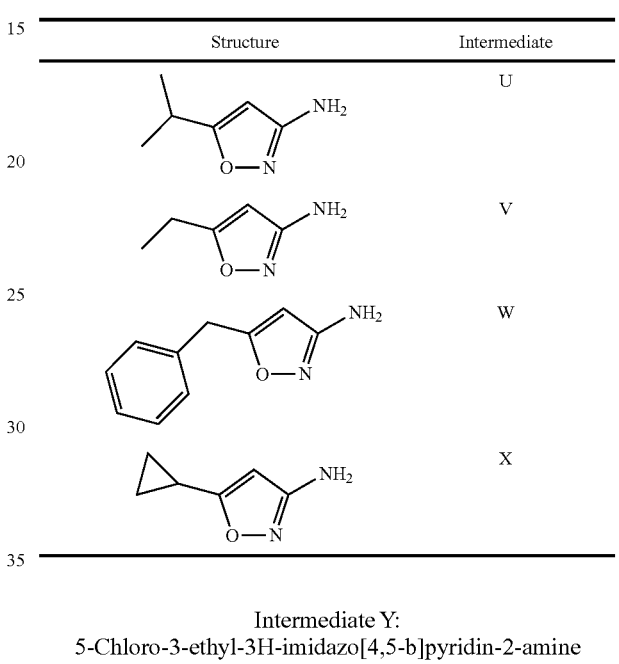 | U |
| 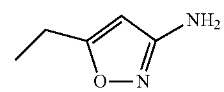 | V |
| 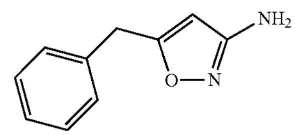 [SMILES: Nc1cc(Cc2ccccc2)on1] | W |
| 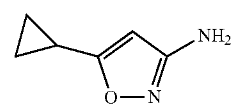 | X |

Intermediate Y:
5-Chloro-3-ethyl-3H-imidazo[4,5-b]pyridin-2-amine

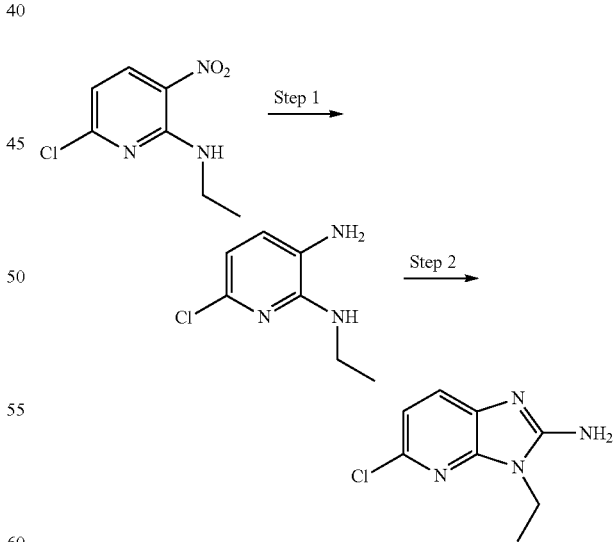

Step 1. Synthesis of 6-Chloro-N~2~-ethylpyridine-2,3-diamine

To a solution of 6-chloro-N-ethyl-3-nitropyridin-2-amine (1.82 g, 9.04 mmol) in ethanol (20 mL) is added iron powder (2.52 g, 45.2 mmol) and a solution of ammonium chloride (2.42 g, 45.2 mmol) in H₂O (8 mL). The mixture is heated in a microwave reactor at 140° C. for 30 min. The mixture is diluted with EtOAc, filtered and evaporated to afford the title compound as a brown oil (1.55 g, 100%) which was used in the next step without purification.

Step 2. Synthesis of 5-Chloro-3-ethyl-3H-imidazo[4,5-b]pyridin-2-amine

To a solution of 6-chloro-N~2~-ethylpyridine-2,3-diamine (401 mg, 2.34 mmol) in ethanol (10 mL) is added a 3M solution of cyanogen bromide in CH₂Cl₂ (0.93 mL, 2.8 mmol) and the resulting solution is stirred for 6 h at room temperature. The solution is basified with ammonia in methanol and evaporated. The residue is purified via flash column chromatography using a gradient elution of 0-15% CH₂Cl₂/methanol containing 1% NH₄OH to afford the title compound (212 mg, 46%).

Intermediate Z
3-Ethyl-3H-imidazo[4,5-b]pyridin-2-amine

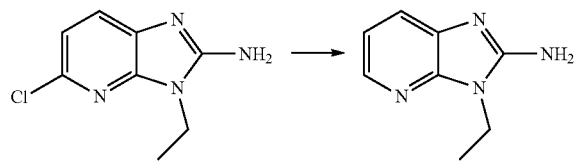

Ammonium formate (1.55 g, 24.6 mmol) is added to a solution of 5-chloro-3-ethyl-3H-imidazo[4,5-b]pyridin-2-amine (410 mg, 2.09 mmol) in ethanol (10 mL) containing 10% palladium on carbon (40 mg). The mixture is stirred at room temperature for 16 h. The reaction is filtered, concentrated under reduced pressure and the residue is purified via flash column chromatography using a gradient elution of 0-10% CH₂Cl₂/methanol to afford the title compound (192 mg, 57%).

Intermediate AA: 3-Benzyl-1,2-oxazol-5-amine

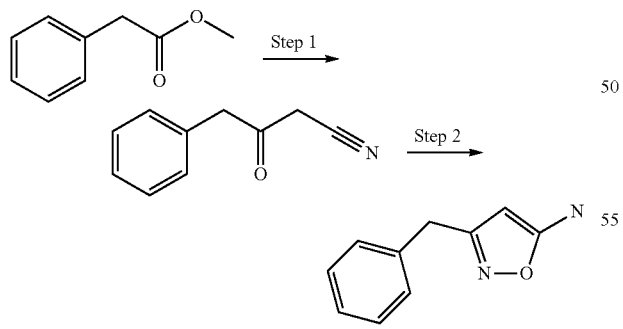

Step 1: Synthesis of 3-Oxo-4-phenylbutanenitrile

To a suspension of 60% sodium hydride in mineral oil (1.00 g, 25.0 mmol) in THF (40 mL) at reflux is added a solution of methyl phenylacetate (2.50 g, 16.6 mmol) and anhydrous acetonitrile (1.74 mL, 33.3 mmol) in THF (40 mL), dropwise. The mixture is stirred at reflux for 6 h, then cooled to room temperature and stirred an additional 16 h. The reaction is quenched with H₂O and is stirred for 10 min, after which the mixture is diluted with ethyl acetate and saturated aqueous NaHCO₃ solution. The layers are separated and the aqueous layer is extracted with ethyl acetate. The organic layers are washed with brine and dried (Na₂SO₄). The solvent is removed in vacuo and the crude material is purified via flash column chromatography using a gradient elution of 0-40% ethyl acetate/heptane to afford the title compound as a yellow oil (690 mg, 26%). LCMS: 160.20 (M+H⁺).

Step 2: Synthesis of 3-Benzyl-1,2-oxazol-5-amine

To a solution of 3-oxo-4-phenylbutanenitrile (690 mg, 4.34 mmol) in ethanol (25 mL) is added pyridine (4.91 mL, 60.7 mmol) and hydroxylamine hydrochloride (301 mg, 4.34 mmol). The reaction mixture is allowed to stir at room temperature 84 h. The mixture is diluted with ethyl acetate and 1M aqueous NaOH solution. The layers are separated and the aqueous layer is extracted with ethyl acetate. The organic layers are washed with brine, dried (Na₂SO₄), and the solvent is removed in vacuo to afford the title compound as a yellow solid (702 mg, 93%). LCMS: 175.20 (M+H⁺).

Example 1

1-Oxo-N-(pyridin-3-yl)-2,3,4,5-tetrahydro-1H-[1,4]diazepino[1,2-a]benzimidazole-8-carboxamide

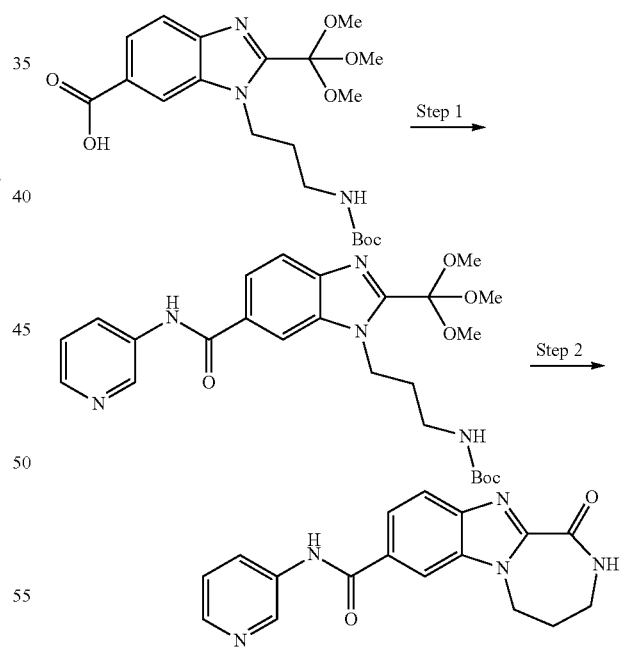

Step 1: Synthesis of tert-Butyl {3-[6-(pyridin-3-yl-carbamoyl)-2-(trimethoxymethyl)-1H-benzimidazol-1-yl]propyl}carbamate A solution of 1-(3-tert-butoxycarbonylamino-propyl)-2-trimethoxymethyl-3H-benzimidazole-5-carboxylic acid (Intermediate A, 70 mg, 0.17 mmol) and PyBOP (95 mg, 0.18 mmol) in DMF (1 mL) was stirred for 10 min, and 3-aminopyridine (17 mg, 0.18 mmol) and triethylamine (46 μL, 0.33 mmol) are added. The solution is heated in a block heater at 45° C. for 20 h. The solution is diluted with EtOAc and is washed with Na₂CO₃, H₂O, and brine. The organic layer is dried (MgSO₄) and evaporated to afford the title compound (102 mg, 0.16 mmol, 99%) as an oil that was used in the next step without purification.

Step 2: Synthesis of 1-Oxo-N-(pyridin-3-yl)-2,3,4,5-tetrahydro-1H-[1,4]diazepino[1,2-a]benzimidazole-8-carboxamide To a solution of tert-butyl {3-[6-(pyridin-3-ylcarbamoyl)-2-(trimethoxymethyl)-1H-benzimidazol-1-yl]propyl}carbamate (85 mg, 0.17 mmol) in methanol (2 mL) was added concentrated HCl (1 mL). The solution is stirred at room temperature for 2 h and is evaporated to dryness. The residue is dissolved in methanol (5 mL), triethylamine (0.14 mL, 1.0 mmol) added, and the solution heated at reflux for 2 h. The cooled solution was diluted with CH₂Cl₂, and washed with Na₂CO₃. The organic layer was dried (MgSO₄) and evaporated. The crude product was purified via preparative HPLC. The major peak was collected by passing the HPLC fractions, without concentrating, directly through an SCX cartridge (Silicycle tosic acid, 1 g). The cartridge was washed with methanol, then CH₂Cl₂/methanol (50:50). Finally, the product was eluted with CH₂Cl₂/methanol containing 1% NH₄OH. The solution containing product was evaporated to afford the title compound (13 mg, 22%).

Example 2 is synthesized according to the procedure for Example 1, substituting commercially available reagents.

Example 3

N-(1-Ethyl-1H-benzimidazol-2-yl)-1-oxo-2,3,4,5-tetrahydro-1H-[1,4]diazepino[1,2-a]benzimidazole-8-carboxamide

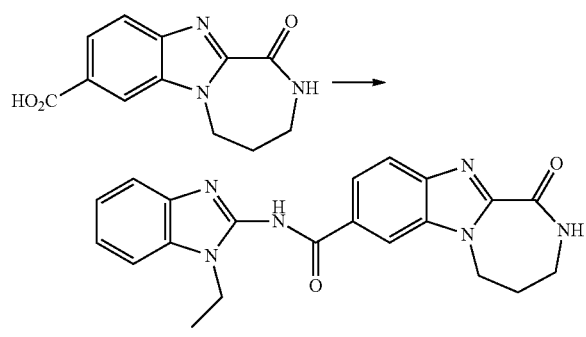

A solution of 1-oxo-2,3,4,5-tetrahydro-1H-[1,4]diazepino[1,2-a]benzimidazole-8-carboxylic acid (Intermediate B, 103 mg, 0.42 mmol) and TBTU (149 mg, 0.46 mmol) in DMF (2 mL) is stirred for 10 min. 1-Ethyl-1H-benzimidazol-2-amine (68 mg, 0.42 mmol) and triethylamine (43 mg, 0.42 mmol) are added and the reaction is stirred at room temperature for 16 h. The reaction mixture is diluted with H₂O. A yellow solid is formed that is filtered and washed with EtOAc and a small amount of methanol to afford the title compound (85 mg, 51%).

Examples 4-17 are synthesized according to the procedure for Example 2, substituting either commercially available reagents or the appropriate intermediates described above.

Example 18

5,5-Dimethyl-1-oxo-N-[1-(propan-2-yl)-1H-benzimidazol-2-yl]-2,3,4,5-tetrahydro-1H-[1,4]diazepino[1,2-a]benzimidazole-8-carboxamide

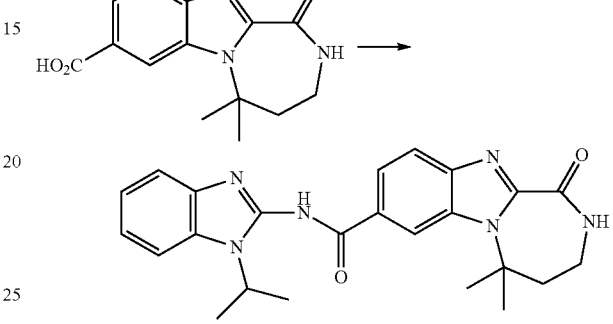

A solution of 5,5-dimethyl-1-oxo-2,3,4,5-tetrahydro-1H-[1,4]diazepino[1,2-a]benzimidazole-8-carboxylic acid (Intermediate C, 45 mg, 0.16 mmol) and PyBOP (145 mg, 0.28 mmol) in DMF (1.5 mL) is stirred for 10 min. 1-(Propan-2-yl)-1H-benzimidazol-2-amine; hydrobromide (Intermediate M, 71 mg, 0.28 mmol) and triethylamine (0.08 mL, 0.56 mmol) are added and the reaction is stirred for 16 h. The mixture is purified via preparative HPLC to afford the title compound (35 mg, 50%).

Example 19

1-Oxo-N-(3-phenyl-1,2-oxazol-5-yl)-2,3,4,5-tetrahydro-1H-[1,4]diazepino[1,2-a]benzimidazole-8-carboxamide

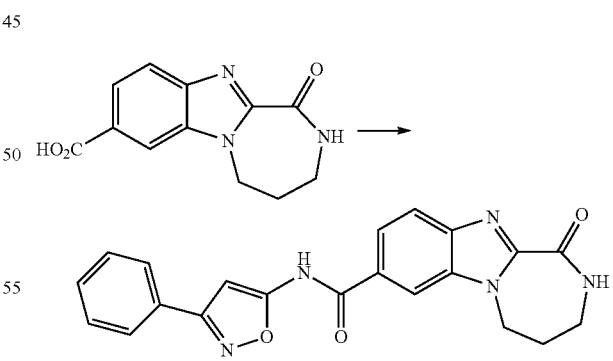

A solution of 1-oxo-2,3,4,5-tetrahydro-1H-[1,4]diazepino[1,2-a]benzimidazole-8-carboxylic acid (Intermediate B, 71 mg, 0.29 mmol) and 1,1'-carbonyldiimidazole (117 mg, 0.72 mmol) in THF (10 mL) is heated to 60° C. for 1 h. The solution is cooled to room temperature and 5-methyl-3-aminoisoxazole (191 mg, 1.16 mmol) is added. After 10 min DBU (0.11 mL, 0.72 mmol) is added and the mixture heated at 60° C. for 16 h. The solvent is evaporated and H₂O is added to the residue. The resulting solid is collected by filtration and is purified via preparative HPLC to afford the title compound (17 mg, 12%).

Example 20

N-(5-Methyl-1,2-oxazol-3-yl)-1-oxo-2,3,4,5-tetrahydro-1H-[1,4]diazepino[1,2-a]benzimidazole-8-carboxamide

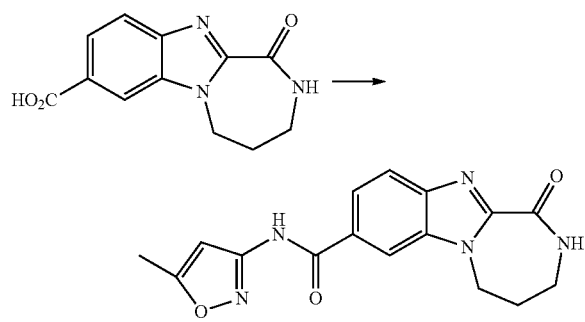

A mixture of 1-oxo-2,3,4,5-tetrahydro-1H-[1,4]diazepino[1,2-a]benzimidazole-8-carboxylic acid (Intermediate B, 51 mg, 0.21 mmol) and HATU (89 mg, 0.23 mmol) in dichloroethane (3 mL) is stirred at room temperature for 1 h. 2-tert-Butylimino-2-diethylamino-1,3-dimethyl-perhydro-1,3,2-diazaphosphorine on polystyrene (64 mg, 0.64 mmol) is added and the mixture is stirred at room temperature for 10 min. 5-Methyl-3-aminoisoxazole (62 mg, 0.64 mmol) is added and the reaction is stirred at 60° C. for 16 h and is cooled to room temperature. The mixture is diluted with methanol, filtered and evaporated. The residue is purified via flash column chromatography using a gradient elution of 0-10% $CH_2Cl_2$/methanol and is triturated with $CH_2Cl_2$ (3 mL), filtered and dried to afford the title compound (25 mg, 36%).

Example 21 is synthesized according to the procedure for Example 20, substituting commercially available reagents.

Example 22

N-[3-(1H-Imidazol-4-yl)phenyl]-1-oxo-2,3,4,5-tetrahydro-1H-[1,4]diazepino[1,2-a]benzimidazole-8-carboxamide

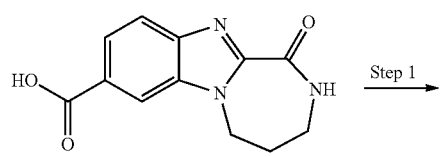 Step 1

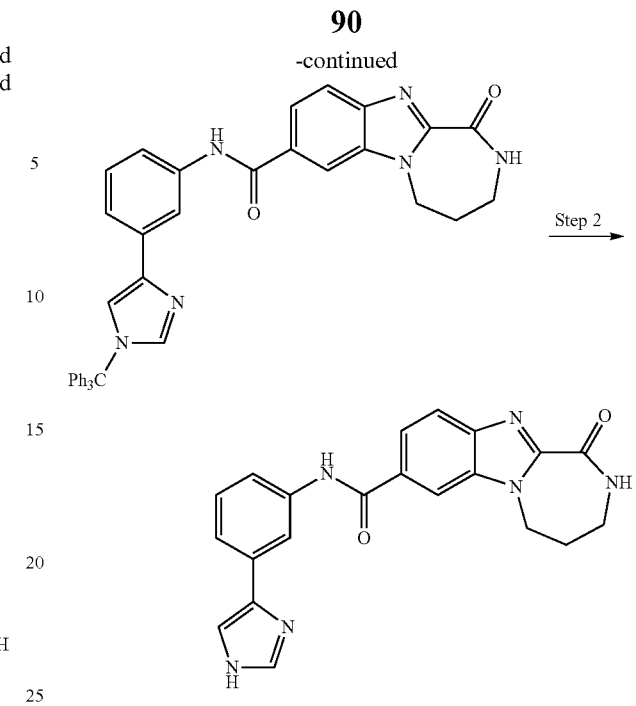

Step 1. Synthesis of 1-oxo-N-[3-(1-trityl-1H-imidazol-4-yl)phenyl]-2,3,4,5-tetrahydro-1H-[1,4]diazepino[1,2-a]benzimidazole-8-carboxamide A solution of 1-oxo-2,3,4,5-tetrahydro-1H-[1,4]diazepino[1,2-a]benzimidazole-8-carboxylic acid (Intermediate B, 59 mg, 0.15 mmol) and TBTU (52 mg, 0.16 mmol) in DMF (2 mL) is stirred for 20 min at room temperature. 3-(1-Tritylimidazol-4-yl)-aniline (Intermediate O, 36 mg, 0.15 mmol) and triethylamine (15 mg, 0.15 mmol) are added and the solution stirred at room temperature for 4 h. DMAP (5 mg, 0.04 mmol) is added and the solution is heated at 60° C. overnight. The reaction is cooled to room temperature and $H_2O$ was added. The resulting precipitate is filtered off and purified via flash column chromatography using a gradient elution of 0-10% $CH_2Cl_2$/methanol, containing 1% $NH_4OH$ to afford the title compound as an oil (67 mg, 73%).

Step 2 Synthesis of N-[3-(1H-imidazol-4-yl)phenyl]-1-oxo-2,3,4,5-tetrahydro-1H-[1,4]diazepino[1,2-a]benzimidazole-8-carboxamide To a solution of 1-oxo-N-[3-(1-trityl-1H-imidazol-4-yl)phenyl]-2,3,4,5-tetrahydro-1H-[1,4]diazepino[1,2-a]benzimidazole-8-carboxamide (53 mg, 0.08 mmol) in $CH_2Cl_2$ (3 mL) is added TFA (0.5 mL) and the solution is stirred for 2 h at room temperature. The solvent is evaporated and the residue treated with 0.1M aqueous NaOH solution. A brown solid

Example 23

6-oxo-N-(quinolin-3-yl)-7,8,9,10-tetrahydro-6H-pyrido[3',2':4,5]pyrrolo[1,2-a][1,4]diazepine-2-carboxamide

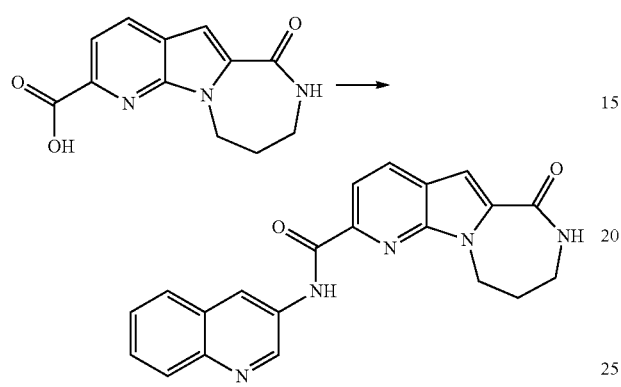

A solution of 6-oxo-7,8,9,10-tetrahydro-6H-pyrido[3',2': 4,5]pyrrolo[1,2-a][1,4]diazepine-2-carboxylic acid (Intermediate E, 75 mg, 0.31 mmol) and PyBOP (175 mg, 0.34 mmol) in DMF (2 mL) is stirred for 30 min. 3-Aminoquinoline (49 mg, 0.34 mmol) and triethylamine (171 µL, 1.22 mmol) are added and the reaction is stirred at room temperature for 16 h. The mixture is purified via preparative HPLC using a gradient elution from 10-75% acetonitrile/H₂O with 0.1% TFA to afford the title compound (93 mg, 82%). LCMS: 372.20 (M+H⁺). (Method V)

Examples 24-78 are synthesized according to the procedure for Example 23, substituting either commercially available reagents or the appropriate intermediates described above.

Example 79

N-(5-tert-Butyl-1,2-oxazol-3-yl)-6-oxo-7,8,9,10-tetrahydro-6H-pyrido[3',2':4,5]pyrrolo[1,2-a][1,4]diazepine-2-carboxamide

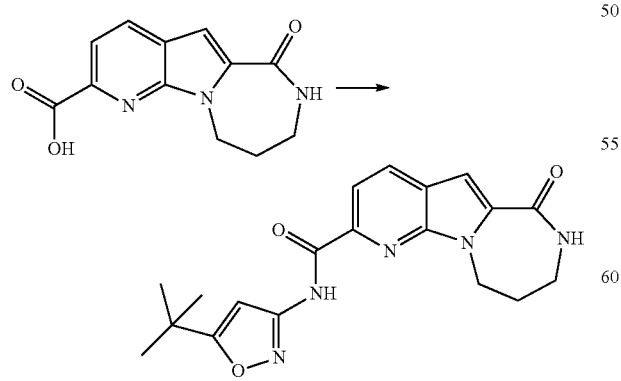

To a solution of 6-oxo-7,8,9,10-tetrahydro-6H-pyrido[3', 2':4,5]pyrrolo[1,2-a][1,4]diazepine-2-carboxylic acid (Intermediate E, 35 mg, 0.14 mmol) in THF (2 mL) and NMP (0.5 mL) is added 1,1'-carbonyldiimidazole (58 mg, 0.36 mmol). The mixture is stirred at 60° C. for 1 h and is then cooled to room temperature. 5-tert-Butyl-3-aminoisoxazole (80 mg, 0.57 mmol) and DBU (53 µL, 0.36 mmol) are added and the mixture is stirred at 60° C. for 16 h. The mixture is cooled to room temperature and the THF is removed in vacuo. The residue is purified via preparative HPLC using a gradient elution from 10-75% acetonitrile/H₂O with 0.1% TFA to afford the title compound (6 mg, 11%). LCMS: 368.20 (M+H+). (System V-med polar)

Example 80

N-(5-Methyl-1,2-oxazol-3-yl)-6-oxo-7,8,9,10-tetrahydro-6H-pyrido[3',2':4,5]pyrrolo[1,2-a][1,4]diazepine-2-carboxamide

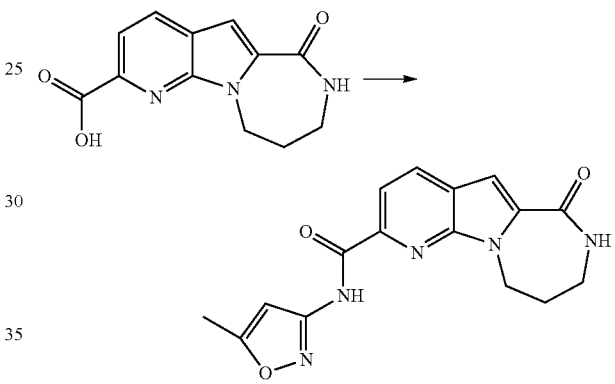

To a solution of 6-oxo-7,8,9,10-tetrahydro-6H-pyrido[3', 2':4,5]pyrrolo[1,2-a][1,4]diazepine-2-carboxylic acid (Intermediate E, 100 mg, 0.41 mmol) in THF (2 mL) and DMF (0.5 mL) is added HATU (171 mg, 0.45 mmol). The mixture is stirred at room temperature for 1 h, after which 2-tert-butylimino-2-diethylamino-1,3-dimethyl-perhydro-1,3,2-diazaphosphorine on polystyrene (556 mg, 1.22 mmol) is added. The mixture is stirred at room temperature for 10 min and 5-methyl-3-aminoisoxazole (120 mg, 1.22 mmol) is added. The reaction is stirred at 60° C. for 16 h and is then cooled to room temperature. The mixture is filtered, washing with methanol and the filtrate is concentrated under reduced pressure. The residue is purified via preparative HPLC using a gradient elution from 10-90% acetonitrile/H₂O with 0.1% TFA to afford the title compound (11 mg, 8%). LCMS: 326.20 (M+H⁺). (System V-med polar)

Examples 81-86 are synthesized according to the procedure for Example 80, substituting either commercially available reagents or the appropriate intermediates described above.

Example 87

6-Oxo-N-(quinolin-3-yl)-7,8,9,10-tetrahydro-6H-pyrido[3',2':4,5]pyrrolo[1,2-a][1,4]diazepine-2-carboxamide

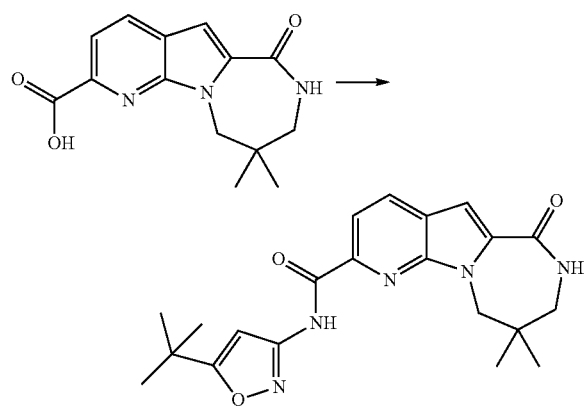

To a suspension of 9,9-dimethyl-6-oxo-7,8,9,10-tetrahydro-6H-pyrido[3',2':4,5]pyrrolo[1,2-a][1,4]diazepine-2-carboxylic acid (Intermediate F, 50 mg, 0.18 mmol) in toluene (1 mL) is added thionyl chloride (27 µL, 0.37 mmol) and the mixture is heated at reflux. After 2 h, the mixture is cooled to room temperature and is concentrated under reduced pressure. Toluene (1 mL) is added to the residue and it is concentrated once again under reduced pressure. Toluene (2 mL) is added once more and the volume is reduced by half. 5-tert-butyl-3-aminoisoxazole (51 mg, 0.37 mmol) and N,N-diisopropylethylamine (64 µL, 0.37 mmol) are added and the reaction is stirred at room temperature for 16 h. The reaction mixture is evaporated and the residue is purified via preparative HPLC using a gradient elution from 10-75% acetonitrile/H$_2$O with 0.1% TFA to afford the title compound (8 mg, 11%). LCMS: 396.83 (M+H$^+$).

Examples 88-93 are synthesized according to the procedure for Example 90, substituting either commercially available reagents or the appropriate intermediates described above.

Example 94

N-(5-benzyl-1,2-oxazol-3-yl)-10-methyl-6-oxo-7,8,9,10-tetrahydro-6H-pyrido[3',2':4,5]pyrrolo[1,2-a][1,4]diazepine-2-carboxamide

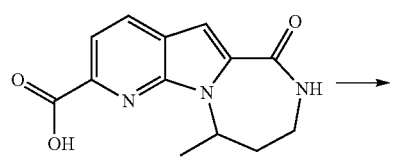

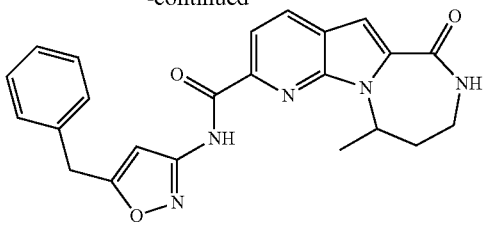

To a suspension of 10-methyl-6-oxo-7,8,9,10-tetrahydro-6H-pyrido[3',2':4,5]pyrrolo[1,2-a][1,4]diazepine-2-carboxylic acid (Intermediate G, 75 mg, 0.29 mmol) in CH$_2$Cl$_2$ (5 mL) is added 1-chloro-N,N,2-trimethylpropenylamine (138 µL, 1.01 mmol) and the mixture is stirred at room temperature for 30 min. 5-benzyl-1,2-oxazol-3-amine (Intermediate W, 252 mg, 1.45 mmol) and pyridine (94 µL, 1.16 mmol) are added and the reaction is stirred at room temperature for 20 h. The mixture is concentrated under reduced pressure and the residue is purified via preparative HPLC using a gradient elution from 10-90% acetonitrile/H$_2$O with 0.1% TFA to afford the title compound (19 mg, 16%). LCMS: 416.20 (M+H+). (System V-med polar)

Examples 95-100 are synthesized according to the procedure for Example 97, substituting either commercially available reagents or the appropriate intermediates described above.

Example 101

9-methyl-6-oxo-N-(pyridin-3-yl)-6,7,8,9-tetrahydropyrido[3',2':4,5]pyrrolo[1,2-a]pyrazine-2-carboxamide

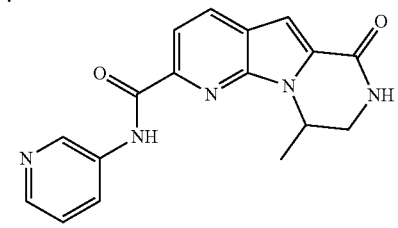

To a suspension of 9-methyl-6-oxo-6,7,8,9-tetrahydropyrido[3',2':4,5]pyrrolo[1,2-a]pyrazine-2-carboxylic acid (Intermediate J, 47 mg, 0.19 mmol) and HOBt (31 mg, 0.23 mmol) in DMF (0.5 mL) is added 1-ethyl-3-(3-dimethylaminopropyl)carbodiimide hydrochloride (44 mg, 0.23 mmol), followed by 3-aminopyridine (22 mg, 0.23 mmol) and DMAP (2.8 mg, 0.023 mmol). The mixture is stirred at 60° C. under a continuous stream of nitrogen, which slowly concentrates the solution. After being stirred for 5 h, the mixture was warmed to 80° C. and stirred overnight. The reaction mixture is diluted with methanol (0.5 mL) and ether (1 mL). The resultant precipitate is collected by filtration to afford the title compound as a dark yellow solid (21 mg, 34%).

Examples 102 and 103 are synthesized according to the procedure for Example 102, substituting either commercially available reagents or the appropriate intermediates described above.

Example 104

N-[2-(cyclopentylcarbamoyl)-1-methyl-1H-imidazol-4-yl]-6-oxo-7,8,9,10-tetrahydro-6H-pyrido[3',2':4,5]pyrrolo[1,2-a][1,4]diazepine-2-carboxamide

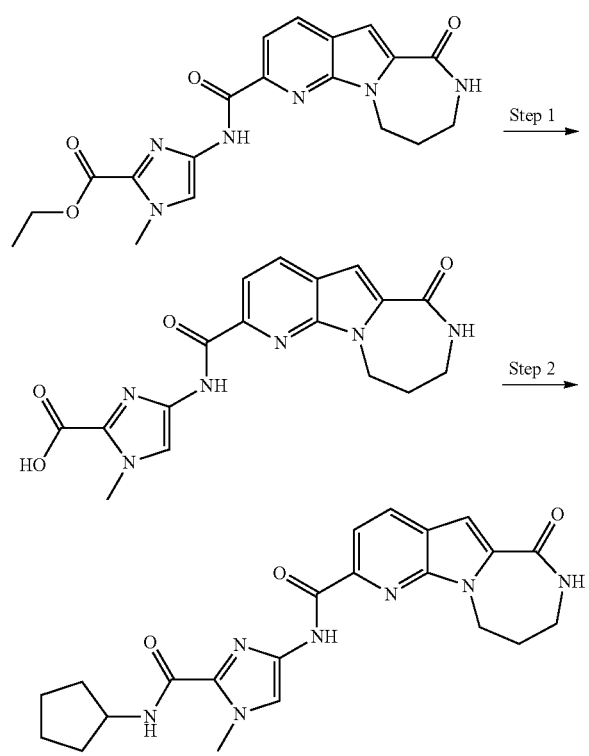

Step 1: Synthesis of 1-methyl-4-{[(6-oxo-7,8,9,10-tetrahydro-6H-pyrido[3',2':4,5]pyrrolo[1,2-a][1,4]diazepin-2-yl)carbonyl]amino}-1H-imidazole-2-carboxylic acid To a suspension of ethyl 1-methyl-4-{[(6-oxo-7,8,9,10-tetrahydro-6H-pyrido[3',2':4,5]pyrrolo[1,2-a][1,4]diazepin-2-yl)carbonyl]amino}-1H-imidazole-2-carboxylate (Example 28, 160 mg, 0.40 mmol) in methanol (3 mL) is added 2M aqueous NaOH (0.4 mL). The mixture is stirred at 60° C. for 3 h and is then cooled to room temperature. The methanol is removed in vacuo and the aqueous mixture is acidified to pH 5 with 1N aqueous HCl. The resulting solid is collected by filtration and dried in vacuo to afford the title compound as a yellow solid (130 mg, 87%). LCMS: 369.20 (M+H+). (System V)

Step 2: Synthesis of N-[2-(cyclopentylcarbamoyl)-1-methyl-1H-imidazol-4-yl]-6-oxo-7,8,9,10-tetrahydro-6H-pyrido[3',2':4,5]pyrrolo[1,2-a][1,4]diazepine-2-carboxamide To a solution of 1-methyl-4-{[(6-oxo-7,8,9,10-tetrahydro-6H-pyrido[3',2':4,5]pyrrolo[1,2-a][1,4]diazepin-2-yl)carbonyl]amino}-1H-imidazole-2-carboxylic acid (50 mg, 0.14 mmol) in DMF (1.5 mL) was added cyclopentylamine (27 µL, 0.27 mmol), HOBt (18 mg, 0.14 mmol), N,N-diisopropylethylamine (47 µL, 0.27 mmol), and DMAP (3 mg, 0.027 mmol) followed by 1-ethyl-3-(3-dimethylaminopropyl)carbodiimide hydrochloride (78 mg, 0.41 mmol). The mixture is stirred at room temperature for 64 h. The mixture is poured over H₂O and the resulting solid is collected by filtration and is purified via preparative HPLC using a gradient elution from 10-75% acetonitrile/H₂O with 0.1% TFA to obtain the title compound (6 mg, 10%). LCMS: 436.20 (M+H+). (System V-med polar)

Example 105

N-[3-(1H-imidazol-4-yl)phenyl]-6-oxo-7,8,9,10-tetrahydro-6H-pyrido[3',2':4,5]pyrrolo[1,2-a][1,4]diazepine-2-carboxamide

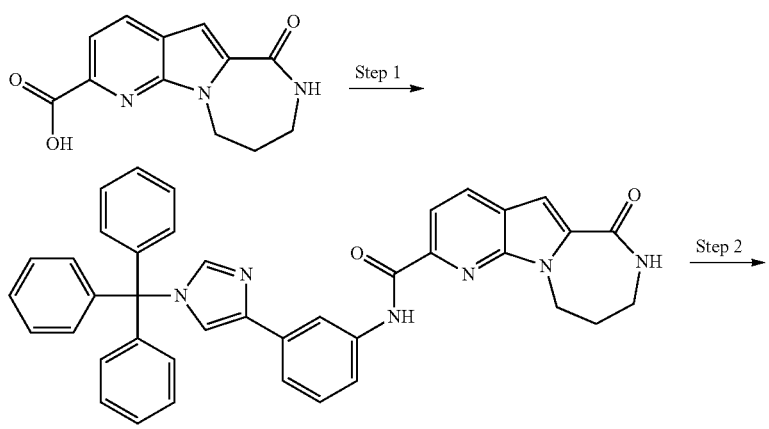

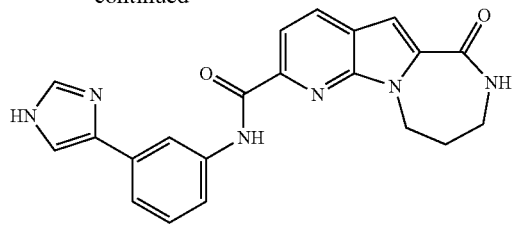

Step 1: Synthesis of 6-oxo-N-[3-(1-trityl-1H-imidazol-4-yl)phenyl]-7,8,9,10-tetrahydro-6H-pyrido[3',2':4,5]pyrrolo[1,2-a][1,4]diazepine-2-carboxamide A solution of 6-Oxo-7,8,9,10-tetrahydro-6H-pyrido[3',2':4,5]pyrrolo[1,2-a][1,4]diazepine-2-carboxylic acid (Intermediate E, 50 mg, 0.20 mmol) and PyBOP (159 mg, 0.31 mmol) in DMF (1.5 mL) is stirred for 30 min. 3-(1-Trityl-1H-imidazol-4-yl)-phenylamine (86 mg, 0.21 mmol) and triethylamine (57 µL, 0.41 mmol) are added and the reaction is stirred at room temperature for 16 h. The mixture is poured into H₂O and the resulting white solid is collected by filtration and dried in vacuo to afford the title compound (86 mg, 67%) which was used in the next step without further purification.

Step 2: Synthesis of N-[3-(1H-imidazol-4-yl)phenyl]-6-oxo-7,8,9,10-tetrahydro-6H-pyrido[3',2':4,5]pyrrolo[1,2-a][1,4]diazepine-2-carboxamide To a solution of 6-oxo-N-[3-(1-trityl-1H-imidazol-4-yl)phenyl]-7,8,9,10-tetrahydro-6H-pyrido[3',2':4,5]pyrrolo[1,2-a][1,4]diazepine-2-carboxamide (86 mg, 0.14 mmol) in CH₂Cl₂ (1 mL) is added TFA (0.5 mL). The mixture is stirred at room temperature for 16 hr then is concentrated under reduced pressure. The residue is purified via preparative HPLC using a gradient elution from 10-75% acetonitrile/H₂O with 0.1% TFA to afford the title compound (25 mg, 47%). LCMS: 387.86 (M+H⁺). (System T-med polar) Table 3 below, lists the mass spectral data and the HPLC retention times for Examples 1 to 105.

TABLE 3

| Example | m/z [M + H] | HPLC retention time (min) | Method |
| --- | --- | --- | --- |
| 1 | 322.64 | 0.8 | T |
| 2 | 375.66 | 1.17 | T |
| 3 | 389.46 | 4.87 | B |
| 4 | 403.52 | 5.2 | B |
| 5 | 336.4 | 1.12 | B |
| 6 | 401.59 | 4.53 | B |
| 7 | 418.42 | 5.07 | B |
| 8 | 339.44 | 4.98 | B |
| 9 | 364.45 | 4.49 | B |
| 10 | 436.9 | 1.22 | T |
| 11 | 404.5 | 4.79 | B |
| 12 | 372.42 | 4.63 | B |
| 13 | 325.44 | 4.31 | B |
| 14 | 353.67 | 0.96 | T |
| 15 | 424.45 | 5.09 | B |
| 16 | 446.48 | 4.26 | B |
| 17 | 390.57 | 4.66 | B |
| 18 | 431.70 | 1.38 | T |
| 19 | 388.56 | 5.27 | B |
| 20 | 326.41 | 4.44 | B |
| 21 | 368.47 | 5.03 | B |
| 22 | 387.39 | 3.91 | B |

TABLE 3-continued

| Example | m/z [M + H] | HPLC retention time (min) | Method |
| --- | --- | --- | --- |
| 23 | 372.20 | 1.09 | V |
| 24 | 418.20 | 1.25 | V |
| 25 | 339.20 | 1.20 | V |
| 26 | 364.20 | 1.03 | V |
| 27 | 320.20 | 0.97 | V |
| 28 | 397.20 | 1.08 | V |
| 29 | 418.20 | 1.21 | V |
| 30 | 404.20 | 1.16 | V |
| 31 | 432.86 | 1.56 | T |
| 32 | 460.20 | 1.13 | V |
| 33 | 446.83 | 1.30 | T |
| 34 | 474.85 | 1.46 | T |
| 35 | 460.20 | 1.11 | V |
| 36 | 446.82 | 1.29 | T |
| 37 | 474.85 | 1.42 | T |
| 38 | 336.20 | 1.05 | V |
| 39 | 400.81 | 1.51 | T |
| 40 | 339.78 | 1.17 | T |
| 41 | 325.20 | 0.91 | V |
| 42 | 353.78 | 1.27 | T |
| 43 | 381.20 | 1.15 | V |
| 44 | 367.84 | 1.34 | T |
| 45 | 395.84 | 1.49 | T |
| 46 | 415.20 | 1.17 | V |
| 47 | 401.81 | 1.39 | T |
| 48 | 429.85 | 1.53 | T |
| 49 | 494.86 | 1.17 | T |
| 50 | 423.76 | 1.61 | T |
| 51 | 375.20 | 0.93 | V |
| 52 | 403.82 | 1.21 | T |
| 53 | 403.20 | 1.06 | V |
| 54 | 431.83 | 1.37 | T |
| 55 | 389.20 | 1.00 | V |
| 56 | 417.82 | 1.27 | T |
| 57 | 446.20 | 0.79 | V |
| 58 | 474.85 | 1.09 | T |
| 59 | 401.86 | 1.41 | T |
| 60 | 401.84 | 1.41 | T |
| 61 | 415.86 | 1.47 | T |
| 62 | 415.86 | 1.45 | T |
| 63 | 404.34 | 0.86 | H |
| 64 | 372.28 | 0.81 | H |
| 65 | 372.28 | 0.81 | H |
| 66 | 404.33 | 0.86 | H |
| 67 | 395.20 | 1.17 | V |
| 68 | 416.20 | 0.86 | V |
| 69 | 403.85 | 1.28 | T |
| 70 | 460.92 | 1.10 | T |
| 71 | 389.82 | 1.28 | T |
| 72 | 389.82 | 1.28 | T |
| 73 | 403.83 | 1.34 | T |
| 74 | 403.87 | 1.31 | T |
| 75 | 446.91 | 1.08 | T |
| 76 | 446.93 | 1.10 | T |
| 77 | 460.92 | 1.13 | T |
| 78 | 460.92 | 1.12 | T |
| 79 | 368.20 | 1.29 | V |
| 80 | 326.20 | 1.06 | V |
| 81 | 388.20 | 1.27 | V |
| 82 | 340.76 | 1.39 | T |
| 83 | 326.77 | 1.38 | T |

TABLE 3-continued

| Example | m/z [M + H] | HPLC retention time (min) | Method |
|---|---|---|---|
| 84 | 326.77 | 1.38 | T |
| 85 | 340.77 | 1.41 | T |
| 86 | 340.78 | 1.40 | T |
| 87 | 396.83 | 1.76 | T |
| 88 | 368.63 | 1.60 | T |
| 89 | 382.82 | 1.70 | T |
| 90 | 380.80 | 1.60 | T |
| 91 | 354.76 | 1.48 | T |
| 92 | 416.82 | 1.80 | T |
| 93 | 430.83 | 1.76 | T |
| 94 | 416.20 | 1.36 | T |
| 95 | 402.83 | 1.58 | T |
| 96 | 401.86 | 1.54 | T |
| 97 | 402.83 | 1.59 | T |
| 98 | 402.84 | 1.58 | T |
| 99 | 416.84 | 1.62 | T |
| 100 | 416.85 | 1.62 | T |
| 101 | 322.64 | 1.10 | T |
| 102 | 385.65 | 1.27 | T |
| 103 | 328.61 | 1.37 | T |
| 104 | 436.20 | 1.21 | V |
| 105 | 387.86 | 1.06 | T |

Assessment of Biological Properties

The biological properties of the compounds of the invention are assessed using the assays described below.

Experimental Method A: Human RSK2 Assay

Compounds are assessed for their ability to inhibit the phosphorylation of a substrate peptide by RSK2.

Human RSK2 protein, purchased from Invitrogen, is used to measure kinase activity utilizing Kinase Glo Plus (Promega) a homogeneous assay technology, which uses a luciferin-luciferase based ATP detection reagent to quantify residual ATP. The assay is performed using 0.75 nM His-RSK2, 0.75 µM ATP and 1.0 µM S6 Kinase/RSK Substrate Peptide 1 (Upstate, catalog #12-124), in assay buffer consisting of 25 mM HEPES, pH 7.5, 10 mM $MgCl_2$, 5 mM $MnCl_2$, 50 mM KCl, 0.2% BSA, 0.01% CHAPS, 100 µM $Na_3VO_4$, 0.5 mM DTT, and 1% DMSO. Solutions of test compounds at various concentrations are prepared by 1:3 fold serial dilution of a 1 mM solution of compound in DMSO. The DMSO solutions are further diluted with assay buffer to a final concentration of DMSO of 5%.

The assay is performed in a 384 well, white, non-binding plate (Corning, catalogue #3574). Solutions of test compounds (10 µL) are transferred to a dry assay plate, followed by addition of 20 µL kinase and 20 µL ATP+Substrate Peptide 1 described above. The kinase reaction mixture is incubated for 90 minutes at 28° C. followed by addition of 30 µL of ATP detection reagent for 15 minutes at room temperature. The relative light unit (RLU) signal is measured on a LJL Analyst (Molecular Devices) in luminescence mode using 384 aperture. The RLU signals were converted to percent of control (POC) values using the formula:

POC=100*(BCTRL−Signal)/(BCTRL−PCTRL), where Signal is the test well RLU signal, BCTRL is the average of background (negative control), which consists of ATP+peptide and compound buffer, well signals on the plate, and PCTRL is the average of positive control, which consists of kinase, ATP+peptide, and compound buffer, well signals on the plate. For concentration-responsive compounds, POC as a function of test compound concentration are fitted to a 4-parameter logistic equation of the form:

$$Y=A+(B-A)/[1+(x/C)^D],$$

where A, B, C, and D are fitted parameters (parameter B is fixed at zero POC), and x and y are the independent and dependent variables, respectively. The $IC_{50}$ (50% inhibitory concentration) is determined as the inflection point parameter, C.

Experimental Method B: Human RSK2 Trans-Reporter Assay

Compounds are assessed for their ability to inhibit the phosphorylation of the transcription factor CREB (cAMP Response Element Binding) by RSK2 in cells.

A cell monolayer of exponentially growing HLR-CREB cells (PathDetect® HeLa Luciferase Reporter CREB cells, Stratagene) is prepared by the following method. In a 100 mm culture dish, $7.5 \times 10^5$ HLR-CREB cells are added to 10 mL culture medium consisting of RPMI-1640, 10% heat inactivated FCS, 2 mM glutamine, and 50 µg/mL gentamycin. The cells are allowed to adhere overnight, at which point 6 mL of medium is removed.

The cell monolayer is transfected using Effectene (Quiagen) with RSK2 by the following method. A mixture of DNA, pCMV6-XL-RSK2 (1.0 µg) and pcDNA 3.1 (1.0 µg), is added to 300 µL DNA-condensation buffer. The complexes are formed by addition of 16 µL enhancer, and the mixture is incubated for 5 minutes at room temperature. Then, 60 µL Effectene is added, and the mixture is incubated for an additional 10 minutes at room temperature. The final volume is adjusted to 2.0 mL with complete media, and added to the cell monolayer.

Five hours after transfection, the cells are plated into white 96 well culture plates (Greiner Bio-One 655083). Compounds are added at various concentrations to the cells 20-24 hours after transfection, and are stimulated with 20 nM Phorbol 12-myristate 13-acetate (PMA). Determination of the luciferase expression was 48 hours after transfection. The luciferase activity was determined using the protocol provided by Steady-Glo (Promega).

The results are represented as the percent luciferase activity relative to the control measured in the absence of inhibitors (POC). The data representing POC as a function of test compound concentration were fitted to a 4-parameter logistic equation of the form: Y=A+(B−A)/[1+(x/C) D], where A, B, C, and D are fitted parameters, and x and y are the independent and dependent variables, respectively. The $IC_{50}$ (50% inhibitory concentration) was determined as the inflection point parameter, C. Each data point represents an average of triplicate observations.

Concurrently, compound cytotoxicity was assessed by reduction of AlamarBlue (Invitrogen). Five hours after transfection, the cells are plated into clear 96 well culture plates (Costar 3595) and cultured with compounds as described above for luciferase expression. AlamarBlue was added to each well 48 hours after transfection and returned to incubator for an additional 3-4 hours at 37° C. Fluorescent units were determined using 540 nm for excitation and 590 nm for emission.

The AlamarBlue results are represented as the percent fluorescent units relative to the control measured in the absence of inhibitors (POC). The data representing POC as a function of test compound concentration were fitted to a 4-parameter logistic equation of the form: Y=A+(B−A)/[1+(x/C) D], where A, B, C, and D are fitted parameters, and x and y are the independent and dependent variables, respectively. Each data point represents an average of triplicate observations.

The RSK2 ($IC_{50}$) activity of Examples 1 to 105 are shown in Table 4 below.

TABLE 4

| Example | RSK2 IC$_{50}$ (nM) |
|---|---|
| 1 | 5600 |
| 2 | 35 |
| 3 | 5.5 |
| 4 | 33 |
| 5 | 3200 |
| 6 | 44 |
| 7 | 1700 |
| 8 | 960 |
| 9 | 295 |
| 10 | 69 |
| 11 | 870 |
| 12 | 1200 |
| 13 | 320 |
| 14 | 4000 |
| 15 | 45 |
| 16 | 92 |
| 17 | 23 |
| 18 | 4.7 |
| 19 | 290 |
| 20 | 1550 |
| 21 | 2000 |
| 22 | 1700 |
| 23 | 9.2 |
| 24 | 56 |
| 25 | 20 |
| 26 | 2.3 |
| 27 | 37 |
| 28 | 90 |
| 29 | 2.1 |
| 30 | 25 |
| 31 | 105 |
| 32 | 2.3 |
| 33 | 20 |
| 34 | 62 |
| 35 | 1.6 |
| 36 | 13 |
| 37 | 25 |
| 38 | 3.8 |
| 39 | 91 |
| 40 | 0.78 |
| 41 | 4.8 |
| 42 | 72 |
| 43 | 1.1 |
| 44 | 9.7 |
| 45 | 50 |
| 46 | 0.39 |
| 47 | 3.8 |
| 48 | 12 |
| 49 | 6.7 |
| 50 | 55 |
| 51 | 365 |
| 52 | 2500 |
| 53 | 630 |
| 54 | 1300 |
| 55 | 140 |
| 56 | 195 |
| 57 | 245 |
| 58 | 2300 |
| 59 | 0.2 |
| 60 | 12 |
| 61 | 0.34 |
| 62 | 3 |
| 63 | 84 |
| 64 | 3 |
| 65 | 34 |
| 66 | 4 |
| 67 | 6.1 |
| 68 | 0.27 |
| 69 | 15 |
| 70 | 27 |
| 71 | 54.5 |
| 72 | 26.5 |
| 73 | 11.6 |
| 74 | 1111 |
| 75 | 265 |
| 76 | 54 |
| 77 | 29 |
| 78 | 205 |
| 79 | 19 |
| 80 | 19 |
| 81 | 4.3 |
| 82 | 5.2 |
| 83 | 380 |
| 84 | 6.6 |
| 85 | 2.6 |
| 86 | 110 |
| 87 | 175 |
| 88 | 109 |
| 89 | 125 |
| 90 | 43 |
| 91 | 395 |
| 92 | 502 |
| 93 | 360 |
| 94 | 3.3 |
| 95 | 3.6 |
| 96 | 13 |
| 97 | 490 |
| 98 | 3.9 |
| 99 | 5.1 |
| 100 | 57 |
| 101 | 120 |
| 102 | 130 |
| 103 | 330 |
| 104 | 1.6 |
| 105 | 17 |

Method of Use

The compounds of the invention are effective inhibitors of RSK2. Therefore, in one embodiment of the invention, there is provided methods of treating RSK2 regulated disorders using compounds of the invention. In another embodiment, there is provided methods of treating cardiovascular, inflammatory, allergic, pulmonary and fibrotic diseases, renal diseases and cancer using compounds of the invention.

The inhibition or modulation of RSK2 activity is an attractive means for preventing and treating a variety of diseases mediated by RSKs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection; and Cancer including solid tumors, leukemias and lymphomas.
Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I):

(I)

wherein:

X is N or C;

Y is C or N;

wherein when X=N then Y=C and when X=C then Y=N;

$R^1$ is aryl or heteroaryl selected from the group consisting of phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl, indolyl, and quinolinyl; wherein each of the foregoing $R^1$ groups is optionally substituted with 1 to 3 substituents selected from $R^6$;

$R^2$ and $R^3$ are each independently H or $C_1$-$C_5$ alkyl; or $R^2$ and $R^3$ together with the carbon atom to which they are attached, form a $C_3$-$C_8$ cycloalkyl ring;

$R^4$ and $R^5$ are each independently H or $C_1$-$C_5$ alkyl; or $R^4$ and $R^5$ together with the carbon atom to which they are attached, form a $C_3$-$C_8$ cycloalkyl ring;

each $R^6$ is independently $C_1$-$C_5$ alkyl, —$C_1$-$C_5$ alkylamino, —$C_1$-$C_5$ alkyl-NH—$C_1$-$C_3$ alkyl, —$C_1$-$C_5$ alkyl-N($C_1$-$C_3$ alkyl)$_2$, —$C_1$-$C_5$ alkyl-aryl, —$C_1$-$C_5$ alkyl-heteroaryl, —$C_1$-$C_5$ alkyl-heterocyclyl, $C_1$-$C_5$ alkoxyl, $C_3$-$C_8$ cycloalkyl, —C(O)NH$_2$, —C(O)NH—$C_1$-$C_5$ alkyl, —C(O)N($C_1$-$C_5$ alky)$_2$, —C(O)NH—$C_3$-$C_8$ cycloalkyl, —C(O)O$C_1$-$C_5$ alkyl, halogen, cyano, heterocyclyl, aryl or heteroaryl; wherein each aryl and heteroaryl of said $R^6$ is optionally independently substituted with 1 to 2 of $C_1$-$C_5$ alkyl;

n is 0 or 1;

or a pharmaceutically acceptable salt thereof.

2. The compound of claim 1, wherein:

X is C;

Y is N;

$R^1$ is aryl or heteroaryl; wherein each of the foregoing $R^1$ groups is optionally substituted with 1 to 3 substituents selected from $R^6$;

$R^2$ and $R^3$ are each independently H or $C_1$-$C_5$ alkyl; or $R^2$ and $R^3$ together with the carbon atom to which they are attached, form a $C_3$-$C_8$ cycloalkyl ring;

$R^4$ and $R^5$ are each independently H or $C_1$-$C_5$ alkyl; or $R^4$ and $R^5$ together with the carbon atom to which they are attached, form a $C_3$-$C_8$ cycloalkyl ring; and each $R^6$ is independently $C_1$-$C_5$ alkyl, —$C_1$-$C_5$ alkylamino, —$C_1$-$C_5$ alkyl-NH—$C_1$-$C_3$ alkyl, —$C_1$-$C_5$ alkyl-N($C_1$-$C_3$ alkyl)$_2$, —$C_1$-$C_5$ alkyl-aryl, —$C_1$-$C_5$ alkyl-heteroaryl, —$C_1$-$C_5$ alkyl-heterocyclyl, $C_1$-$C_5$ alkoxyl, $C_3$-$C_8$ cycloalkyl, —C(O)NH$_2$, —C(O)NH—$C_1$-$C_5$ alkyl, —C(O)N($C_1$-$C_5$ alky)$_2$, —C(O)NH—$C_3$-$C_8$ cycloalkyl, —C(O)O$C_1$-$C_5$ alkyl, halogen, cyano, heterocyclyl, aryl or heteroaryl; wherein each aryl and heteroaryl of said $R^6$ is optionally independently substituted with 1 to 2 of $C_1$-$C_5$ alkyl; and n is 0 or 1;

or a pharmaceutically acceptable salt thereof.

3. The compound of claim 1 wherein:

R¹ is phenyl, isoxazolyl, oxazolyl, imidazolyl, pyrazolyl, thiazolyl, furanyl, thienyl, pyrrolyl, pyridinyl, pyrimidinyl, pyridazinyl, benzimidazolyl, benzopyrazolyl, pyrazolopyridinyl, imidazopyridinyl, indolyl, or quinolinyl; wherein each of the foregoing R¹ groups is optionally substituted with 1 to 3 substituents selected from R⁶;

R² and R³ are each independently H or $C_1$-$C_3$ alkyl; or

R² and R³ together with the carbon atom to which they are attached, form a $C_3$-$C_6$ cycloalkyl ring;

R⁴ and R⁵ are each independently H or $C_1$-$C_3$ alkyl; or

R⁴ and R⁵ together with the carbon atom to which they are attached, form a $C_3$-$C_6$ cycloalkyl ring; and each R⁶ is independently $C_1$-$C_5$ alkyl, —$C_1$-$C_5$ alkylamino, —$C_1$-$C_5$ alkyl-NH—$C_1$-$C_3$ alkyl, —$C_1$-$C_5$ alkyl-N($C_1$-$C_3$ alkyl)₂, —$C_1$-$C_5$ alkyl-phenyl, $C_1$-$C_3$ alkoxyl, $C_3$-$C_6$ cycloalkyl, —C(O)NH₂, —C(O)NH—$C_1$-$C_3$ alkyl, —C(O)N($C_1$-$C_3$ alkyl)₂, —C(O)NH—$C_3$-$C_6$ cycloalkyl, halogen, cyano or heteroaryl; wherein each heteroaryl of said R⁶ is optionally independently substituted with 1 to 2 of $C_1$-$C_3$ alkyl;

or a pharmaceutically acceptable salt thereof.

4. The compound of claim 3, wherein:

R¹ is phenyl, isoxazolyl, imidazolyl, pyrazolyl, pyridinyl, benzimidazolyl, pyrazolopyridinyl, imidazopyridinyl or quinolinyl; wherein each of the foregoing R¹ groups is optionally substituted with 1 to 3 substituents selected from R⁶;

R² and R³ are each independently H or $C_1$-$C_3$ alkyl;

R⁴ and R⁵ are each independently H or $C_1$-$C_3$ alkyl;

each R⁶ is independently $C_1$-$C_5$ alkyl, —$C_1$-$C_5$ alkyl-N($C_1$-$C_2$ alkyl)₂, —CH₂-phenyl, —C(O)NH₂, —C(O)NH—$C_3$-$C_6$ cycloalkyl, halogen or heteroaryl; wherein each heteroaryl of said R⁶ is optionally independently substituted with 1 to 2 of $C_1$-$C_3$ alkyl; and n is 1;

or a pharmaceutically acceptable salt thereof.

5. The compound of claim 4 wherein:

R¹ is benzimidazolyl substituted with 1 to 2 substituents selected from R⁶;

R² and R³ are each independently H or methyl;

R⁴ and R⁵ are H; and

R⁶ is $C_1$-$C_3$ alkyl;

or a pharmaceutically acceptable salt thereof.

6. The compound of claim 1 wherein:

X is N;

Y is C;

R¹ is aryl or heteroaryl, each optionally substituted with 1 to 3 substituents selected from R⁶;

R² and R³ are each independently H or $C_1$-$C_5$ alkyl; or

R² and R³ together with the carbon atom to which they are attached, form a $C_3$-$C_8$ cycloalkyl ring;

R⁴ and R⁵ are each independently H or $C_1$-$C_5$ alkyl; or

R⁴ and R⁵ together with the carbon atom to which they are attached, form a $C_3$-$C_8$ cycloalkyl ring;

each R⁶ is independently $C_1$-$C_5$ alkyl, —$C_1$-$C_5$ alkylamino, —$C_1$-$C_5$ alkyl-NH—$C_1$-$C_3$ alkyl, —$C_1$-$C_5$ alkyl-N($C_1$-$C_3$ alkyl)₂, —$C_1$-$C_5$ alkyl-aryl, —$C_1$-$C_5$ alkyl-heteroaryl, —$C_1$-$C_5$ alkyl-heterocyclyl, $C_1$-$C_5$ alkoxyl, $C_3$-$C_8$ cycloalkyl, —C(O)NH₂, —C(O)NH—$C_1$-$C_5$ alkyl, —C(O)N($C_1$-$C_5$ alky)₂, —C(O)NH—$C_3$-$C_8$ cycloalkyl, —C(O)O$C_1$-$C_5$ alkyl, halogen, cyano, heterocyclyl, aryl or heteroaryl; wherein each aryl and heteroaryl of said R⁶ is optionally independently substituted with 1 to 2 of $C_1$-$C_5$ alkyl; and n is 0 or 1;

or a pharmaceutically acceptable salt thereof.

7. The compound of claim 3 wherein:

R¹ is phenyl, isoxazolyl, imidazolyl, pyrazolyl, thiazolyl, pyridinyl, benzimidazolyl, pyrazolopyridinyl or quinolinyl; wherein each of the foregoing R1 groups optionally substituted with 1 to 3 substituents selected from R⁶;

R² and R³ are each independently H or $C_1$-$C_3$alkyl;

R⁴ and R⁵ are each independently H or $C_1$-$C_3$ alkyl; and each R⁶ is independently $C_1$-$C_5$ alkyl, —$C_1$-$C_5$ alkyl-N($C_1$-$C_2$ alkyl)₂, —$C_1$-$C_3$ alkyl-phenyl, —$C_1$-$C_3$ alkyl-pyridinyl, —$C_1$-$C_3$ alkyl-tetrahydrofuranyl, —$C_1$-$C_3$ alkyl-morpholinyl, $C_3$-$C_6$ cycloalkyl, —C(O)NH₂, —C(O)NH—$C_1$-$C_3$ alkyl, —C(O)NH—$C_3$-$C_6$ cycloalkyl, —C(O)O$C_1$-$C_3$ alkyl, halogen or heteroaryl; wherein each heteroaryl group of said R⁶ is optionally independently substituted with 1 to 2 of $C_1$-$C_3$ alkyl;

or a pharmaceutically acceptable salt thereof.

8. The compound of claim 3 wherein:

R¹ is phenyl, isoxazolyl, imidazolyl, pyrazolyl, pyridinyl, pyrazolopyridinyl or quinolinyl; wherein each of the foregoing R¹ groups is optionally substituted with 1 to 3 substituents selected from R⁶; and each R⁶ is independently $C_1$-$C_5$ alkyl, —$C_1$-$C_3$ alkyl-phenyl, —$C_1$-$C_3$ alkyl-pyridinyl, —$C_1$-$C_3$ alkyl-tetrahydrofuranyl, —$C_1$-$C_3$ alkyl-morpholinyl, —C(O)NH₂, —C(O)NH—$C_3$-$C_6$ cycloalkyl or;

or a pharmaceutically acceptable salt thereof.

9. A compound of claim 1 selected from the group consisting of:

10-methyl-6-oxo-N-[1-(pyridin-4-ylmethyl)-1H-pyrazol-4-yl]-7,8,9,10-tetrahydro-6H-pyrido[3',2':4,5]pyrrolo[1,2-a][1,4]diazepine-2-carboxamide;

N-(1-benzyl-1H-pyrazol-4-yl)-trans-8,9-dimethyl-6-oxo-6,7,8,9-tetrahydropyrido[3',2':4,5]pyrrolo[1,2-a]pyrazine-2-carboxamide;

(9R)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide;

N-(1-benzyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide;

(9S)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide;

(9R)-9-methyl-N-(5-methyl-1,2-oxazol-3-yl)-6-oxo-6,7,8,9-tetrahydropyrido[3',2':4,5]pyrrolo[1,2-a]pyrazine-2-carboxamide;

(9R)-9-methyl-6-oxo-N-[1-(propan-2-yl)-1H-pyrazolo[3,4-b]pyridin-5-yl]-6,7,8,9-tetrahydropyrido[3',2':4,5]pyrrolo[1,2-a]pyrazine-2-carboxamide;

(9R)-9-methyl-6-oxo-N-(quinolin-3-yl)-6,7,8,9-tetrahydropyrido[3',2':4,5]pyrrolo[1,2-a]pyrazine-2-carboxamide;

N-(2-carbamoylphenyl)-6-oxo-7,8,9,10-tetrahydro-6H-pyrido[3',2':4,5]pyrrolo[1,2-a][1,4]diazepine-2-carboxamide;

N-[2-(cyclopentylcarbamoyl)-1-methyl-1H-imidazol-4-yl]-6-oxo-7,8,9,10-tetrahydro-6H-pyrido[3',2':4,5]pyrrolo[1,2-a][1,4]diazepine-2-carboxamide;

N-(1-benzyl-1H-pyrazol-4-yl)-6-oxo-7,8,9,10-tetrahydro-6H-pyrido[3',2':4,5]pyrrolo[1,2-a][1,4]diazepine-2-carboxamide;

10-methyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide;

N-(1-tert-butyl-1H-pyrazol-4-yl)-6-oxo-7,8,9,10-tetrahydro-6H-pyrido[3',2':4,5]pyrrolo[1,2-a][1,4]diazepine-2-carboxamide;

N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide;

N-(1-tert-butyl-1H-pyrazol-4-yl)-10-methyl-6-oxo-7,8,9,10-tetrahydro-6H-pyrido[3',2':4,5]pyrrolo[1,2-a][1,4]diazepine-2-carboxamide;

N-[5-chloro-7-(morpholin-4-ylmethyl)-1H-benzimidazol-2-yl]-6-oxo-7,8,9,10-tetrahydro-6H-pyrido[3',2':4,5]pyrrolo[1,2-a][1,4]diazepine-2-carboxamide;

N-(5-benzyl-1,2-oxazol-3-yl)-cis-8,9-dimethyl-6-oxo-6,7,8,9-tetrahydropyrido[3',2':4,5]pyrrolo[1,2-a]pyrazine-2-carboxamide;

6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

6-oxo-N-(quinolin-3-yl)-7,8,9,10-tetrahydro-6H-pyrido[3',2':4,5]pyrrolo[1,2-a][1,4]diazepine-2-carboxamide;

10-methyl-6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

(9N)—N-(5-benzyl-1,2-oxazol-3-yl)-9-methyl-6-oxo-6,7,8,9-tetrahydropyrido[3',2':4,5]pyrrolo[1,2-a]pyrazine-2-carboxamide;

N-(4-methylpyridin-2-yl)-6-oxo-7,8,9,10-tetrahydro-6H-pyrido[3',2':4,5]pyrrolo[1,2-a][1,4]diazepine-2-carboxamide;

N-(1-ethyl-1H-benzimidazol-2-yl)-1-oxo-2,3,4,5-tetrahydro-1H-[1,4]diazepino[1,2-a]benzimidazole-8-carboxamide;

N-(3-benzyl-1,2-oxazol-5-yl)-6-oxo-7,8,9,10-tetrahydro-6H-pyrido[3',2':4,5]pyrrolo[1,2-a][1,4]diazepine-2-carboxamide; or a pharmaceutically acceptable salt thereof.

10. A compound of claim 1 selected from the group consisting of:

N-(5-benzyl-1,2-oxazol-3-yl)-10-methyl-6-oxo-7,8,9,10-tetrahydro-6H-pyrido[3',2':4,5]pyrrolo[1,2-a][1,4]diazepine-2-carboxamide;

10-methyl-6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

10-methyl-6-oxo-N-[1-(propan-2-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

N-(1-benzyl-1H-pyrazol-4-yl)-cis-8,9-dimethyl-6-oxo-6,7,8,9-tetrahydropyrido[3',2':4,5]pyrrolo[1,2-a]pyrazine-2-carboxamide;

N-(3-benzyl-1,2-oxazol-5-yl)-10-methyl-6-oxo-7,8,9,10-tetrahydro-6H-pyrido[3',2':4,5]pyrrolo[1,2-a][1,4]diazepine-2-carboxamide;

10-methyl-N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide;

Cis-8,9-dimethyl-N-(5-methyl-1,2-oxazol-3-yl)-6-oxo-6,7,8,9-tetrahydropyrido[3',2':4,5]pyrrolo[1,2-a]pyrazine-2-carboxamide;

N-(5-methyl-1,2-oxazol-3-yl)-6-oxo-7,8,9,10-tetrahydro-6H-pyrido[3',2':4,5]pyrrolo[1,2-a][1,4]diazepine-2-carboxamide;

N-(3-fluorophenyl)-6-oxo-7,8,9,10-tetrahydro-6H-pyrido[3',2':4,5]pyrrolo[1,2-a][1,4]diazepine-2-carboxamide;

5,5-dimethyl-1-oxo-N-[1-(propan-2-yl)-1H-benzimidazol-2-yl]-2,3,4,5-tetrahydro-1H-[1,4]diazepino[1,2-a]benzimidazole-8-carboxamide;

6-oxo-N-[1-(tetrahydro-2H-pyran-4-yl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

6-oxo-N-[1-(tetrahydrofuran-3-ylmethyl)-1H-pyrazolo[3,4-b]pyridin-5-yl]-7,8,9,10-tetrahydro-6H-pyrido[3',2':4,5]pyrrolo[1,2-a][1,4]diazepine-2-carboxamide;

N-(1-ethyl-1H-benzimidazol-2-yl)-cis-8,9-dimethyl-6-oxo-6,7,8,9-tetrahydropyrido[3',2':4,5]pyrrolo[1,2-a]pyrazine-2-carboxamide;

1-oxo-N-[1-(propan-2-yl)-1H-benzimidazol-2-yl]-2,3,4,5-tetrahydro-1H-[1,4]diazepino[1,2-a]benzimidazole-8-carboxamide;

N-(1-benzyl-1H-pyrazol-4-yl)-9,9-dimethyl-6-oxo-7,8,9,10-tetrahydro-6H-pyrido[3',2':4,5]pyrrolo[1,2-a][1,4]diazepine-2-carboxamide;

9-methyl-6-oxo-N-(pyridin-3-yl)-6,7,8,9-tetrahydropyrido[3',2':4,5]pyrrolo[1,2-a]pyrazine-2-carboxamide;

N-(1-ethyl-1H-benzimidazol-2-yl)-10-methyl-6-oxo-7,8,9,10-tetrahydro-6H-pyrido[3',2':4,5]pyrrolo[1,2-a][1,4]diazepine-2-carboxamide;

9,9-dimethyl-N-(1-methyl-1H-pyrazol-4-yl)-6-oxo-7,8,9,10-tetrahydro-6H-pyrido[3',2':4,5]pyrrolo[1,2-a][1,4]diazepine-2-carboxamide; or a pharmaceutically acceptable salt thereof.

11. A pharmaceutical composition comprising one or more compounds of claim 1, or the pharmaceutically acceptable salts thereof, optionally combined with one or more excipients and/or carriers.

12. A method treating a ribosomal S6 kinase2 (RSK2) regulated disorder comprising administering to a patient in need thereof a pharmaceutically effective amount of one or more compounds of claim 1, or the pharmaceutically acceptable salts thereof.

13. The method of claim 12, wherein the RSK2 regulated disorder is selected from the group consisting of cardiovascular disease, inflammatory disease, allergic disease, pulmonary disease, fibrotic disease, renal disease and cancer.

* * * * *